(12) United States Patent
Ianchulev

(10) Patent No.: US 11,925,580 B2
(45) Date of Patent: Mar. 12, 2024

(54) IMPLANTABLE BIOLOGIC STENT AND SYSTEM FOR BIOLOGIC MATERIAL SHAPING AND PREPARATION IN THE TREATMENT OF GLAUCOMA

(71) Applicant: Iantrek, Harrison, NY (US)

(72) Inventor: Tsontcho Ianchulev, Harrison, NY (US)

(73) Assignee: Iantrek, Inc., Harrison, NY (US)

( * ) Notice: Subject to any disclaimer, the term of this patent is extended or adjusted under 35 U.S.C. 154(b) by 1041 days.

(21) Appl. No.: 16/777,648

(22) Filed: Jan. 30, 2020

(65) Prior Publication Data

US 2020/0390601 A1    Dec. 17, 2020

Related U.S. Application Data

(60) Provisional application No. 62/943,106, filed on Dec. 3, 2019, provisional application No. 62/897,570, filed (Continued)

(51) Int. Cl.
*A61F 9/007* (2006.01)
*A61L 27/36* (2006.01)

(52) U.S. Cl.
CPC ...... *A61F 9/00781* (2013.01); *A61F 9/00763* (2013.01); *A61L 27/3604* (2013.01); *A61L 27/3641* (2013.01); *A61L 2430/16* (2013.01)

(58) Field of Classification Search
CPC .................. A61F 9/00781; A61F 9/00763
See application file for complete search history.

(56) References Cited

U.S. PATENT DOCUMENTS

| 4,288,066 A | 9/1981 | Treace |
| 5,662,661 A | 9/1997 | Boudjema |

(Continued)

FOREIGN PATENT DOCUMENTS

| CN | 101099695 A | 1/2008 |
| CN | 102481404 A | 5/2012 |

(Continued)

OTHER PUBLICATIONS

Einmahl et al. (2002). "Evaluation of a novel biomaterial in the suprachoroidal space of the rabbit eye." Invest Ophthalmol Vis Sci. 43:1533-1539.

(Continued)

*Primary Examiner* — Leslie R Deak
(74) *Attorney, Agent, or Firm* — Mintz Levin Cohn Ferris Glovsky and Popeo, P.C.

(57) ABSTRACT

A system for preparation of an implant and ab interno insertion of the implant into an eye including a handle having one or more actuators and an elongated shaft having an outer sheath and an elongate member positioned within a lumen of the tubular outer sheath. The system includes a recess sized for holding a patch of material fixed relative to the handle and a cutting member movable relative to the handle and to the recess. The cutting member cuts the patch of material into an implant as the cutting member moves towards a cutting configuration. The implant, once cut, is axially aligned with the lumen of the tubular outer sheath. The inner elongate member is movable relative to the tubular outer sheath to advance the implant into a deployment position in the lumen of the tubular outer sheath for delivery into the eye. Related devices and methods are provided.

93 Claims, 36 Drawing Sheets

Related U.S. Application Data on Sep. 9, 2019, provisional application No. 62/861,900, filed on Jun. 14, 2019.

(56) References Cited

U.S. PATENT DOCUMENTS

| | | | |
|---|---|---|---|
| 5,868,697 A * | 2/1999 | Richter | A61F 9/00781 604/294 |
| 5,868,728 A | 2/1999 | Giungo et al. | |
| 5,941,250 A | 8/1999 | Aramant et al. | |
| 6,036,678 A | 3/2000 | Giungo | |
| 7,207,965 B2 | 4/2007 | Simon | |
| 7,291,125 B2 | 11/2007 | Coroneo | |
| 7,815,592 B2 | 10/2010 | Coroneo | |
| 7,850,638 B2 | 12/2010 | Theodore Coroneo | |
| 8,128,588 B2 | 3/2012 | Coroneo | |
| 8,167,939 B2 | 5/2012 | Silvestrini et al. | |
| 8,172,899 B2 | 5/2012 | Silvestrini et al. | |
| 8,262,726 B2 | 9/2012 | Silvestrini et al. | |
| 8,337,393 B2 | 12/2012 | Silverstrini et al. | |
| 8,353,856 B2 | 1/2013 | Baerveldt | |
| 8,377,122 B2 | 2/2013 | Silvestrini et al. | |
| 8,444,588 B2 | 5/2013 | Yablonski | |
| 8,444,589 B2 | 5/2013 | Silvestrini | |
| 8,535,333 B2 | 9/2013 | de Juan, Jr. et al. | |
| 8,574,294 B2 | 11/2013 | Silvestrini et al. | |
| 8,617,139 B2 | 12/2013 | Silvestrini et al. | |
| 8,672,870 B2 | 3/2014 | Silvestrini et al. | |
| 8,721,656 B2 | 5/2014 | De Juan, Jr. et al. | |
| 8,728,021 B2 | 5/2014 | Theodore Coroneo | |
| 8,734,378 B2 | 5/2014 | De Juan, Jr. et al. | |
| 8,758,289 B2 | 6/2014 | Theodore Coroneo | |
| 8,758,290 B2 | 6/2014 | Horvath et al. | |
| 8,771,218 B2 | 7/2014 | Coroneo | |
| 8,801,649 B2 | 8/2014 | De Juan, Jr. et al. | |
| 8,814,819 B2 | 8/2014 | De Juan, Jr. et al. | |
| 8,852,137 B2 | 10/2014 | Horvath et al. | |
| 8,932,205 B2 | 1/2015 | Silvestrini et al. | |
| 8,945,038 B2 | 2/2015 | Yablonski | |
| 8,974,511 B2 | 3/2015 | Horvath et al. | |
| 9,155,656 B2 | 10/2015 | Schaller et al. | |
| 9,173,774 B2 | 11/2015 | Yaron et al. | |
| 9,192,516 B2 | 11/2015 | Horvath et al. | |
| 9,216,107 B2 | 12/2015 | Silvestrini et al. | |
| 9,241,832 B2 | 1/2016 | Schaller et al. | |
| 9,351,873 B2 | 5/2016 | Coroneo | |
| 9,398,977 B2 | 7/2016 | de Juan, Jr. et al. | |
| 9,421,130 B2 | 8/2016 | de Juan, Jr. | |
| 9,549,845 B2 | 1/2017 | de Juan, Jr. et al. | |
| 9,554,941 B2 | 1/2017 | Silvestrini et al. | |
| 9,585,789 B2 | 3/2017 | Silvestrini et al. | |
| 9,592,151 B2 | 3/2017 | Rangel-Friedman et al. | |
| 9,636,254 B2 | 5/2017 | Yu et al. | |
| 9,763,828 B2 | 9/2017 | Silvestrini et al. | |
| 9,788,999 B2 | 10/2017 | Schaller | |
| 9,789,000 B2 | 10/2017 | de Juan, Jr. et al. | |
| 9,877,866 B2 | 1/2018 | Horvath et al. | |
| 9,907,697 B2 | 3/2018 | Schaller et al. | |
| 9,962,290 B2 | 5/2018 | Burns et al. | |
| 9,987,472 B2 | 6/2018 | Tu et al. | |
| 10,085,633 B2 | 10/2018 | Schaller et al. | |
| 10,154,924 B2 | 12/2018 | Clauson et al. | |
| 10,159,600 B2 | 12/2018 | Horvath et al. | |
| 10,188,551 B2 | 1/2019 | Rangel-Friedman et al. | |
| 10,285,853 B2 | 5/2019 | Rangel-Friedman et al. | |
| 10,531,983 B2 | 1/2020 | Silvestrini et al. | |
| 10,695,218 B1 * | 6/2020 | Ianchulev | A61L 27/3604 |
| 10,888,460 B2 | 1/2021 | Sorensen et al. | |
| 10,905,591 B1 | 2/2021 | Ianchulev | |
| 2002/0133168 A1 * | 9/2002 | Smedley | A61F 9/00781 623/905 |
| 2003/0139809 A1 | 7/2003 | Worst et al. | |
| 2004/0167623 A1 | 8/2004 | Peyman | |
| 2004/0254520 A1 | 12/2004 | Porteous et al. | |
| 2007/0179455 A1 | 8/2007 | Geliebter et al. | |
| 2008/0208176 A1 | 8/2008 | Loh | |
| 2009/0143712 A1 | 6/2009 | Tu et al. | |
| 2010/0125237 A1 * | 5/2010 | Schocket | A61F 9/00781 604/8 |
| 2014/0236066 A1 * | 8/2014 | Horvath | A61L 31/08 604/9 |
| 2014/0379015 A1 | 12/2014 | Sorensen et al. | |
| 2015/0238687 A1 | 8/2015 | Novakovic et al. | |
| 2017/0095369 A1 | 4/2017 | Andino et al. | |
| 2018/0036173 A1 * | 2/2018 | Olson | A61F 9/00781 |
| 2019/0038399 A1 | 2/2019 | Muller | |

FOREIGN PATENT DOCUMENTS

| | | |
|---|---|---|
| CN | 104540472 A | 4/2015 |
| CN | 107847243 A | 3/2018 |
| GB | 2 551 102 A | 12/2017 |
| JP | 2013-059677 A | 4/2013 |
| WO | WO-2014/089548 A1 | 6/2014 |

OTHER PUBLICATIONS

Karlen et al. (Jan. 1999). "Deep sclerectomy with collagen implant: medium term results." Br. J. Ophthalmol, 83(1):6-11.

Krejcí L. (1974). "Microdrainage of anterior chamber of eye glaucoma operation using hydron capillary drain." Acta Univ Carol Med Monogr. (61):1-90.

Nesterov,AP et al. (1979). "Surgical stimulation of the uveoscleral outflow. Experimental studies on enucleated human eyes." Acta Opthalmol (Copenh) June; 57(3):409-17.

Larrañeta, E. et al. (2018). "Synthesis and characterization of hyaluronic acid hydrogels crosslinked using a solvent-free process for potential biomedical applications." Carbohydrate Polymers, 181, 1194-1205. https://doi.org/10.1016/j.carbpol.2017.12.015.

Regulatory Considerations for Human Cells, Tissues, and Cellular and Tissue-Based Products: Minimal Manipulation and Homologous Use. Guidance for Industry and Food and Drug Administration Staff. (Jul. 2020). 28 pages. Available at: www.fda.gov/regulatory-information/search-fda-guidance-documents/regulatory-considerations-human-cells-tissues-and-cellular-and-tissue-based-products-minimal. Web. Dec. 6, 2022.

"Preloaded Dsaek Tissue" Product sheet, Eversight Services, revised Sep. 23, 2019, 1 page. https://www.eversightvision.org/wp-content/uploads/2019/10/Preloaded_DSAEK_23Sept19.pdf (last accessed Nov. 11, 2019).

U.S. Appl. No. 17/178,066, filed Feb. 17, 2021, US 20210196516 A1.

U.S. Appl. No. 17/325,785, filed May 20, 2021, US 20210361484 A1.

U.S. Appl. No. 17/865,059, filed Jul. 14, 2022, US 20230009442 A1.

U.S. Appl. No. 17/940,380, filed Sep. 8, 2022, US 20230000680 A1.
U.S. Appl. No. 17/941,307, filed Sep. 9, 2022, US 20230082713 A1.
PCT/US22/42856, filed Sep. 8, 2022, WO 2023/039031 A1.
PCT/US22/43002, filed Sep. 8, 2022, WO 2023/039133 A1.

* cited by examiner

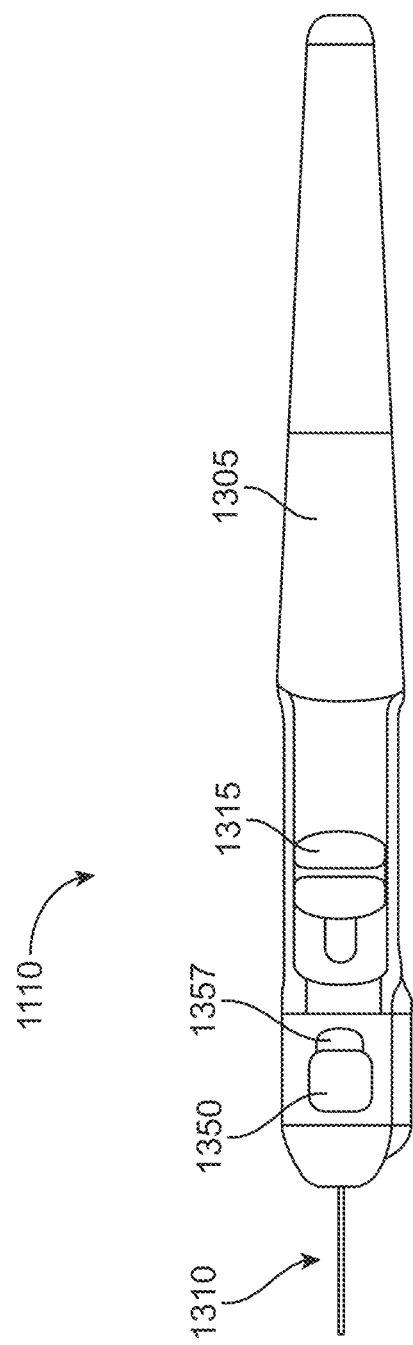
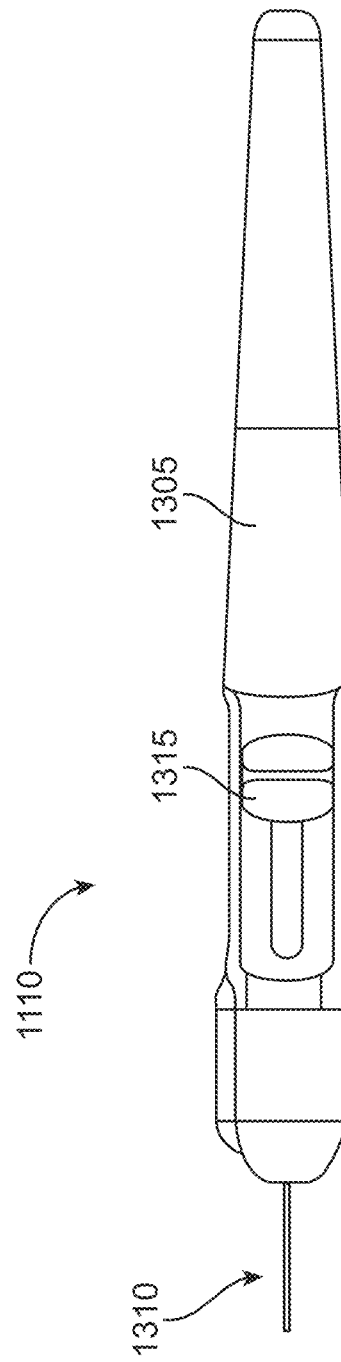
FIG. 13A
FIG. 13B

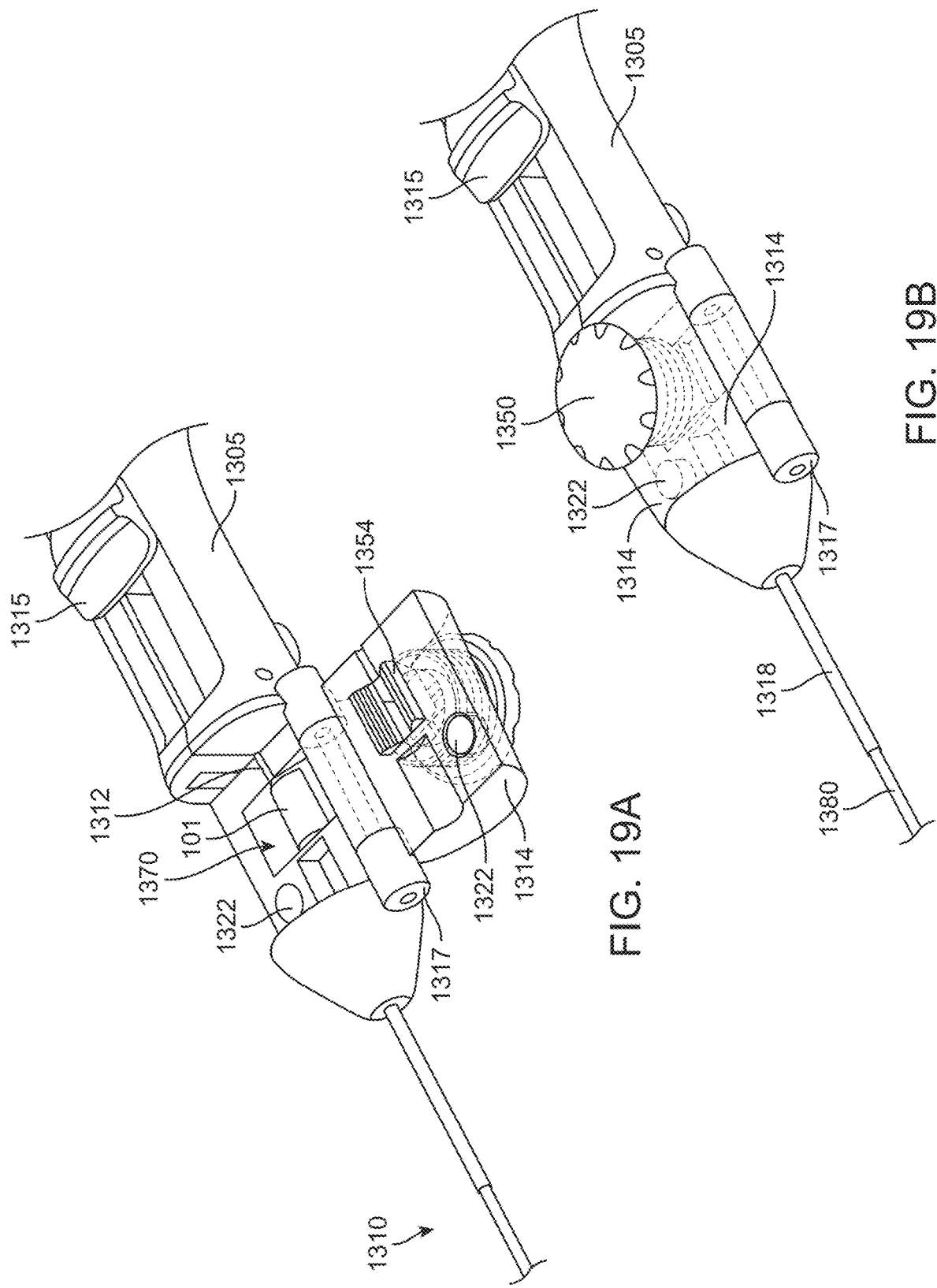

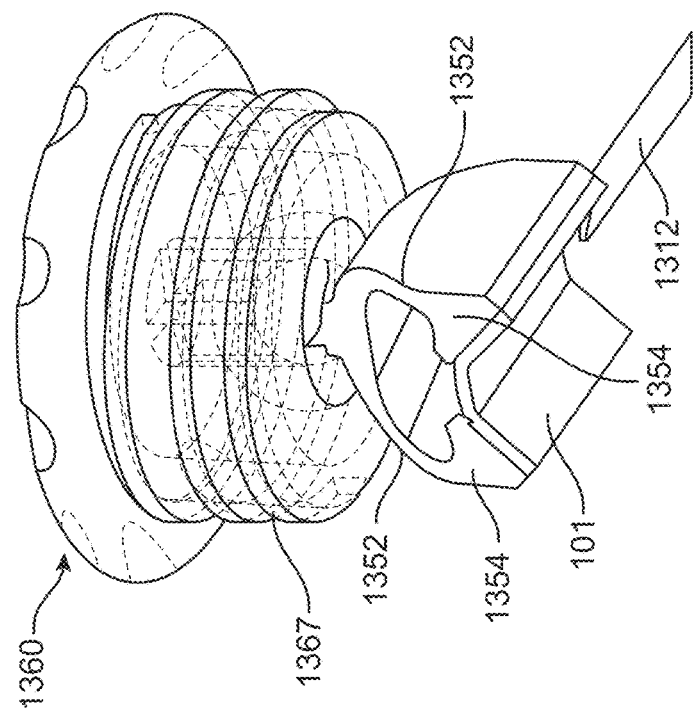
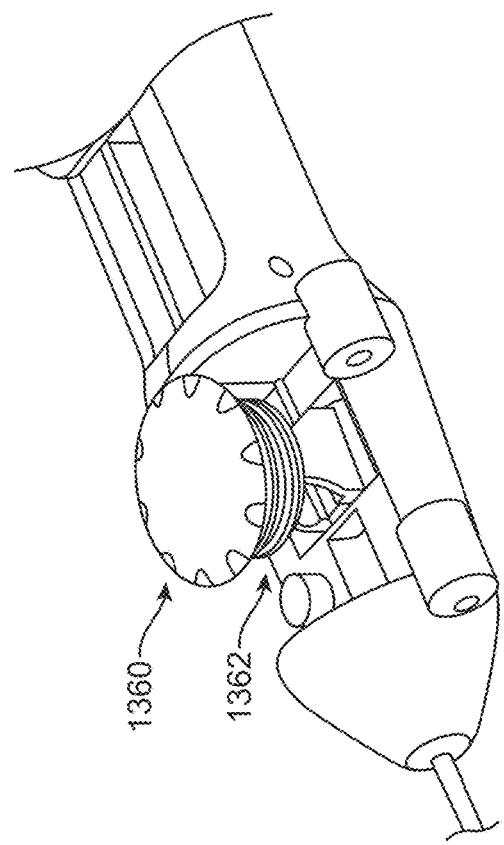
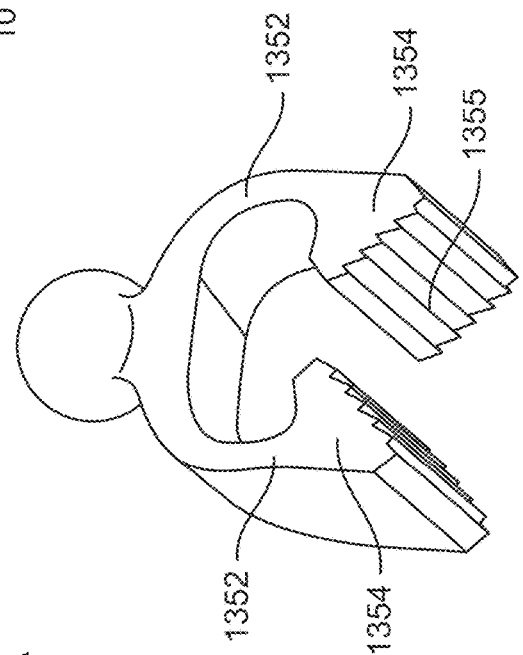
FIG. 20B
FIG. 20C
FIG. 20A

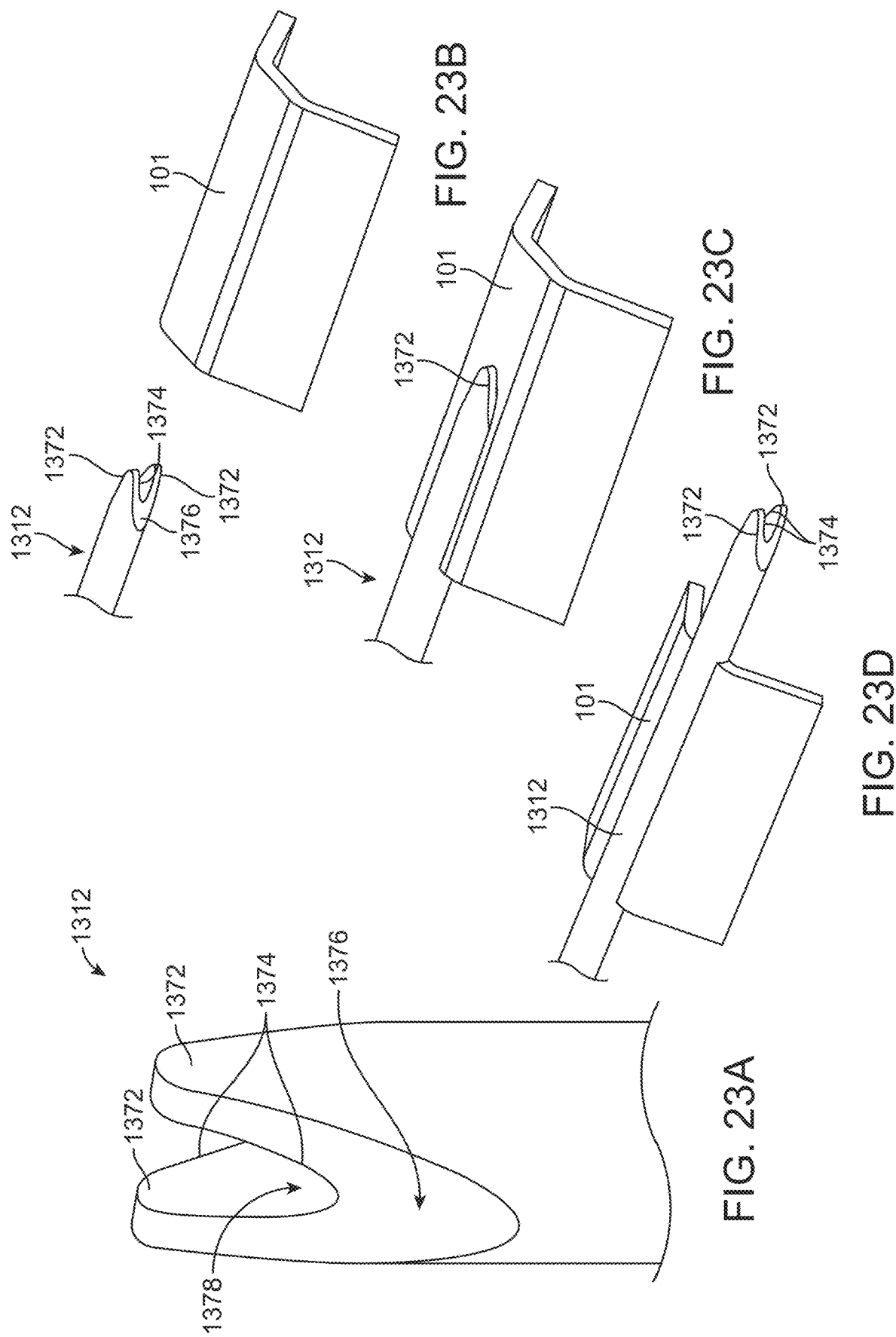

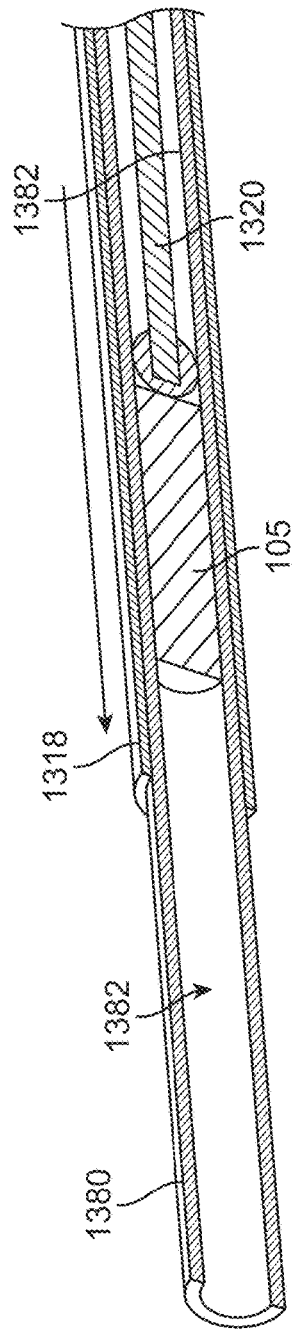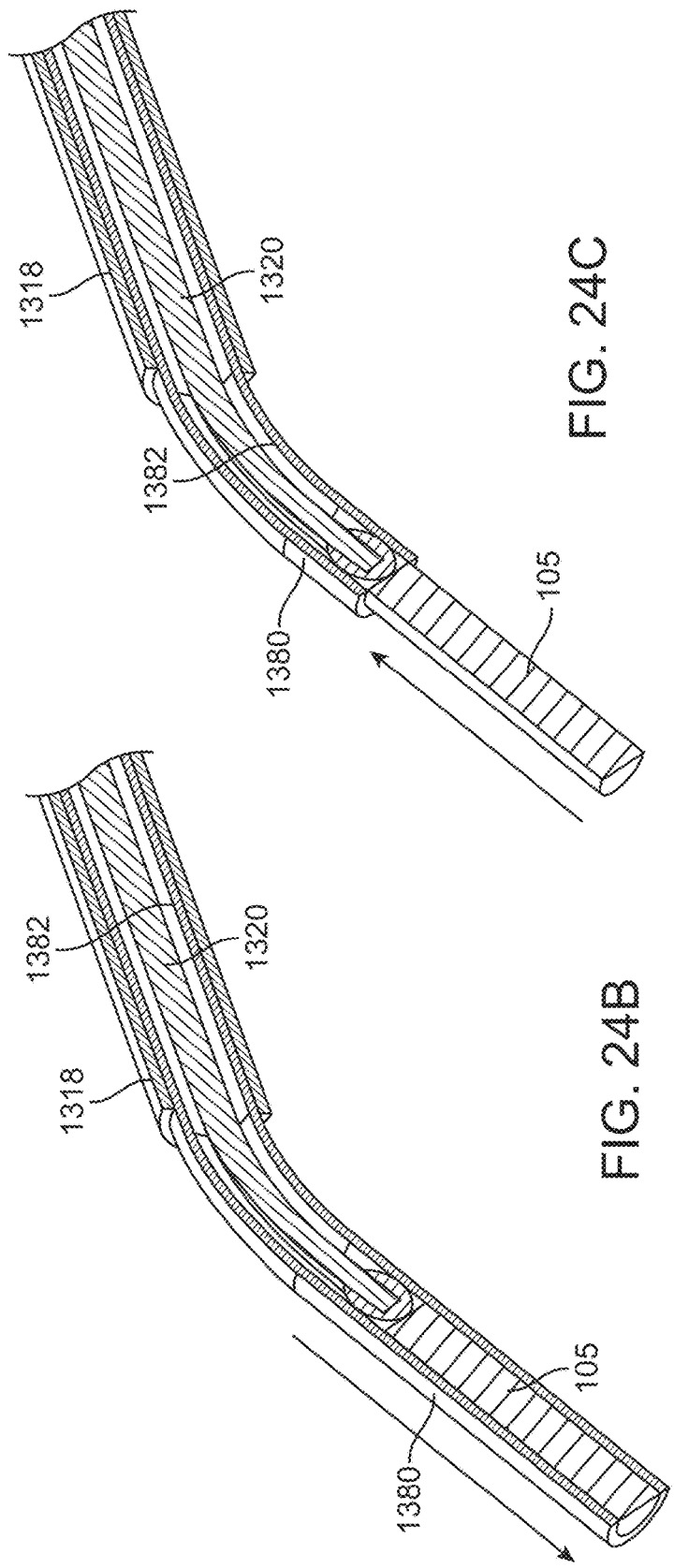

IMPLANTABLE BIOLOGIC STENT AND SYSTEM FOR BIOLOGIC MATERIAL SHAPING AND PREPARATION IN THE TREATMENT OF GLAUCOMA

CROSS-REFERENCE TO RELATED APPLICATIONS

This application claims the benefit of priority under 35 U.S.C. § 119(e) to U.S. Provisional Patent Application Ser. Nos. 62/861,900 filed Jun. 14, 2019; 62/897,570 filed Sep. 9, 2019; and 62/943,106 filed Dec. 3, 2019. The disclosures of the provisional applications are hereby incorporated by reference in their entireties.

BACKGROUND

The mainstay of ophthalmic surgery for glaucoma is the enhancement of aqueous outflow from the eye. There are various approaches to such surgery, including: 1) ab externo trabeculectomy or shunting, which requires cutting the conjunctiva and the sclera to penetrate the eye and provide a trans-scleral outflow path; 2) ab interno trabecular or trans-scleral outflow stenting or shunting of aqueous with hardware-based implantable devices or with ablating, non-implantable cutters such as dual-blade and trabectome; and 3) ab interno supraciliary stenting using implantable non-biological hardware implants.

Current ab interno stenting devices and methods are based on non-biological hardware materials such as polyimide, polyethersulphone, titanium, poly styrene-blocks-isobutylene-block-styrene and others. There are significant drawbacks with such non-biological hardware-based implantable devices as such devices can lead to major erosion, fibrosis and ocular tissue damage such as endothelial cell loss.

In view of the foregoing, there is a need for improved devices and methods related to ophthalmic surgery for the treatment of glaucoma.

SUMMARY

Disclosed are methods and devices for lowering, adjusting, or otherwise regulating intraocular pressure in an eye by way of implantation of a minimally invasive, bio-tissue stent in the eye. In an example implementation, a bio-tissue implant, such as a bio-tissue stent, shunt, or implant, is implanted into the eye such that the stent is at least partially positioned in a suprachoroidal, trans-scleral, and/or supraciliary location in the eye for treating glaucoma. The stent can be implanted via an ab interno delivery pathway into the eye using a delivery device that is configured for such a delivery pathway. In an example implementation, the stent assists or otherwise provides for drainage of aqueous humor from the anterior chamber to a uveoscleral outflow pathway of the eye. The stent provides a fluid passageway between the anterior chamber and a suprachoroidal space and/or the supraciliary space. The stent provides a fluid passageway/outflow in two independent yet potentially collaborative ways such as by stenting the supraciliary cleft and by using hydrophilic biologic material that allows transudative aqueous flow through the material itself. Other drainage pathways are considered including Schlemm's canal or via a subconjunctival location.

In an aspect, provided is a system for preparation of an implant and ab interno insertion of the implant into an eye. The system includes a handle having one or more actuators; an elongated shaft extending in a distal direction from the handle. The elongated shaft having a tubular outer sheath and an inner elongate member positioned within a lumen of the tubular outer sheath. The system includes a recess sized for holding a patch of material fixed relative to the handle and a cutting member movable relative to the handle and to the recess into a cutting configuration. The cutting member cuts the patch of material into an implant as the cutting member moves towards the cutting configuration. The implant, once cut, is axially aligned with the lumen of the tubular outer sheath. The inner elongate member is movable relative to the tubular outer sheath to advance the implant into a deployment position in the lumen of the tubular outer sheath for delivery into the eye.

The patch of material can include biologically-derived material suitable for transplant into the eye. The biologically-derived material can include tissue harvested from a donor or from the eye. The biologically-derived material can be autograft, allograft, or xenograft material. The material can be engineered tissue. The engineered tissue can be 3D-printed material suitable for implantation. The biologically-derived material can have a permeability and/or firm structure allowing for aqueous outflow from the eye when the implant cut from the patch of material is positioned within a cyclodialysis cleft. The implant cut from the patch of material can be bioabsorbable or non-bioabsorbable.

The implant can include one or more therapeutic agents. The one or more therapeutic agents can include antiproliferatives, antifibrotics, anesthetics, analgesics, cell transport/mobility impending agents, antiglaucoma drugs, prostaglandin analogues, carbonic anhydrase inhibitors, neuroprotectants, antibiotics, anti-viral agents, antiallergenics, anti-inflammatories, mydriatics, or immunomodulators.

The patch of material can be compressed and/or tensioned before the cutting member is moved into the cutting configuration. The patch of material can be compressed between two appositional planar surfaces preventing movement during subsequent cutting of the patch of material with the cutting member. The patch of material can be tensioned by a pair of flexible stretcher legs configured to apply a stretching force away from a center line of the patch of material.

The system can further include a cartridge detachably coupled to a region of the handle. The cartridge can include a base and a cover. The recess can be positioned within the base of the cartridge. The recess can be positioned within the handle. The system can further include an access door coupled to the handle and configured to enclose the recess when rotated to a closed configuration and reveal the recess when rotated to an open configuration. The access door can be formed of a transparent or translucent material. The system can further include projection extending upward from a center line of the recess forming two channels within the recess on either side of the projection. The projection can urge a centerline of the patch of material upward toward the door. The patch of material can be captured between the projection and the access door when the access door is rotated to the closed configuration relative to the handle. The access door can be configured to apply tension to the patch of material when the access door is in the closed configuration. The access door can include an actuator configured to apply the tension. The actuator can include a pair of flexible stretcher legs configured to extend into the recess. The pair of flexible stretcher legs can include a first foot that contacts the patch of material on a first side of the center line and an opposite foot that contacts the patch of material on an opposite side of the center line. The first foot and the opposite foot can be urged outward away from one another as the pair of stretcher legs are urged further into the recess by the actuator stretching the patch of material relative to the center line.

At least a proximal portion of the elongated shaft can extend along a longitudinal axis. A distal end region of the elongated shaft can be angled away from the longitudinal axis. A distal end region of the elongated shaft can have a maximum outer diameter that is no greater than about 1.3 mm. A distal-most tip of the elongated shaft can be blunt to allow for dissecting between tissues of the eye without cutting the tissues. The tubular outer sheath can be a hypotube having an inner diameter that is less than about 0.036" to about 0.009". The implant cut from the patch of material can have a dimension that substantially fills an inner diameter of the tubular outer sheath.

The tubular outer sheath can be coupled to a first actuator and the inner elongate member is coupled to a second actuator. The first actuator can be positioned on an lower surface of the handle configured to proximally retract the tubular outer sheath and the second actuator can be positioned on an upper surface of the handle configured to distally advance the inner elongate member. Distal advancement of the inner elongate member can urge the implant distally through the lumen of the tubular outer sheath into a primed position near a distal opening from the lumen of the tubular outer sheath. Proximal retraction of the tubular outer sheath while the inner elongate member remains stationary relative to the handle can unsheathe the implant from the elongated shaft to deploy it within the eye.

The tubular outer sheath can be an introducer tube movable through a lumen of a fixed outer tube. The inner elongate member can be movable within the introducer tube. The introducer tube can be more flexible than the inner elongate member and the inner elongate member can be more flexible than the fixed outer tube. The inner elongate member can take on the shape of the fixed outer tube when retracted proximally and relax back into a curved shape when extended distally out of the outer tube. The introducer tube can conform to the curved shape of the inner elongate member when both the introducer tube and the inner elongate member are extended distally out of the outer tube.

In an interrelated aspect, provided is a cartridge for use with a system for preparation of an implant and ab interno insertion of the implant into an eye. The cartridge includes a base having an upper surface defining a recess sized and shaped to receive a patch of material to be cut into an implant. The cartridge includes a cover movably coupled to the base between an open configuration and a closed configuration. The cover has a lower surface arranged to appose the upper surface of the base when the cover is in the closed configuration. The cartridge includes a cutting member movable relative to the base and to the recess into a cutting configuration. The cutting member cuts the patch of material into the implant as the cutting member moves towards the cutting configuration. The implant, once cut, is axially aligned with a lumen of a tubular outer sheath for delivery into the eye.

When the cover is in the closed configuration, the patch of material can be held fixed relative to the base. When the cover is in the closed configuration, the patch of material can be compressed within the recess. The cover can be configured to apply tension on the patch of material compressed within the recess.

In an interrelated aspect, provided is a method of preparing an implant for implantation into, and of inserting the implant into, an eye of a patient. The method includes inserting a patch of a material into a proximal portion of an instrument. The instrument further includes a cutting member and a distal portion sized for insertion into an eye. The method includes cutting the patch with the cutting member to form the implant. The method includes advancing the implant from the proximal portion of the instrument into a deployment position in a lumen of an elongate tubular member of the distal portion. The method includes inserting the distal portion of the instrument into the anterior chamber of the eye. The method includes positioning the distal portion adjacent eye tissue and deploying the implant from the instrument.

Inserting the patch of the material can include inserting the patch into a recess in the proximal portion and closing a cover over the recess. The cover can be adapted to engage at least some portion of the patch of the material before the cutting. At least a portion of the cover can be transparent. The cover can prevent movement of the patch during the cutting of the patch with the cutting member. The method can further include tensioning at least a portion of the patch of the material before cutting the patch. The tensioning of the portion of the patch can include compressing a first portion and a second portion of the patch and tensioning a central portion of the patch, the central portion located between the first and second portions. The central portion of the patch can include the implant upon the cutting the patch with the cutting member. Tensioning the portion of the patch can include activating an actuator to tension the portion of the patch. Activating an actuator can include rotating the actuator to tension the portion of the patch. The cover can include an actuator, and actuation of the actuator tensions at least a portion of the patch. The method can further include inserting the distal portion of the instrument ab interno into the anterior chamber through a corneal incision, while the proximal portion of the instrument remains outside the eye. The material can be biologically-derived material suitable for implantation into the eye. The biologically-derived material can be tissue harvested from a donor or from the patient, or autograft, allograft, or xenograft material. The material can be an engineered or 3D-printed material suitable for implantation. The implant can include one or more therapeutic agents.

Deploying the implant from the instrument can result in the implant residing at least in part between a ciliary body and sclera of the eye of the patient. The implant can reside between the ciliary body and sclera within a cyclodialysis cleft. The cutting member can include a cutting member lumen, a distal opening and a pair of opposed cutting edges. The cutting can include advancing the cutting member to cut the patch of the material and capturing the implant within the cutting member lumen. The pair of opposed cutting edges can cut the patch in two locations to separate the implant from a remainder of the patch. An internal diameter of the elongate tubular member can be substantially the same as an internal diameter of the cutting member lumen. A distal portion of the cutting member can be beveled. The implant can include a longitudinal axis. The longitudinal axis of the implant can remain aligned with a longitudinal axis of the lumen of the elongate tubular member as the cutting member finishes cutting the patch to form the implant.

Advancing the implant from the proximal portion of the instrument can include pushing the implant out of the cutting member lumen and into the lumen of the elongate tubular member of the distal portion. A distal end region of the elongate tubular member can be at least one of angled or curved or flexible. The method can further include activating a first actuator to tension at least a portion of the patch before the cutting; activating a second actuator to advance the cutting member to cut the patch after the tensioning; activating a third actuator to advance the implant into the deployment position; and activating a fourth actuator to deploy the implant from the instrument, wherein each of the actuators is operatively coupled to the instrument.

Positioning the distal portion adjacent eye tissue can include positioning the implant between the ciliary body and sclera while the implant remains at least partially inside the lumen of the distal portion. Deploying the implant from the instrument can include retracting the elongate tubular portion from the implant while maintaining the implant's position relative to the adjacent eye tissue. A distal-most tip of the elongate tubular member can be blunt to allow for dissecting the eye tissue without cutting the eye tissue. Closing the cover over the recess can include engaging a portion of the cover with a first portion of the patch to compress the first portion of the patch and to tension a second portion of the patch.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings. Generally, the figures are not to scale in absolute terms or comparatively, but are intended to be illustrative. Also, relative placement of features and elements may be modified for the purpose of illustrative clarity.

FIG. 13A is a top view of an implementation of a delivery device;

FIG. 13B is a bottom view of the delivery device of FIG. 13A;

FIGS. 19A-19B are partial views of the delivery device of FIG. 18A;

FIGS. 20A-20C illustrate a stretcher configured to apply tension on a patch of material;

FIGS. 23A-23D are detailed, partial views of the cutter tube of FIG. 22;

FIGS. 24A-24C are partial, cross-sectional views of the cut stent being released from the delivery shaft if FIG. 18A;

Figure 1:
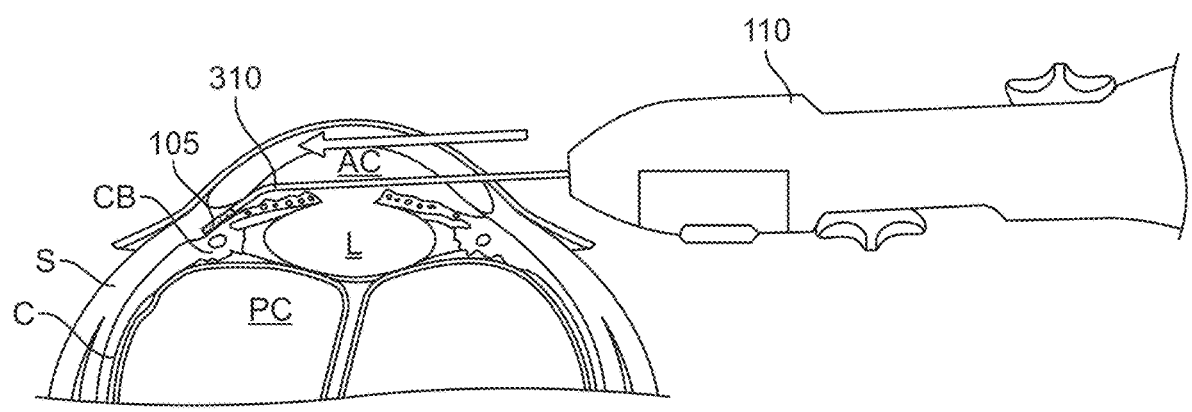
FIG. 1 is a cross-sectional view of a human eye showing the anterior and posterior chambers of the eye with a stent positioned in the eye in an example location.

It should be appreciated that the drawings are for example only and are not meant to be to scale. It is to be understood that devices described herein may include features not necessarily depicted in each figure.

DETAILED DESCRIPTION

Disclosed are implants, systems, and methods for increasing aqueous outflow from the anterior chamber of an eye. As will be described in detail below, ab interno outflow stenting using biological, cell-based or tissue-based materials provides biocompatible aqueous outflow enhancement with improved tolerability and safety over conventional shunts. In an example implementation, a biologic tissue or biologically-derived material is harvested or generated in vitro and formed into an implant, also referred to herein as a stent, using a trephination device or cutting tool. In an implementation, the stent is an elongated body or strip of tissue that does not have an internal lumen. Lumen-based devices can be limited by the lumen acting as a tract for fibrotic occlusion. The stent formed from the tissue is then implanted into the eye via an ab interno delivery pathway to provide aqueous outflow from the anterior chamber. The stents described herein can be used as a phacoemulsification adjunct or stand-alone treatment to glaucoma as a micro-invasive glaucoma surgery (MIGS) treatment.

Use of the terms like stent, implant, shunt, bio-tissue, or tissue is not intended to be limiting to any one structure or material. The structure implanted can, but need not be a material that is absorbed substantially into the eye tissue after placement in the eye such that, once absorbed, a space may remain where the structure was previously located. The structure once implanted may also remain in place for an extended period and not substantially erode or absorb.

As will be described in more detail below, the stents described herein can be made from biologically-derived material that does not cause toxic or injurious effects once implanted in a patient.

The term "biologically-derived material" includes naturally-occurring biological materials and synthesized biological materials and combinations thereof that are suitable for implantation into the eye. Biologically-derived material includes a material that is a natural biostructure having a biological arrangement naturally found within a mammalian subject including organs or parts of organs formed of tissues, and tissues formed of materials grouped together according to structure and function. Biologically-derived material includes tissues such as corneal, scleral, or cartilaginous tissues. Tissues considered herein can include any of a variety of tissues including muscle, epithelial, connective, and nervous tissues. Biologically-derived material includes tissue harvested from a donor or the patient, organs, parts of organs, and tissues from a subject including a piece of tissue suitable for transplant including an autograft, allograft, and xenograft material. Biologically-derived material includes naturally-occurring biological material including any material naturally found in the body of a mammal. Biologically-derived material as used herein also includes material that is engineered to have a biological arrangement similar to a natural biostructure. For example, the material can be synthesized using in vitro techniques such as by seeding a three-dimensional scaffold or matrix with appropriate cells, engineered or 3D printing material to form a bio-construct suitable for implantation. Biologically-derived material as used herein also includes material that is cell-derived including stem cell(s)-derived material.

The biologically-derived material, sometimes referred to herein as bio-tissue or bio-material, that is used to form the stent can vary and can be, for example, corneal tissue, scleral tissue, cartilaginous tissue, collagenous tissue, or other firm biologic tissue. The bio-tissue can be of hydrophilic or hydrophobic nature. The bio-tissue can include or be impregnated with one or more therapeutic agents for additional treatment of an eye disease process.

Non-biologic material includes synthetic materials prepared through artificial synthesis, processing, or manufacture that may be biologically compatible, but that are not cell-based or tissue-based. For example, non-biologic material includes polymers, copolymers, polymer blends, and plastics. Non-biologic material includes inorganic polymers such as silicone rubber, polysiloxanes, polysilanes, and organic polymers such as polyethylene, polypropylene, polyvinyls, polyimide, etc.

Regardless the source or type of biologically-derived material, the material can be cut or trephined into an elongated shape suitable for stenting and implantation in the eye. This trephination process of the tissue can be performed before the surgical implantation process or during the surgical implantation process. The stent(s) implanted in the eye may have a structure and/or permeability that allows for aqueous outflow from the anterior chamber when positioned within a cyclodialysis cleft.

FIG. 1 is a cross-sectional view of a human eye showing the anterior chamber AC and posterior chamber PC of the eye. A stent 105 can be positioned inside the eye in an implanted location such that at least a first portion of the stent 105 is positioned in the anterior chamber AC and a second portion of the stent 105 is positioned within tissues such as within the supraciliary space and/or suprachoroidal space of the eye. The stent 105 is sized and shaped such that the stent 105 can be positioned in such a configuration. The stent 105 provides or otherwise serves as a passageway for the flow of aqueous humor away from the anterior chamber AC (e.g. to the supraciliary space and/or suprachoroidal space). In FIG. 1, the stent 105 is represented schematically as an elongated body. It should be appreciated that the size and shape of the stent 105 can vary.

The stent 105 can be implanted ab interno, for example, through a clear corneal incision or a scleral incision. The stent can be implanted to create a communication between the anterior chamber AC and the supraciliary space, the anterior chamber AC and the suprachoroidal space, the anterior chamber AC and Schlemm's canal, or the anterior chamber AC and the sub-conjunctival space. In a preferred implementation, the stent 105 is implanted such that a distal end is positioned within a supraciliary position and the proximal end is positioned within the anterior chamber AC to provide a supraciliary cleft. The distal end of the stent 105 can be positioned between other anatomical parts of the eye.

Conventional glaucoma stenting devices are typically formed of non-biological materials such as polyimide or other synthetic materials that can cause endothelial tissue damage leading to progressive, long-term, and irreversible corneal endothelial loss. The stent materials described herein can reduce and/or eliminate these risks of tissue damage while still providing enhanced aqueous humor outflow.

The stent 105 described herein can be formed of any of a variety of biologically-derived materials having a permeability and/or structure that allows for aqueous filtration therethrough. The stent 105 can be formed of a biologically-derived material that is harvested, engineered, grown, or otherwise manufactured. The biologically-derived stent material can be obtained or harvested from a patient or from donors. The biologically-derived stent material can be harvested before or during surgery. The biologically-derived stent material can be synthetic bio-tissue created using in vitro techniques. The biologically-derived material can be stem cell generated or bioengineered. The tissue can be generated via in situ cellular or non-cellular growth. In an example implementation, the tissue can be 3D printed during manufacture.

The 3D printed tissue can be printed as a larger patch of material that is then cut at the time of surgery as described elsewhere herein. Alternatively, the 3D printed tissue can be printed to have the dimensions of the final implantable stent. In this implementation, the 3D printed material need not be trephined before implantation, but can be implanted directly. For example, the 3D printed stent can be printed directly into a cartridge that is configured to operatively couple with the delivery device described herein, which is in turn used to deploy the 3D printed stent into the eye. The 3D printed stent can be generated using the 3D printing process described in *Biofabrication*, 2019; 11 (3).

In an example implementation, the stent 105 is made of a bio-tissue. The biologically-derived material can be corneal tissue and/or non-corneal tissue. The biologically-derived material may include corneal, scleral, collagenous or cartilaginous tissue. In an implementation, the biologically-derived stent material can be denuded corneal stromal tissue without epithelium and endothelium that is porous and has hydrophilic permeability to allow aqueous filtration. The biologically-derived material of the stent 105 can, but need not be incorporated into the eye's inherent anatomy after placement in the eye. The stent can cause the surrounding tissue to form a pathway that remains open for an extended period, even after absorption of the stent. The biologically-derived stent material may not significantly absorb or be incorporated into the eye's anatomy such that the stent 105 remains implanted for an extended period of time or indefinitely, as needed.

In other implementations, the stent 105 material may be manufactured of a complex carbohydrate or a collagen that is non-inflammatory. The stent 105 may also be formed of a biodegradable or bioabsorbable material including biodegradable polymers including hydroxyaliphatic carboxylic acids, either homo- or copolymers, such as polylactic acid, polyglycolic acid, polylactic glycolic acid; polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-c-caprolactone, polydimethylsiloxane, polyamides, polyvinylpyrollidone, polyvinylalcohol phthallate, waxes such as paraffin wax and white beeswax, natural oils, shellac, zein, or a mixture.

As mentioned, the biologically-derived stent material can have a permeability or porosity that allows for aqueous filtration for sufficient control or regulation of intraocular pressure. Permeable bio-tissues described herein (e.g. sclera, cornea, collagen, etc.) are preferred stent materials, however, any bio-tissue, even if impermeable, is considered herein as a potential stent material to serve as a structural spacer that keeps the cyclodialysis open. Preferably, the material of the stent can create a gap that allows fluid to flow. The gap created can run longitudinally along each side of the stent. If the material of the stent is permeable, more fluid can pass through the cyclodialysis than if the stent material is impermeable and the fluid is required to pass along the outside of the stent. Thus, the material considered herein need not be porous in order to provide the desired function, however, the function can be enhanced by the porosity of the material.

Generally, the biologically-derived stent material has some firmness such that it can maintain outflow from the anterior chamber, however, is less stiff than conventional non-biologically-derived polyimide shunts used in the treatment of glaucoma (e.g. Cypass, Alcon). The stent material may have a sufficient structure to serve as a spacer to prop open a sustained supraciliary outflow. The stent material can maintain its structural height or thickness once implanted within the cyclodialysis such that fluid flow through or around the stent is provided. Biologically-derived stent material provides advantages in terms of biocompatibility, anatomic conformity, and aqueous permeability compared to conventional non-biological materials such as polyimide. Biologically-derived stent material can provide better conformability and compliance to the scleral wall and can be less likely to cause endothelial and scleral erosion/loss over time and with chronic eye rubbing and blinking.

In an implementation, the material used to form the stent is provided as an uncut patch of material configured to be manually loaded within the delivery device at the time of implantation. In other implementations, the biologically-derived material used to form the stent is provided as an uncut patch pre-loaded within the shaft of the delivery device and held within a trephination device 205 or cartridge. In still further implementations, the stent 105 comes already cut into the shape of the stent pre-loaded in the delivery device shaft 310 or within a cartridge configured to be loaded with the delivery device. The portion of the device carrying the biologically-derived stent material (whether pre-cut to a stent size or as the larger patch size) can be packaged in such a way that the material is stored in medium or other suitable preservative solution for the biologically-derived material. In some implementations, the entire device is packaged in a fluid bath or a portion of the device submerged in a separate container prior to attaching it to a trephination device or delivery device at the surgical site.

After the appropriate material has been obtained and prepped, a trephination device can be used to create an elongated stent of a predetermined dimension from the patch of material. As will be discussed in greater detail below, the trephination can be done at the time of surgery or prior to surgery. In certain implementations, the stent is formed by 3D printing and can be printed into a desired final dimension for the stent or can be printed as a patch of material that is then trephined at the time of or prior to surgery. The trephination achieved by the devices described herein results in very thin strips of material that can be implanted in the eye to provide regulation of aqueous outflow. The trephination achieved positions the cut implant within a conduit or lumen of the delivery device such that the cut implant may be subsequently delivered from the delivery device without needing to remove or transfer the cut implant from the cutting element into the delivery tube. The process of trephination can simultaneously or in subsequent actuations load the cut implant into a delivery conduit for implantation in the eye.

The term "patch of material" as used herein refers to a piece of biologically-derived material having a size along at least one dimension that is greater than a size of the stent cut from the patch of material and implanted in the subject. In some implementations, the patch of material can have a generally square shape and the stent trephined from the patch of material can have a generally rectangular shape. For example, the patch of material can be about 7 mm wide×7 mm long×0.55 mm thick and the stent trephined from the patch of material can be 0.3-0.6 mm wide×7 mm long×0.55 mm thick. The dimensions of the patch of material and the trephined stent can vary. The patch of material and the trephined stent can each have the same length and the same thickness, but differ from one another in width. The patch of material and the stent trephined from the patch of material can also have different lengths and thicknesses. For example, the patch of material can have a first thickness and the stent trephined from the patch of material have the same thickness, but when implanted can be folded or rolled into a different thickness from the patch of material.

The stent trephined from the patch of material can have a width, a length, and a thickness. In an implementation, the width of the stent trephined from the patch of material using the trephination devices described herein can be at least 100 microns up to about 1500 microns, or between 100 microns up to 1200 microns, or between 100 microns and 900 microns, or between 300 microns and 600 microns. The stent trephined from a patch of material can have a width of at least about 100 microns and a width of no more than 1500 microns, 1400 microns, 1300 microns, 1200 microns, 1100 microns, 1000 microns, 900 microns, no more than 800 microns, no more than 700 microns, no more than 600 microns, no more than 500 microns, no more than 400 microns, no more than 300 microns, or no more than 200 microns. The length of the stent trephined from a patch of material can vary depending on the location of stent implantation. In some implementations, the stent has a length that is between 1 mm and 10 mm, or more preferably between 3 mm and 8 mm long. The thickness of the stent trephined from the patch of material can be from 100 microns up to about 800 microns, or from 150 microns up to about 600 microns. In an implementation, the biological material forming the stent can have a thickness that is no smaller than 100 microns and no larger than 5 mm. The thickness of the stent can also depend on whether the stent is folded or rolled upon implantation such that a patch of material having a thickness of just 250 microns can cut into a stent and the stent folded at implantation to double the thickness to about 500 microns. The thickness of the stent can also depend upon what biologically-derived material is used. For example, scleral tissue or corneal tissue can often have a thickness of around 400 microns, but following harvest can shrink to about 250-300 microns. As such, a stent cut from a shrunken patch of corneal tissue may have a thickness of just 250 microns. In some implementations, which is described in more detail below, the stent cut from the patch of material is cut so as to substantially fill the conduit through which it is advanced for delivery.

In a non-limiting example, bio-tissue stent has dimensions no smaller than 0.1 mm and no larger than 8 mm in any direction and a thickness of not smaller than 50 microns and not larger than 8 mm. In a non-limiting example, the stent is about 6 mm in length by 300-600 microns wide by 150-600 microns thick. The trephination can be no smaller than 1 mm and no larger than 8 mm in any direction. In a non-limiting example, the trephined tissue has dimensions of 100-800 microns in width and 1 mm-10 mm in length. It should be appreciated that multiple stents may be delivered to one or more target locations during an implantation procedure.

The trephining devices described herein provide accurate and precise cutting without wrinkling. The trephining device can incorporate an anterior-to-posterior capture such that the material to be cut is held fixed on the z-plane preventing movement prior to engaging the tissue with a cutter. In implementations described in more detail below, the material to be cut is held fixed, compressed, and/or tensioned prior to cutting.

Figure 2A:
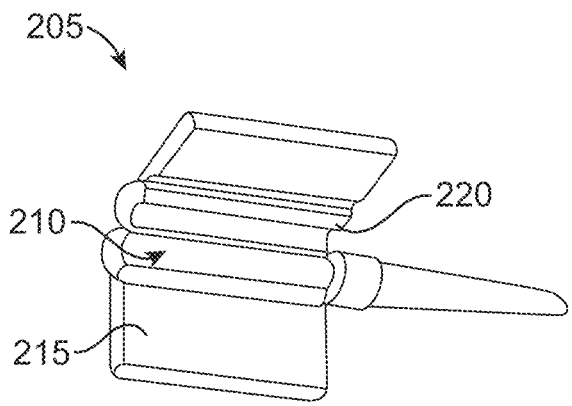
FIGS. 2A and 2B show example implementations of a trephination device for forming a stent.
Figure 2B:
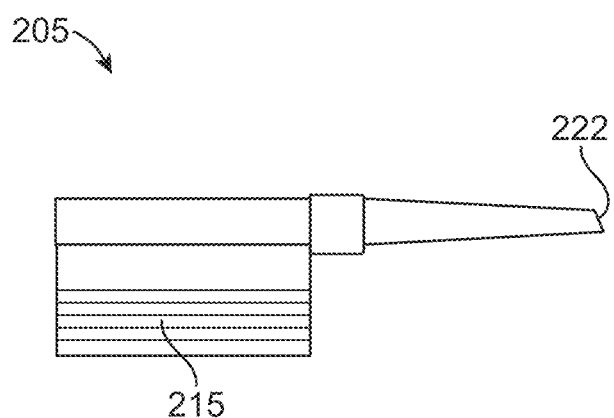
Figure 3:
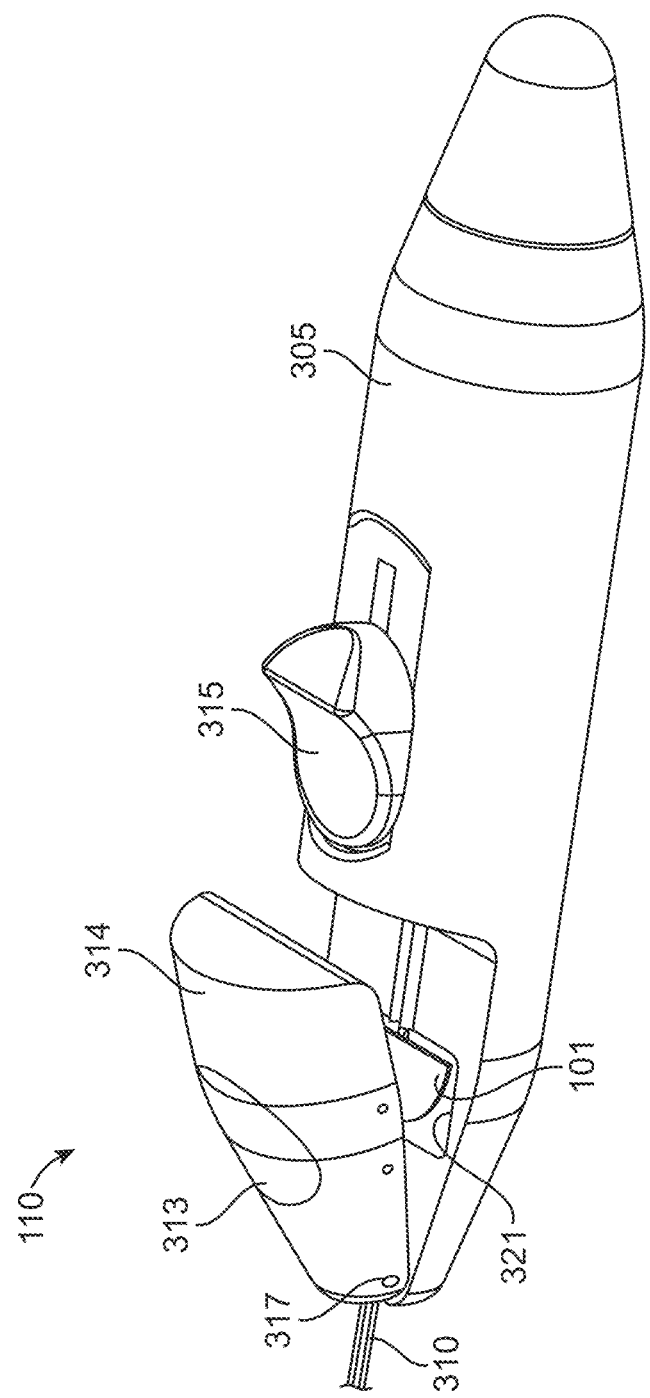
FIG. 3 shows a perspective view of an example implementation of a delivery device.
Figure 4:
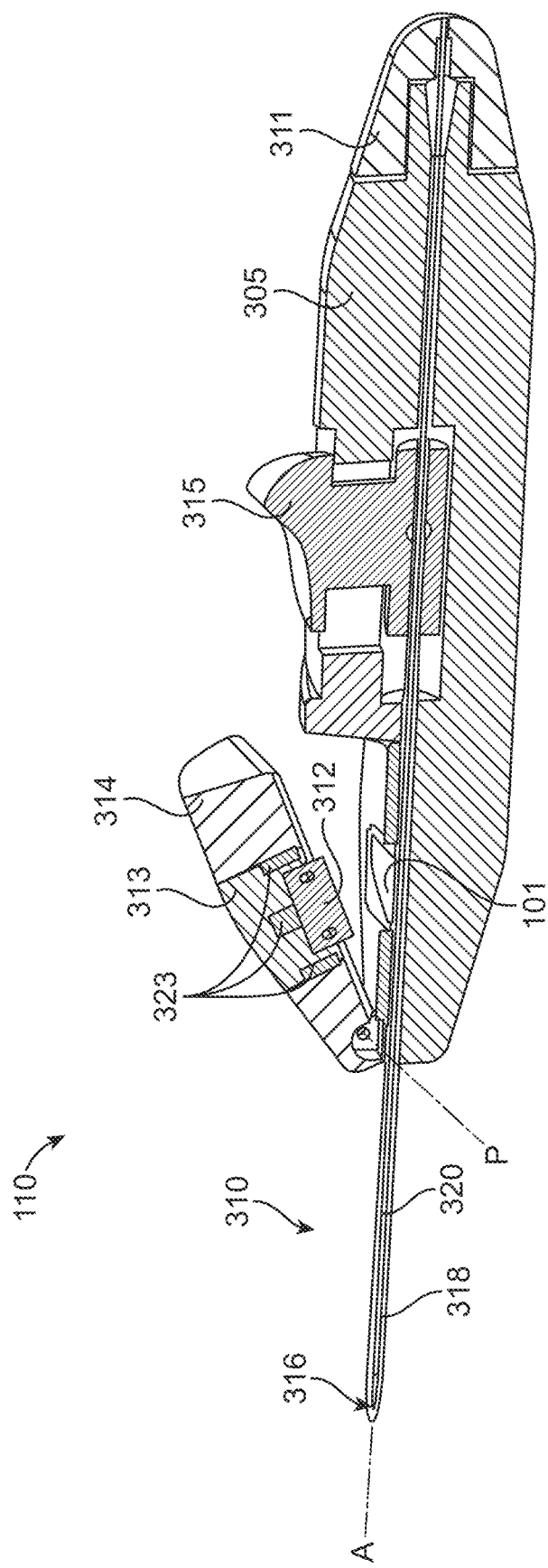
FIG. 4 shows a cross-sectional view of the delivery device.
Figure 5:
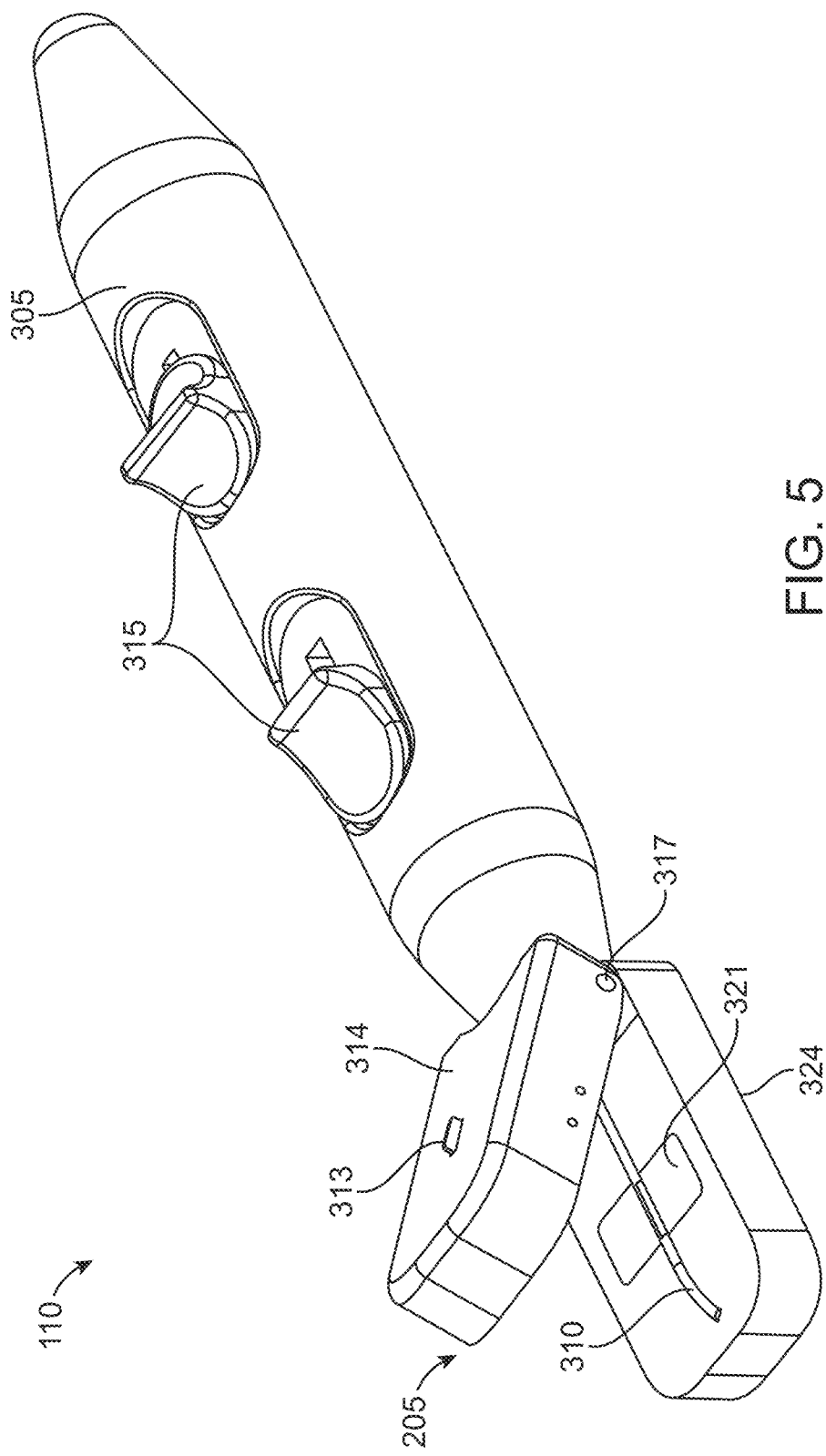
FIG. 5 shows an implementation of a delivery device having a trephination cartridge in an open configuration.
Figure 6A:
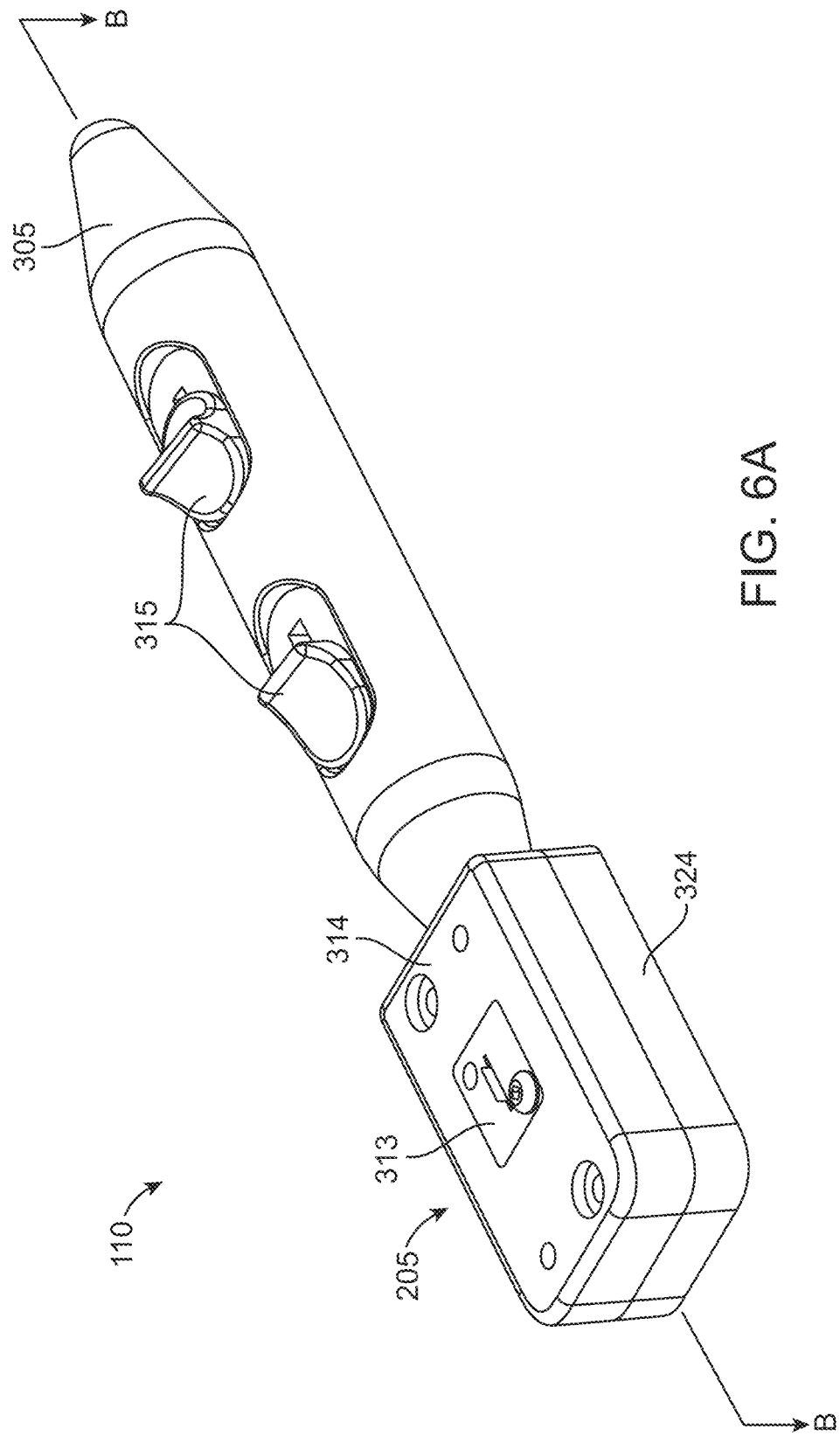
FIG. 6A shows an implementation of a delivery device having a trephination cartridge in a closed configuration.
Figure 6B:
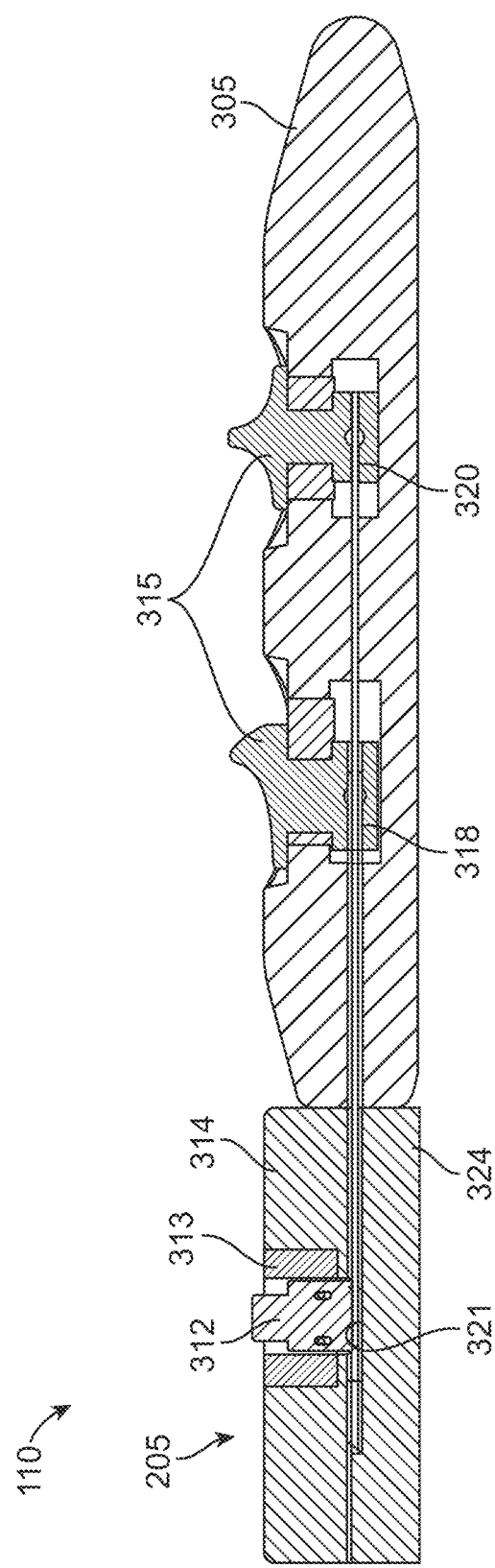
FIG. 6B is a cross-sectional view of the device in FIG. 6A taken along line B-B.

FIGS. 2A and 2B show example implementations of a trephination device 205. The intraoperative trephination device used to form the stent can be combined with or removably coupled to a delivery device, such as an applier/injector for delivery to the implanted location. FIGS. 3-4, FIGS. 13A-13B, and FIGS. 18A-18B show implementations of a trephination device integrated with a delivery device. The trephination devices can be a cartridge that removably couples to the delivery device as shown in FIGS. 5, and 6A-6B. The cartridge containing the patch of a material can be coupled to a distal portion of the delivery device as shown in FIG. 5 and FIGS. 6A-6B. In this implementation, the cartridge can be removed from the delivery device prior to deployment of the stent to the eye. The cartridge containing the patch of a material can alternatively be coupled to a proximal portion of the delivery device. In this implementation, the cartridge need not be removed prior to delivery of the stent into the eye and the stent cut from the patch of material can be deployed from the cartridge coupled to the delivery device without a separate step.

The trephination device is configured to cut or otherwise form the biologically-derived tissue or patch of a material having a first contour or shape (e.g., a wider, square sheet or patch of material) into a second contour or shape (e.g., a narrower, rectangular strip of material) that conforms to an implantable stent having the dimensions described herein. The cutting performed using the trephination devices described herein can involve guillotine, punch, rotating, sliding, rolling, or pivoting blade cutting motion. In some implementations, the cutting is performed orthogonal to the plane of the patch of material. In some implementations, the cutting is performed axially along the conduit of implantation. As such, the axis of trephination can be aligned, within, or parallel to the implantation conduit to allow unimpeded tissue loading and transfer for implantation without manipulating, tearing, or damaging the fragile stent tissue. The trephination process can be preceded by a tissue fixation step wherein the biologically-derived tissue that forms the stent is firmly fixed between two appositional planar surfaces to ensure the tissue is not wrinkled or malformed and the subsequent trephination cut is of accurate dimensions. The fixation can optionally provide tension or stretching of the tissue within at least one plane to ensure clean cutting through the tissue.

The trephination can be performed along or within a path or conduit formed within the structure, such as within a cartridge, the delivery device, or within any other structure. The trephination of the patch of material can simultaneously or subsequently position the implant within or aligned with a conduit (e.g., the lumen of the delivery shaft) so that the cut implant can be delivered to the eye through the conduit without the cut implant needing to be transferred to a separate delivery device. In some implementations, the cutting motion can be from above the patch of material such that the sharp edges of the blades cut the patch of material from an upper surface of the patch. As the cutter slides through the patch of material forming the implant it can then urge the cut implant down into the lumen of the delivery shaft along an axis orthogonal to the longitudinal axis A of the handle. In other implementations, the cutting motion can be along the longitudinal axis A of the handle sliding through the patch of material from a proximal end towards a distal end of the handle 305. The motion of the cutting can result in a cut implant already properly positioned and/or aligned with the delivery conduit of the delivery shaft. The cutting member can be movable relative to the handle as well as to a recess holding the patch of material into a cutting configuration. As the cutting member moves towards the cutting configuration it can cut the patch of material being held fixed within the recess forming the implant and the implant, once cut, can be axially aligned with the conduit for delivery.

The method of preparing an implant for implantation into an implant and for inserting the implant into the eye of patient can include inserting a patch of a material into a proximal portion of an instrument. The instrument can include the cutting member and a distal portion sized for insertion into the eye. Cutting the patch with the cutting member can form the implant. The implant, which can have a longitudinal axis, can align with a longitudinal axis of the lumen of the cutting member that cut the implant as the cutting member finishes cutting the patch of material to form the implant.

The implant can then be advanced from the proximal portion of the instrument into a deployment position in a lumen of an elongate tubular member of the distal portion of the instrument. The distal portion of the instrument is insertable into the anterior chamber of the eye so that it may be positioned adjacent eye tissue within which the implant is deployed from the instrument into the eye tissue. For example, the distal portion of the instrument can be inserted ab interno into the anterior chamber through a corneal incision, while the proximal portion of the instrument remains outside the eye. It should be appreciated that the distal portion of the instrument can be useful for other delivery pathways (e.g., trans-scleral delivery). Deploying the implant into the eye tissue can include the implant residing at least in part between a ciliary body and a sclera of the eye. The implant can reside between the ciliary body and the sclera within a cyclodialysis cleft.

Inserting the patch of the material includes inserting the patch into a recess, such as in the proximal portion of the instrument. The instrument can include a cover that is closed over the recess containing the patch. The cover is adapted to engage at least some portion of the patch of material before the cutting of the patch occurs. The cover can prevent movement of the patch during the cutting of the patch with the cutting member of the instrument. The cover (or some other element) can additional impose tensioning on at least a portion of the patch before cutting occurs. Tensioning can involve activating an actuator tension the portion of the patch although tensioning need not involve a separate actuation and can be a result of closing the cover itself. Closing the cover over the recess can include engaging a portion of the cover with a first portion of the patch to compress the first portion of the patch and to tension a second portion of the patch.

The structure desirably trephines the tissue in a manner such that the tissue can be slid, pushed, and/or pulled along the conduit toward an implanted location of the eye. In other implementations, the stent is held fixed in place and the conduit withdrawn from the stent leaving the stent implanted within the eye. The conduit can be incorporated into or coupled to a delivery device that implants and deploys the stent into the eye. The trephination device can be made of any of a variety of materials, such as a hard material including a plastic and/or a metal.

The trephination device 205 shown in FIGS. 2A-2B can have an internal lumen or enclosure 210 sized and shaped to form the elongated contour of the stent 105 when tissue is positioned within the enclosure 210. The enclosure 210 has a dimension that approximates within microns the size of the stent 105 to be formed. The trephination device 205 is configured to stabilize tissue during the trephination process. In this regard, the trephination device 205 can fix the tissue in place and prevent movement of the tissue relative to the trephination device 205 as the tissue is trephined. In an implementation, the trephination device 205 can have one or more wings 215 configured to articulate between an open (FIG. 2A) and closed (FIG. 2B) configuration. A patch of material can be placed within the enclosure 210 when the trephination device 205 is in the open configuration. One or more blades 220 may be positioned on an inner surface of the wings 215 such that when the wings 215 are articulated to the closed configuration and the patch of material is in place within the enclosure 210, the patch is cut into a stent having a desired dimension.

The enclosure 210 of the trephination device 205 can transition to and/or contain a corresponding lumen of a delivery device 110 that is configured to advance or otherwise inject the stent 105 into the eye. In an embodiment, the trephination device 205 trephines or cuts the tissue along a path that is aligned with or coaxial with a delivery pathway of the stent into the implanted location. For example, the stent cut from the patch of material held within the enclosure 210 can be urged distally through a lumen extending through a forward-end 222 of the trephination device 205 into a delivery device shaft. As such, the stent can be trephined first using a stand-alone trephination device. The trephination device holding the trephined stent can then be loaded into a delivery device, which is designed to accept the trephination device. This allows for loading the stent and deploying the stent without having to remove the stent from the trephination device in order to load it into the delivery device.

Trephination of stent material will be described in more detail below.

With reference again to FIG. 1, a delivery device 110 is configured to be removably coupled to the stent 105 and used to deliver the stent 105 into the implanted location via an ab interno delivery pathway. The delivery device 110 is schematically represented in FIG. 1. When coupled, the delivery device 110 can be inserted into the eye and used to implant the stent 105 in the implanted location via an ab interno delivery pathway.

The delivery devices described herein can prepare an implant and perform ab interno insertion of the implant into the eye. FIG. 3 shows a perspective view of an example implementation of a delivery device 110 having integrated trephination. FIG. 4 shows a cross-sectional view of the delivery device 110 of FIG. 3. The delivery device 110 can include a proximal handle 305 that is sized and shaped to be grasped by a single hand of a user. One or more actuators 315 can be positioned on a region of the handle 305. The actuator 315 can also be manipulated by the single hand of the user such as with a thumb or finger. The actuator 315 can be one or more of a knob, button, slider, or other interface configured to move one or more components of the delivery device 110 as will be described in more detail below.

An elongated shaft 310 (also referred to herein as an applicator or delivery body) extends in a distal direction outward from the handle 305. At least a portion of the shaft 310 contains or is coupled to the stent 105 for direct stent implantation. At least a portion of the shaft 310 extends along a longitudinal axis A. The shaft 310 can be angled, curved, or flexible at a distal end region such that it can form a distal curve or a bend. In some implementations, the shaft 310 can include a flexible portion and a rigid portion such that depending on relative position of the portions results in a change in shape of the shaft. The shaft 310 can be curved along at least its length and/or can be flexible.

The shaft 310 of the delivery device 110 has a size and shape is configured for ab interno delivery through a clear corneal incision to permit passage of the stent 105 out the distal end of the shaft 310 and left within the eye. In at least some methods, the distal end of the shaft 310 is sized to extend through an incision that is about 1 mm in length. In another implementation, the distal end of the shaft 310 is sized to extend through an incision that is no greater than about 2.5 mm in length. In another implementation, the distal end of the shaft 310 is sized to extend through an incision that is between 1.5 mm to 2.85 mm in length. In some implementations, the maximum outer diameter of the shaft 310 is no greater than 1.3 mm. The distal-most tip 316 of the shaft 310 can be blunt or sharp. A blunt distal-most tip 316 of the shaft 310 allows for dissecting between tissues of the eye without penetrating or cutting the tissues for positioning the stent 105. For example, the distal-most tip 316 of the shaft 310 can be configured to bluntly dissect between the ciliary body CB and the sclera S (e.g., the supraciliary space) while the stent 105 remains fully encased within the shaft 310 during the blunt dissection. In an alternative implementation, the distal-most tip 316 of the shaft 310 has a sharp cutting configuration for dissecting application and implantation through the scleral wall into the subconjunctival space. In yet another embodiment, the distal-most tip 316 can have a cutting configuration for dissecting and implantation into the Schlemm's canal or trans-sclerally.

The stents described herein are formed as solid strips of material without any lumen. Thus, the stents are not deliverable over a guidewire as many conventional glaucoma shunts are. Additionally, the stents are formed of relatively soft tissue that is more fragile as typical shunts formed of more rigid polymeric or metal material. More rigid shunts can be implanted such that a distal end of the shunt is used to create a blunt dissection at the interface of the tissues through which the shunt is being inserted. The stents described herein are preferably deployed using a retractable sleeved type of injector that once in proper anatomic position can be retracted leaving the stent more gently externalized and position. Additionally, the stents described herein can be deployed in the eye by urging the stent distally through at least a portion of the shaft 310. The stents can have a dimension that substantially fills an inner lumen of the shaft 310 (or the inner lumen of at least a portion of the shaft 310 through which it is delivered) such that the stent may be urged distally through that portion without wrinkling or being damaged. The tolerance between the outer dimensions of the stent 105 and the inner dimension of the conduit can be up to about 200%. The conduit can also be coated with a lubricious material (e.g., Teflon) to improve advancement of the stent 105 through the conduit during deployment.

The shaft 310 can define an internal, hollowed shape for containing the stent 105. In some implementations, the shaft 310 can be formed of an outer tube 318 (also referred to herein as a tubular outer sheath) and an inner pusher 320 (also referred to herein as an elongate member) positioned within the lumen of the outer tube 318 (see FIG. 4 and also FIGS. 7, 11C-11E). Movement of the outer tube 318 and/or the pusher 320 can act to deploy the stent 105 within the eye. The outer tube 318 and pusher 320 of the shaft 310 can be operatively coupled to the one or more actuators 315 in order to deliver a stent 105 to the eye. The outer tube 318 can be fixed relative to the handle 305 and the pusher 320 moveable relative to the handle 305. The outer tube 318 can be movable relative to the handle 305 and the pusher 320 fixed relative to the handle 305. Alternatively, both the outer tube 318 and the pusher 320 can be movable relative to the handle 305. Motion of the outer tube 318 and/or the pusher 320 can be generated using the same actuator 315 or different actuators 315 on the handle 305 that can be actuated by a user moving the actuator 315 relative to the handle 305. The type of movement of the actuator 315 relative to the handle 305 can vary, including sliding or rotatable movement. The implementation shown in FIGS. 3 and 4 can include a shaft 310 having an outer tube 318 and a pusher 320. The outer tube 318 can be coupled to a slider and the pusher 320 can be coupled to a knob 311 at a proximal region of the handle 305.

Once the desired position in the tissues is reached with the distal end of the shaft 310, the stent 105 is left in position in the eye and the shaft 310 withdrawn. In an implementation, the outer tube 318 of the shaft 310 is retracted, for example, using the actuator 315 on the handle while the pusher 320 remains stationary relative to the handle 305. The pusher 320 therefore can act as a stopper thereby preventing the stent 105 from following the outer tube 318 as it is retracted. The result is that the stent 105 is unsheathed from the shaft 310 and left within the tissues.

The delivery device 110 can further include a cutting member 312 (see FIG. 4), such as a blade or cutter tube, that can move relative to the handle 305 to cut tissue thereby forming the stent 105. As mentioned above, the stent 105 can be formed from a patch of material. The patch of material may be loaded within a region of the delivery device 110 and cut into a smaller stent shape at the time of delivery. The cutting member 312 can be actuated by a user to create the stent from the patch of material.

Figure 15A:
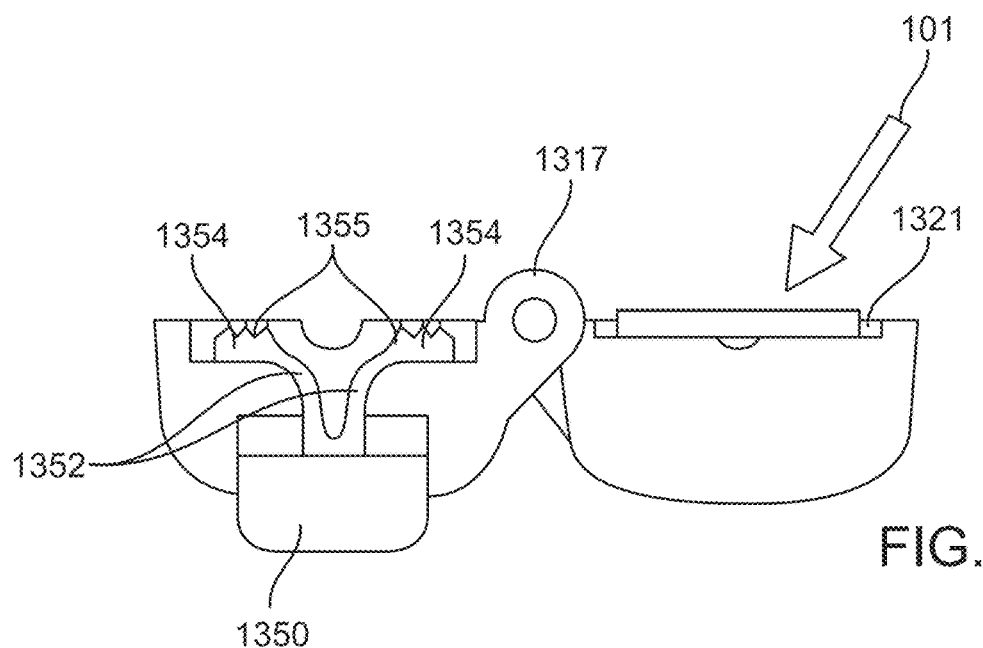
FIGS. 15A-15C are schematic views of a stretcher applying tension on a patch of material.
Figure 15B:
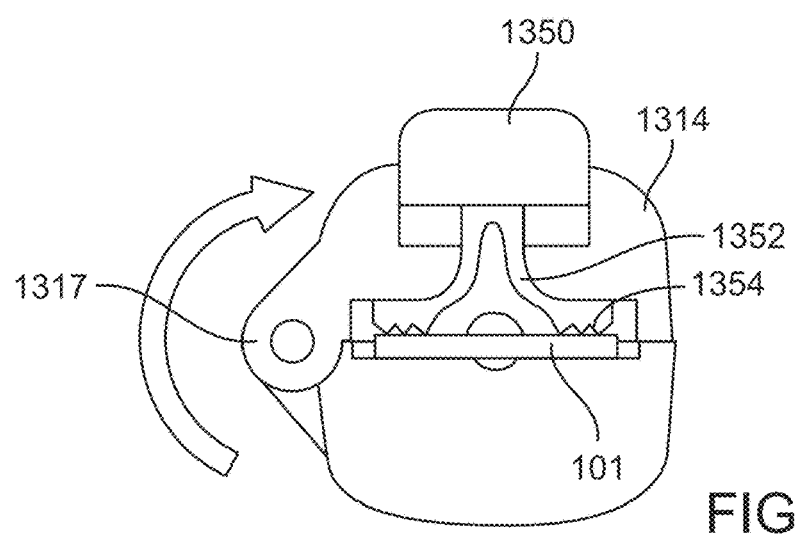
Figure 15C:
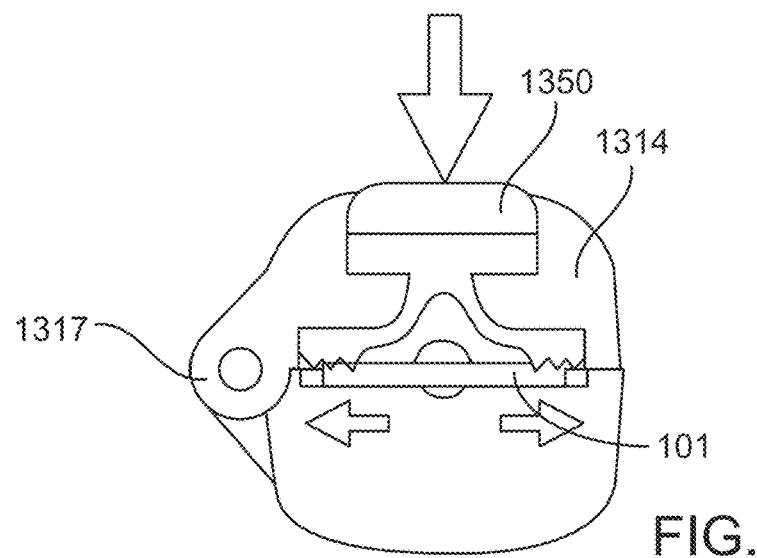
Figure 16B:
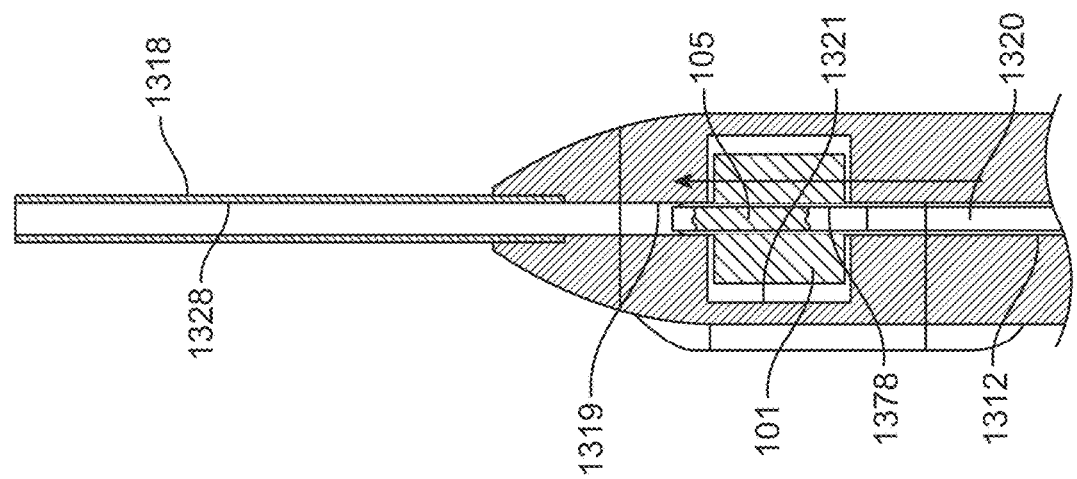
FIGS. 16A-16B are schematic views of a cutter tube cutting a patch of material.
Figure 16A:
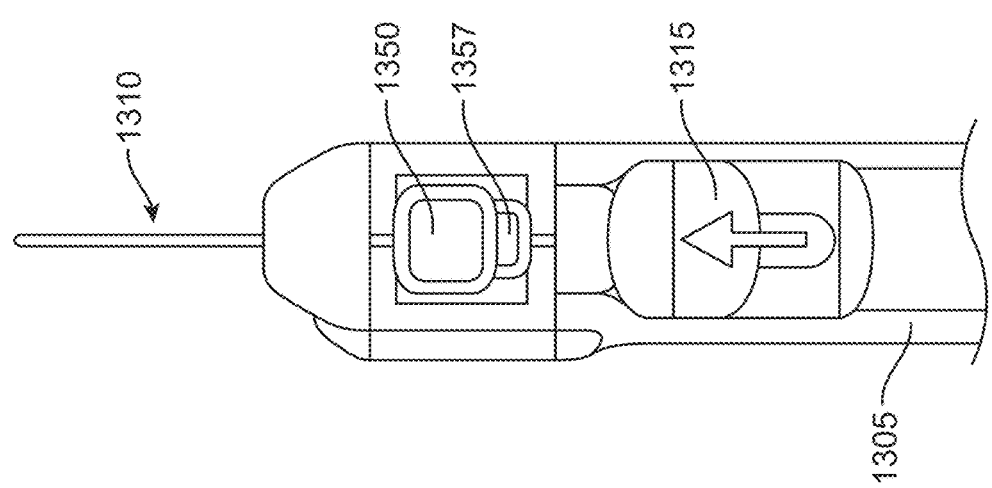

In an example embodiment, the cutting member 312 is attached to a cover 314 that is movable relative to the handle 305 (see FIGS. 3-4). The cover 314 can be coupled to a distal end region of the handle 305 by a hinge 317 such that the cover 314 can rotate around a pivot axis P of the hinge 317 relative to the handle 305. The cover 314 can be lifted to pivot into an open configuration (see FIG. 3) revealing a recess 321 within which a patch of material 101 can be positioned and held fixed relative to the handle. When the cover 314 is rotated back around the pivot axis P into the closed configuration, the patch of material 101 positioned within the recess 321 is compressed and/or tensioned between the cover 314 and the handle 305. The compression and/or tension of the patch of material 101 can help to assure a clean and complete cut of the material. In some implementations, the patch of material 101 is placed under tension such as by outward stretching by the cover 314 prior to cutting with the cutting member 312. The patch of material 101 may be stretched outward from the cutting locations as shown in FIGS. 15A-15C.

The recess 321 can be within a proximal portion of the instrument such as with a portion of the handle 305. The recess 321 for holding the patch of material 101 may also be a recess within a cartridge removably coupled to a portion of the instrument, such as within a region of the handle 305 or coupled to a distal portion of the instrument.

It should be appreciated that tensioning the patch can include activating a separate actuator to tension the patch. Tensioning can also be achieved during the stabilization and compression step without a separate actuation. For example, closing the cover 314 alone may result in both compression and tensioning of the patch of material without a separate actuator to provide the tension on the patch of material after compression.

The cover 314 can open along any of a number or orientations relative to the handle. For example, the pivot axis P of the hinge 317 can be substantially orthogonal to the longitudinal axis of the handle A. In this implementation, the hinge 317 can be positioned on a distal end of the handle 305 between the shaft and the cover 314 such that the cover 314 hinges open by rotating upward and toward the shaft (see, e.g., FIGS. 3 and 4). Alternatively, the hinge 317 can be positioned such that the cover 314 hinges open by rotating upward and toward the proximal end region of the handle 305 (see, e.g., FIGS. 5 and 6A-6B) In still other implementations, the hinge 317 can be positioned on a side of the handle 305 such that the pivot axis P and the longitudinal axis A are substantially parallel with one another. In this implementation, the cover 314 can swing outward away from the longitudinal axis A of the handle 305 (see, e.g., FIGS. 15A-15C). Any of a variety of configurations are considered herein.

The cutting member 312 can extend from a lower surface of the cover 314 to cut the patch of material 101 (e.g. bio-tissue) in a guillotine type manner. FIG. 4 shows the cover 314 in an open configuration raised away from the recess 321 within which a patch of material 101 is positioned. The cutting member 312 can extend from a lower surface of the cover 314 such that its cutting surface penetrates the patch of material 101. In some implementations, the cutting member 312 is coupled to a movable actuator or push-button 313 that can be actuated to move the cutting member 312 from a sheathed configuration towards a cutting configuration. Once the cover 314 is in a closed configuration compressing and/or stretching the patch of material 101 between the lower surface of the cover 314 and the housing 305, the movable actuator 313 may be urged downward relative to the cover 314 placing the cutting member 312 into a cutting configuration. The cutting member 312 can extend below the lower surface of the cover 314 and slice through the patch of material 101 held within the recess 321. One of more return springs 323 can urge the actuator 313 back upward such that the cutting member 312 is once again in the sheathed configuration. The cutting member 312 cuts the patch of material into an implant as the cutting member moves towards the cutting configuration. The implant, once cut, is also axially aligned with the lumen of the shaft.

It should be appreciated that other types of cutting mechanisms can be used. For example, lowering of the cover 314 may also cut the patch of material 101 held within the recess 321 in a rotating type cutting motion. In this implementation, the cutting member 312 extends below the plane of the lower surface of the cover 314 such that the blade edges are available to cut the patch of material 101 upon rotating the cover 314 into the closed configuration. Alternatively, the cutting motion may be an axial cutting motion with a slidable cutting tube such that trephination occurs along the implantation conduit as opposed to a cutting motion orthogonal to the plane of the patch of material 101.

As mentioned above, as the cutting member moves towards the cutting configuration it cuts the patch of material into an implant. The implant, once cut, is also axially aligned with the lumen of the shaft for deployment into the eye. Thus, motion of the cutting member 312 simultaneously cuts the stent and places the cut stent into a position relative to the shaft 310 such that the stent can be delivered through the shaft 310. The cutting member 312 in order to cut the patch of material 101 into a rectangular stent shape can include a pair of blades separated by a spacer. The spacer between the pair of blades can engage with the cut stent 105 following cutting by the blades to urge the stent 105 downward through a slot in the outer tube 318. The pusher 320 can be in a fully retracted configuration via the knob 311 such that the lumen of the outer tube 318 is free to accept the cut stent 105 through the slot. It should be appreciated that the stent 105 may be urged downward into a position relative to the delivery device that aligns the stent 105 with the path of implantation while not specifically loaded into the lumen of the outer tube 318. For example, loading into the lumen of the outer tube 318 can occur upon an additional step such as advancement of the stent 105 towards the lumen of the outer tube 318 following cutting. A variety of sheath loading configurations is considered herein, including top-loading as described above, front-loading, rear-loading, and side-loading, which will be described in more detail below. Regardless of the configuration, the trephination of the patch of material 101 can place the stent 105 in a position (i.e. axially aligned with the lumen of the shaft) that allows for it to be deployed into the eye without necessitating manual tissue transfer of the tiny piece of cut material.

FIG. 5 shows another implementation of a delivery device 110. This implementation has a detachable trephination cartridge 205 close to the tip of the delivery device 110. This implementation reduces or minimizes a travel distance of the stent 105 once the stent has been formed within the lumen of the shaft 310.

As with the previous implementation shown in FIGS. 3 and 4, the delivery device 110 can include a proximal handle 305 having one or more actuators 315 and a shaft 310 extending from a distal end region of the handle 305. The actuators 315 can include a first and second slider configured to move the outer sheath and the pusher of the shaft 310, respectively. It should be appreciated that the device 110 need not incorporate multiple actuators 315 to achieve motion of multiple components. For example, the device 110 can include a single actuator 315 configured to cut and deploy the stent 105, for example by causing motion of both the outer sheath and pusher based on, for example, the degree of actuation of the slider.

The trephination cartridge 205 can include a base 324 and a cover 314 movably attached to the base 324. The cover 314 and base 324 can be coupled together by a hinge 317 such that the cover 314 rotates around a pivot axis of the hinge 317. As with the previous implementation, the cover 314 can be lifted to pivot into an open configuration revealing a recess 321 of the base 324 within which a patch of material can be positioned and held fixed. When the cover 314 is rotated back around into the closed configuration, the patch is compressed and/or tensioned between the cover 314 and the base 324. The cover 314 and base 324 need not be hinged relative to one another. For example, the cover 314 and base 324 can simply uncouple revealing the upper surface of the base 324 such that the shaft 310 and patch of material 101 can be positioned appropriately relative to the trephination cartridge 205. The cover 314 can be configured to additionally apply an amount of tension on the patch of material 101, such as stretching in an outward direction from the center of the patch of material 101 to improve cutting.

FIG. 6A shows the delivery device 110 having a trephination cartridge 205 coupled to a distal end region of the handle 305 in a closed configuration in which an upper surface of the base 324 and a lower surface of the cover 314 of the trephination cartridge 205 are opposed against one another. FIG. 6B is a cross-sectional view of the device 110 in FIG. 6A illustrating the shaft 310 extending through the handle 305.

The trephination cartridge 205 can be provided pre-loaded with a patch of material positioned within the recess. For example, the patch of material can be compressed and/or tensioned within the base 324 and cover 314. The cutting member 312 can then be actuated to punch out a stent 105 from the patch of material, for example, by pressing down on the push-button 313 to urge the cutting member 312 through the patch of material held within the trephination cartridge 205. The delivery device 110 and trephination cartridge 205 can then be engaged to each other. For example, the shaft 310 can insert through a proximal port on the trephination cartridge 205 thereby front-loading the cut stent 105 into the outer tube 318 for delivery into an eye. The cut stent 105 can be held fixed within the trephination cartridge 205. In still further implementations, the stent can be loaded into a cutout opening in the shaft from above, or front-loaded, or from a rear of the shaft.

It should be appreciated that the patch of material need not be cut into the stent by a user at the time of implantation into a subject. The patch of material may be cut into the stent well before the time of implantation, such as at the tissue bank or tissue engineering lab. The stent can be provided as a pre-cut, pre-loaded stent within a cartridge configured to couple with the delivery device. For example, the trephination cartridge 205 can be provided to a user pre-loaded with a pre-cut stent 105 from the patch of biologically-derived material. The cartridge 205 holding the stent 105 can be coupled with the delivery device at the time of implantation. Once coupled together, a user can load the stent 105 into the shaft 310 of the delivery device as described elsewhere herein. In still further implementations, the stent 105 can be provided to a user pre-loaded within the lumen of shaft 310. The patch of material can be provided in the cartridge or in the lumen of the shaft 310 emerged in an appropriate tissue preservative media as is known in the art.

Figure 7:
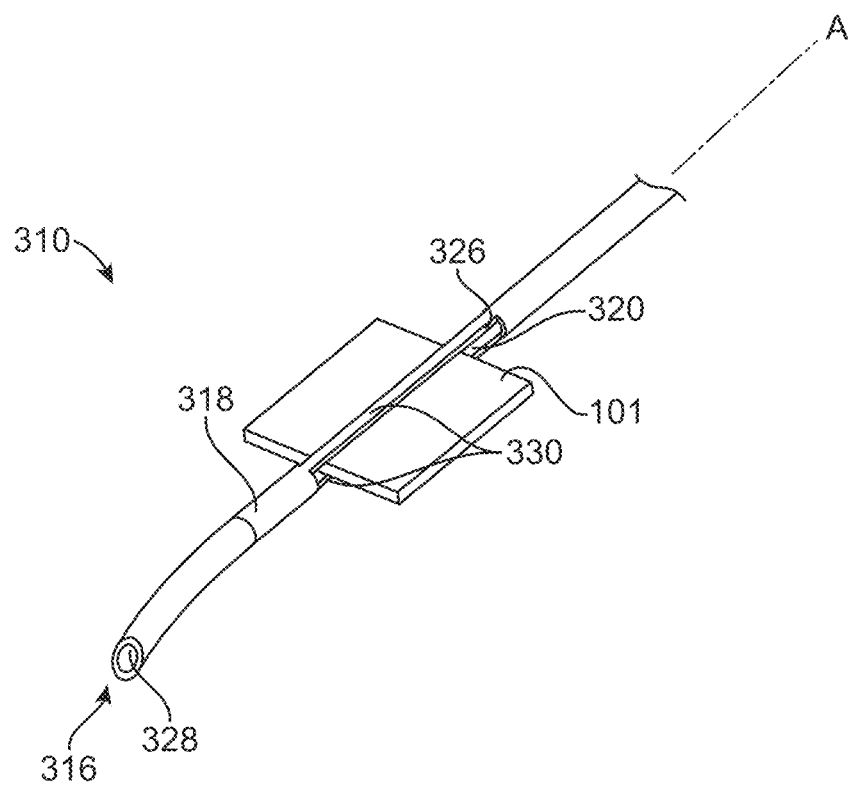
FIG. 7 shows a partial view of a delivery device shaft having a patch of biologically-derived material extending through cut-out windows.
Figure 8A:
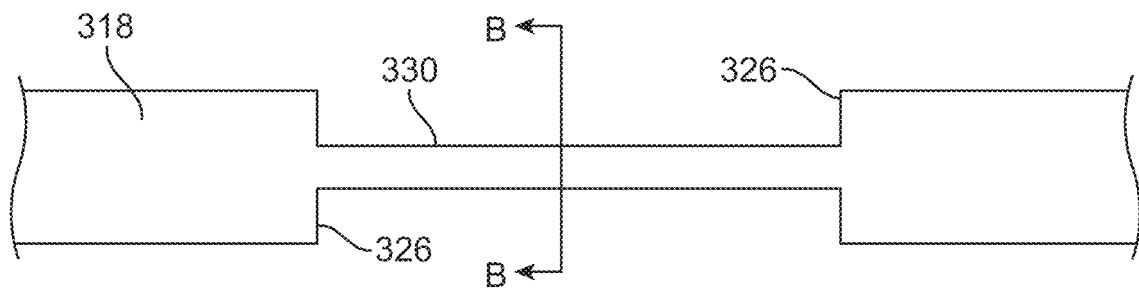
FIG. 8A is a top-down schematic view of the cut-out windows of a delivery device shaft.
Figure 8B:
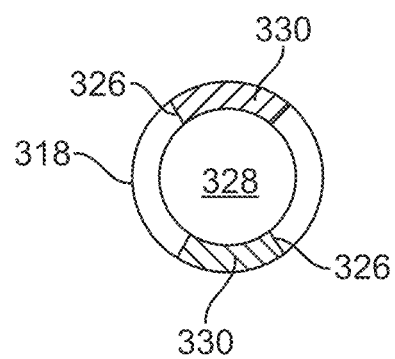
FIG. 8B is a cross-sectional view of FIG. 8A taken along line B-B.

In an implementation, the user can manually load a patch of material 101 through opposing cut-out windows 326 extending through the outer tube 318 of the shaft 310 of the delivery device 110 (see FIG. 7). The cut-out windows 326 in the outer tube 318 can extend through opposing sidewalls such that the patch of material 101 can be inserted through a first cut-out window 326, traverse the lumen 328 of the outer tube 318, and insert through the second cut-out window 326 on the opposite side of the lumen 328. The dimensions of the cut-out 326 are sufficient to load the patch of material 101 through the cut-out 326 as shown in FIG. 7. The patch of material 101 can have a dimension that is wider than an outer diameter of the outer tube 318 such that each side of the patch 101 extends beyond the sidewalls of the outer tube 318. The cut-out windows 326 in the outer tube 318 can each have a length along the longitudinal axis A of the shaft 310 that is at least as long as a length of the patch of material 101. The cut-out windows 326 in the outer tube 318 can have a depth that is at least as thick as the thickness of the patch of material 101. FIG. 8A is a top-down schematic view of the cut-out windows 326 of the shaft 310. FIG. 8B is a cross-sectional view of FIG. 8A taken along line B-B. The cut-out windows 326, which can be created by removing a side wall on either side of the outer tube 318), form narrow webs 330 on an upper and lower surface of the tube 318.

Figure 9A:
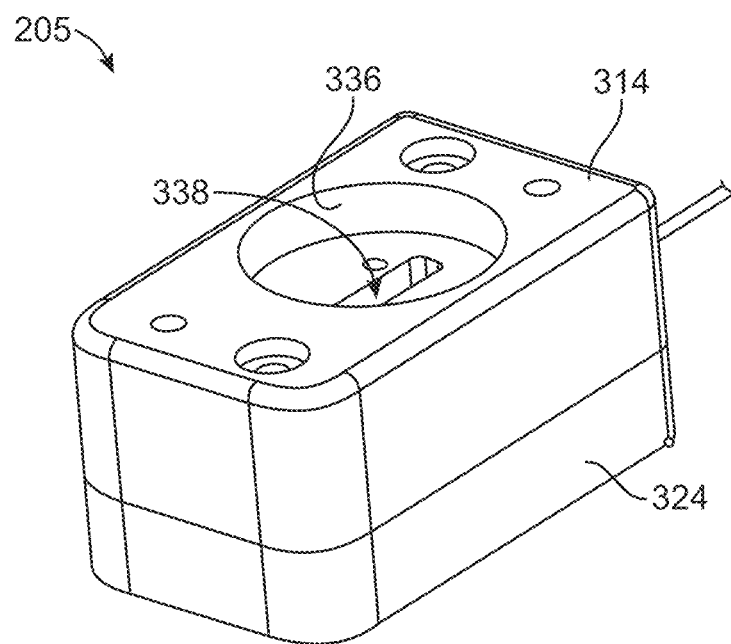
FIG. 9A is a perspective view of an implementation of a trephination cartridge.
Figure 9B:
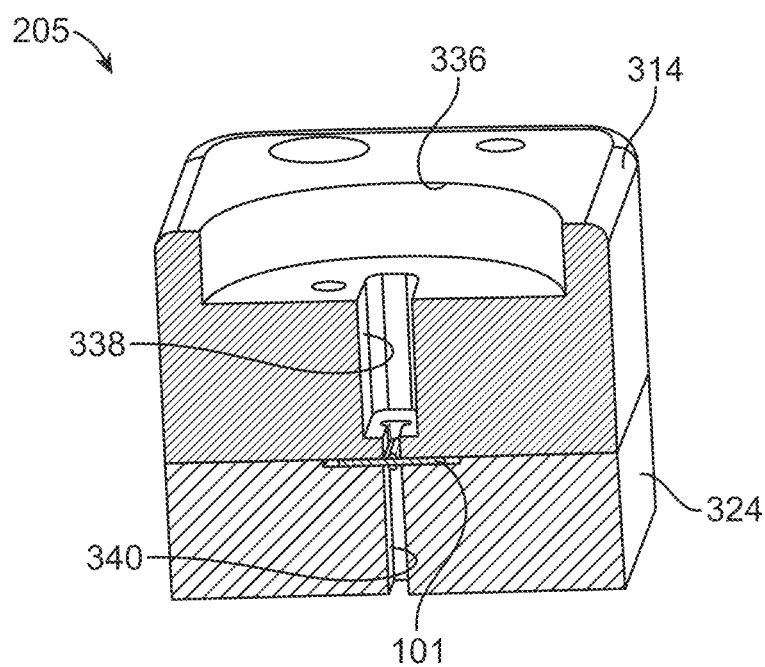
FIG. 9B is a cross-sectional view of the trephination cartridge of FIG. 9A.
Figure 9C:
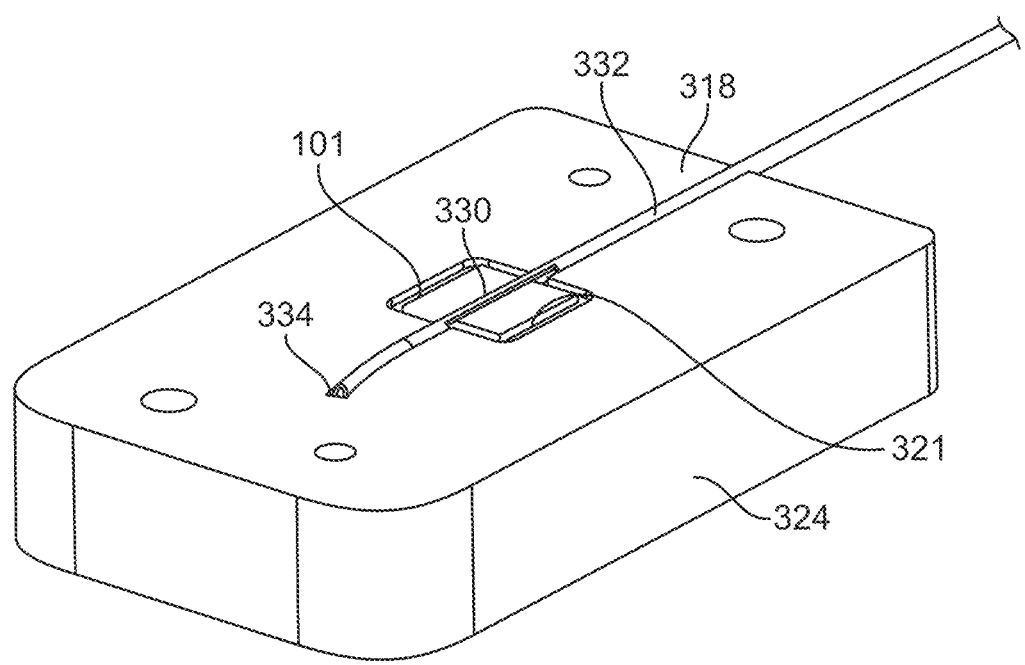
FIG. 9C is a perspective view of the base of the trephination cartridge of FIG. 9A.

FIGS. 9A-9B show another implementation of a trephination cartridge 205 having a cover 314 and a base 324. FIG. 9A shows the base 324 with the top cover 314 installed. FIG. 9B is a cross-sectional view of the cartridge 205 showing the tissue patch 101 sandwiched between the base 324 and the cover 314. FIG. 9C shows the base 324 of the trephination cartridge 205 loaded with a patch of material 101 loaded within the cut-out windows 326 of the tube 318 and positioned within the recess 321 of the base 324. The recess 321 can be positioned between a proximal slot 332 and a distal slot 334. The proximal slot 332 is sized to receive at least a portion of the outer tube 318 located proximal to the cut-out windows 326 and the distal slot 334 is sized to receive the portion of the outer tube 318 located distal to the cut-out windows 326. The recess 321 can have any of a variety shapes, but is generally sized to receive the patch of material 101 loaded within the cut-out windows 326 of the outer tube 318. Thus, when the shaft 310 of the delivery device 110 is inserted into the trephination cartridge 205, the shaft 310 is received within the proximal and distal slots 332, 334 and the tissue patch 101 sits within the recess 321.

Still with respect to FIGS. 9A-9C, the cover 314 can have an upper surface forming an external surface of the cartridge 205. The cover 314 can also include a lower surface configured to engage with an upper surface the cartridge base 324. The upper surface can include a recess 336 within which is an entrance to a bore 338 extending from the upper surface through a full thickness of the cover 314 to the lower surface. The upper surface of the cartridge base 324 includes an entrance to a bore 340 extending through at least a thickness of the base 324. The bore 340 of the base 324 can, but need not extend through the full thickness of the base 324. When the cover 314 abuts the base 324, the bores 338, 340 are aligned such that a contiguous channel is formed. The contiguous channel is sized and shaped to receive the cutting member 312, which will be described in more detail below. The cutting member 312 can translate relative to the cartridge 205 and extend from the upper surface of the cover 314 through the full thickness of the cover 314 into the bore 340 of the base 324.

The lower surface of the cover 314 surrounding the bore 338 in the cover 314 and the upper surface of the base 324 surrounding the bore 340 in the base 324 can compress the patch of material 101 positioned therebetween. The recess 321 in the base 324 can have a depth that is less than a thickness of the patch 101 positioned within the recess 321 such that when the cover 314 is coupled to the base 324, the patch of material 101 is compressed between the cover 314 and base 324. The compression of the patch of material 101 between the base 324 and the cover 314 helps to prevent movement of the patch of material 101 during cutting with the cutting member 312. Tension can also be applied to the patch of material 101 prior to cutting. In some implementations, the cover 314 is hinged relative to the base 324 (see FIG. 5). The cover 314 and base 324 can be reversibly fixed to one another such that upon closing the cover 314 onto the base 324, the cover 314 latches or otherwise reversibly couples to the base 324 to prevent inadvertent opening of the cover 314 relative to the base 324.

Figure 10A:
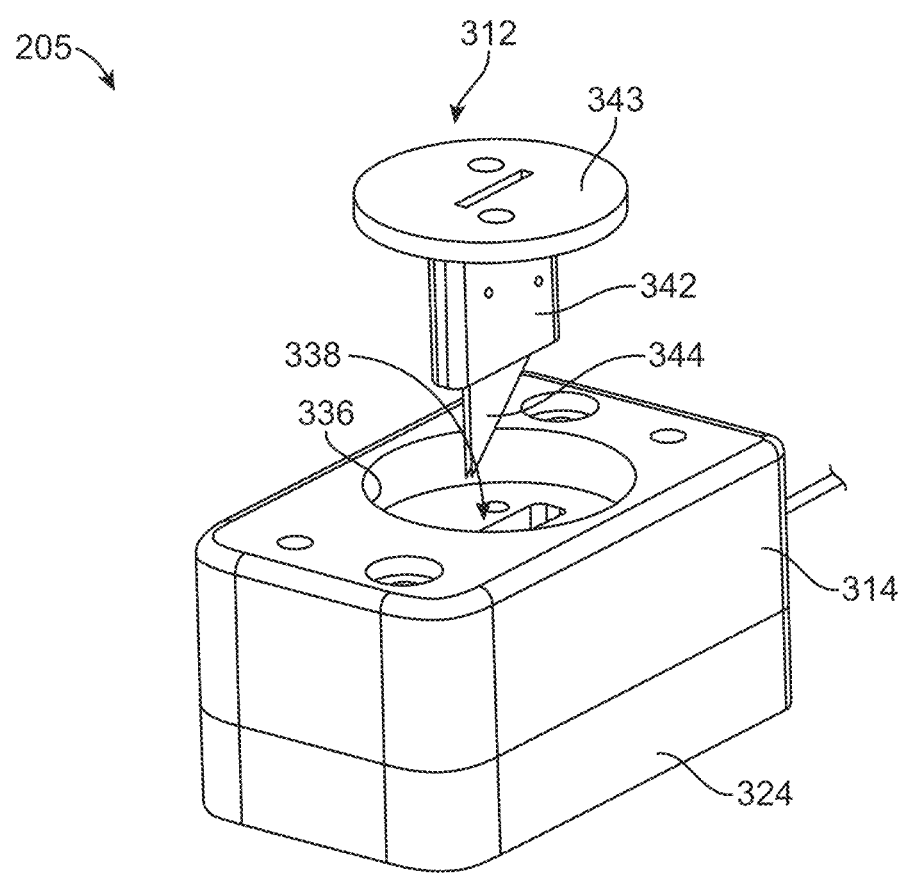
FIG. 10A is a perspective view of the trephination cartridge of FIG. 9A relative to a cutting member.
Figure 10B:
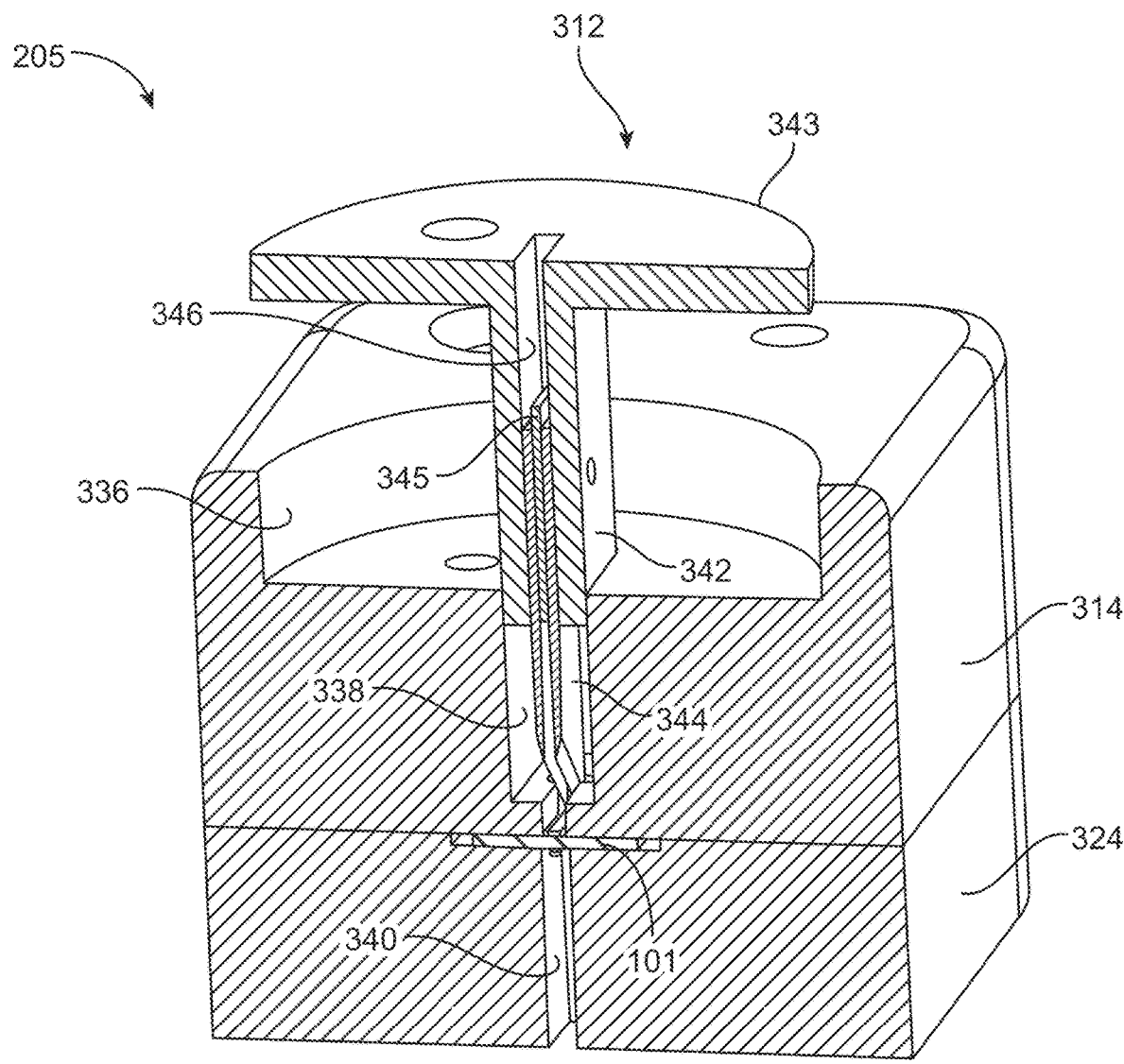
FIG. 10B is a cross-sectional view of the trephination cartridge of FIG. 10A with the cutting member partially inserted.
Figure 10C:
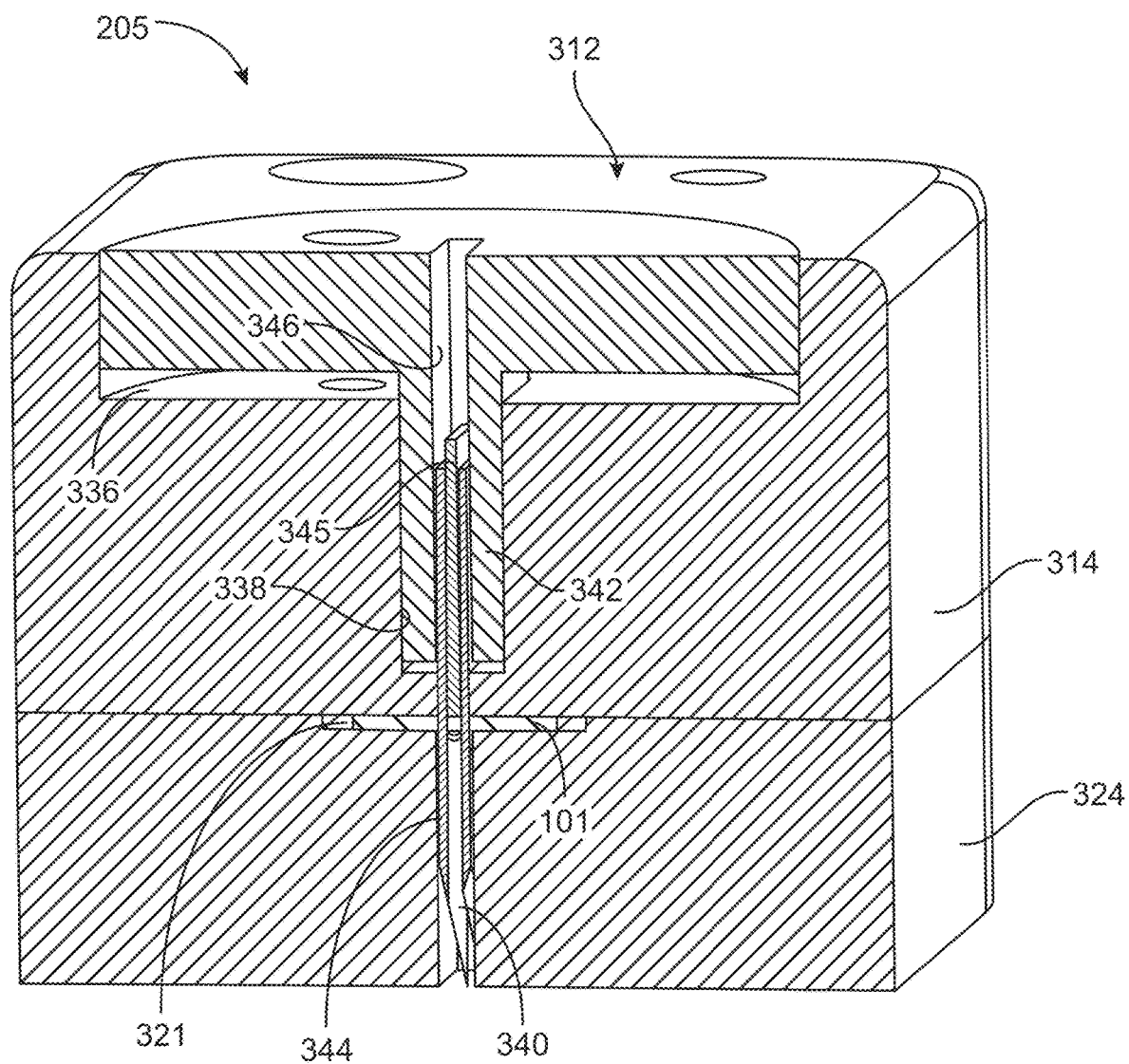
FIG. 10C is a cross-sectional view of the trephination cartridge of FIG. 10A with the cutting member fully inserted.

FIG. 10A illustrates the trephination cartridge 205 with the base 324 and cover 314 in a closed configuration. FIG. 10B is a cross-sectional view of the trephination cartridge 205 in a closed configuration with the patch of material 101 sandwiched between the cover 314 and base 324 and the cutting member 312 inserted into the bore 338 of the cover 314. FIG. 10C is a cross-sectional view of the trephination cartridge 205 with the cutting member 312 advanced fully through the cover 314 and into the bore 340 of the base 324.

The cutting member 312 can include a pair of blades 344 and an enlarged grip feature or handle 343. The handle 343 is positioned on an upper end of the blade housing 342 whereas the pair of blades 344 project from a lower end of the blade housing 342. The handle 343 can be shaped and sized for a user to comfortably grip the cutting member 312. FIGS. 10A-10C illustrates the handle 343 as having a disc shape configured to be received within the correspondingly shaped recess 336 in the upper surface of the cover 314. Any of a variety of shapes are considered herein.

The blade housing 342 can include a central channel 346 within which an upper portion of the blades 344 are received. The lower cutting surfaces of the blades 344 extend below the blade housing 342. The pair of blades 344 can be separated from one another by a spacer 345 defining a gap between the blades 344. The gap size is selected based on the desired width of the stent 105 to be achieved upon cutting the patch of tissue 101 with the blades 344.

The cutting member 312 can be received within the recess 336 in the cover 314 such that the blades 344 extending from a lower end of the cutting member 312 insert first through the bore 338 in the cover 314 followed by the blade housing 342 (see FIG. 10A). Thus, the bore 338 of the cover 314 can be sized and shaped to receive not just the blades 344, but also at least a portion of the blade housing 342. The handle 343 can be sized and shaped to be received within the recess 336 in the cover upon full insertion of the cutting member 312 within the cartridge 205.

The tissue patch held within the cut-out region of the shaft is cut in two locations creating a narrow strip of material (i.e. the stent 105) from the patch of material 101. As the cutting member 312 is urged further through the bore 338 in the cover 314, the blades 344 are urged towards the patch of material 101 compressed between the cover 314 and the base 324 (see FIG. 10B). As the cutter is urged further through bore 338 of the cover 314 and enters bore 340 of the base 324, the blades 344 slice through the patch of tissue 101 positioned within the recess 321 (see FIG. 10C). The blades 344 make two cuts in the patch of material 101 as it extends down through bore 340 of the base 324 completely cutting through the patch 101 forming a stent 105. Motion of the cutter towards the cutting configuration cuts the patch of material into the stent as the cutting member moved towards the cutting configuration and the stent, once cut, is axially aligned with the lumen 328 of the outer tube 318. The stent 105 that is formed is thereby already loaded relative to or within the lumen 328 of the outer tube 318 such that no loading step is necessary.

The blades 344 have inserted through the contiguous channel formed by the bores 338, 340 of the cover 314 and the base 324. The housing 342 can seat within the bore 338 and/or the handle 343 can seat within the recess 336 of the cover 314 thereby preventing any further downward motion of the blades 344. The stent 105 that is formed is held snugly within the lumen 328 of the outer tube 318. As mentioned above, the outer tube 318 of the delivery device shaft 310 can include a pair of cut-out windows 326 on opposing sidewalls creating narrow webs 330 on an upper and lower surface of the tube 318. As best shown in FIGS. 11A-11E, each of the blades 344 is received within a respective cut-out window 326 of the tube 318 when the cutting member 312 is inserted within the cartridge 205 so that the blades 344 extend into the bore 340 in the base 324. The gap between the pair of blades 344 is sized to accommodate and receive the webs 330 as the blades 344 slide past the shaft 318 positioned within the cartridge 205. The stent 105 once cut is contained within the lumen 328 of the outer tube 318 at the location of the cut-out windows 326 with one of the pair of blades 344 enclosing the stent 105 on a first side and a second of the pair of blades 344 enclosing the stent 105 on a second opposite side. The enclosure creates the path for the stent 105 to be deployed from lumen 328 out the distal end of the shaft 310, which will be described in more detail below.

Still with respect to FIGS. 11A-11E, the blades 344 can include single bevel edges that are angled to propagate the cut, similar to scissors. It is preferred that the blades 344 not chop tissue. The blades 344 are positioned relative to the cartridge 205 such that a complete cut through the patch 101 occurs upon full travel of the cutting member 312 through the cartridge 205.

Upon complete translation of the cutting member 312 into the cover 314 (i.e., placement of the cutting member 312 into the cutting configuration), the blade housing 342 is constrained within the bore 338 in the cover 314. Thus, a length of the blade housing 342 is no longer than and preferably slightly shorter than a depth of the bore 338 in the cover 314. In some implementations and as best shown in FIG. 10B, the distal exit from the bore 338 at the lower surface of the cover 314 can have a smaller dimension than the entrance to the bore 338. Where the entrance to the bore 338 is sized to receive the blade housing 342, the exit from the bore 338 may be sized to receive only the blades 344 and not the blade housing 342. This arrangement can prevent over-insertion of the cutting member 312 relative to the cartridge 205 in that the lower end region of the bore 338 acts as a stop for the blade housing 342.

The cutting member 312 can additionally include a safety sheath (not shown) configured to enclose the dual blades 344 extending from a lower end of the blade housing 342. The safety sheath can prevent inadvertent damage to the blades 344 or the user when the cutting member 312 is not engaged with the cartridge 205. For example, the safety sheath can enclose the blades 344 on all but a lower end of the cutting member 312. The cover 314 and base 324 of the cartridge 205 can include additional channels aligned, sized and shaped to receive the safety sheath surrounding the blades 344 as the cutting member 312 is inserted into the cartridge 205.

Figure 11A:
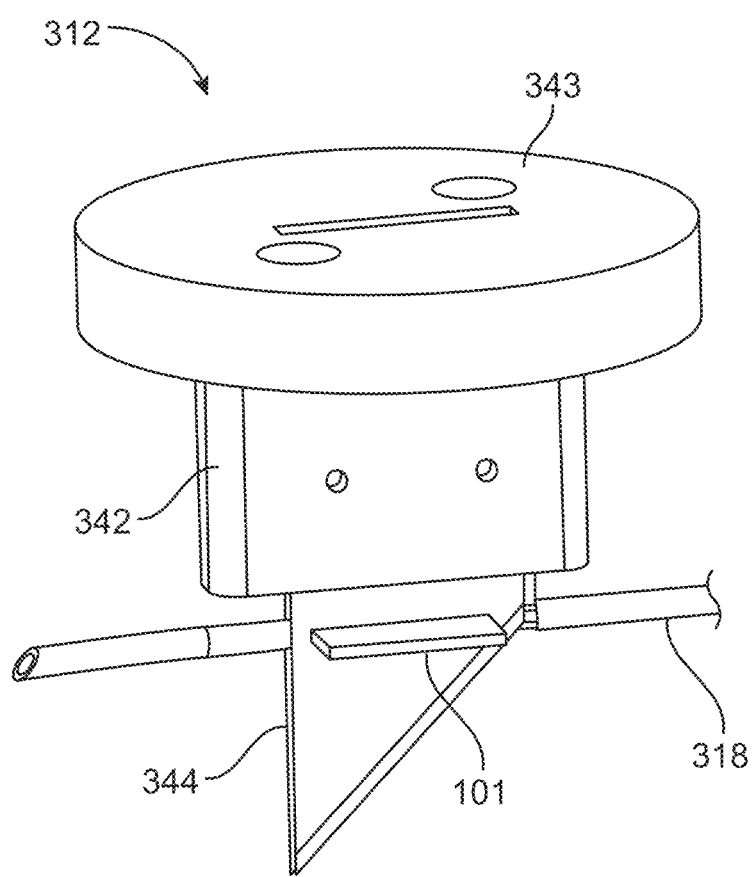
FIG. 11A is a side view of the cutting member of FIG. 9A showing the blades relative to a delivery device shaft loaded with a patch of biologically-derived material.
Figure 11B:
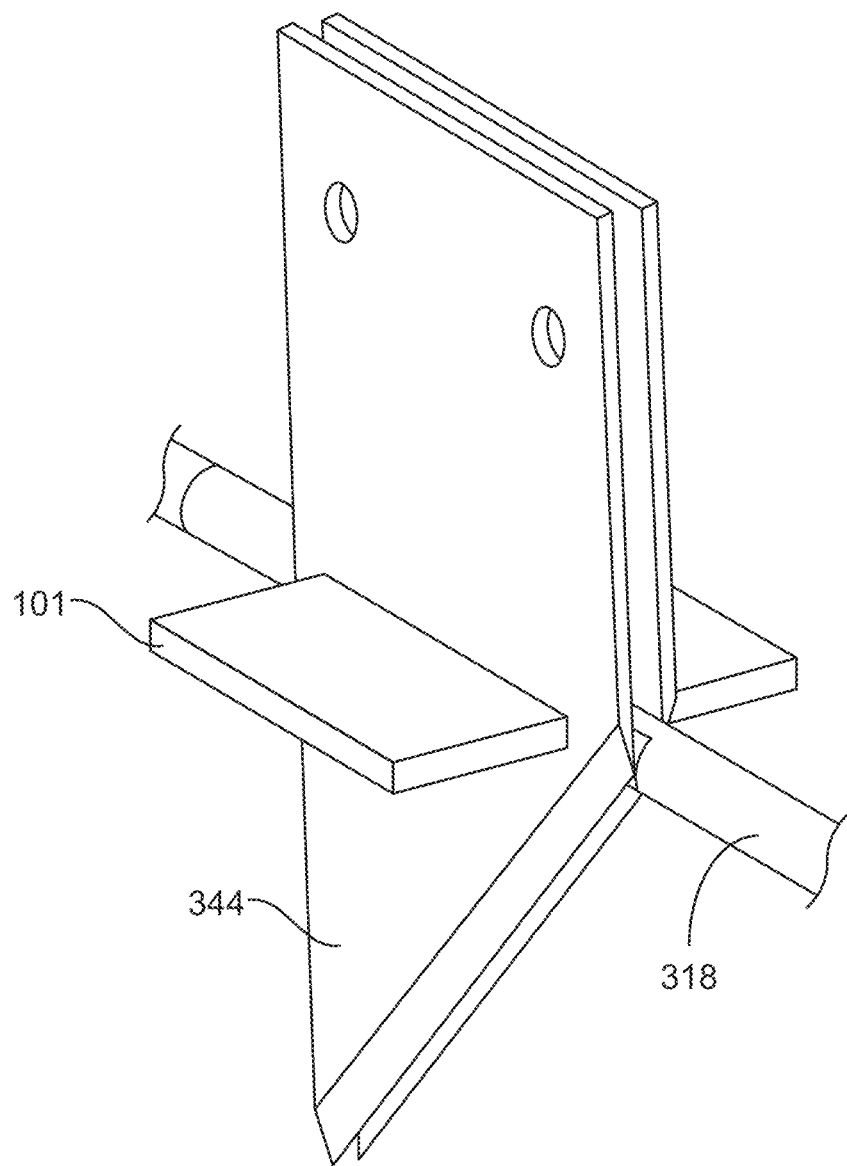
FIG. 11B is a perspective view of the cutting member of FIG. 11A with the housing removed.
Figure 11C:
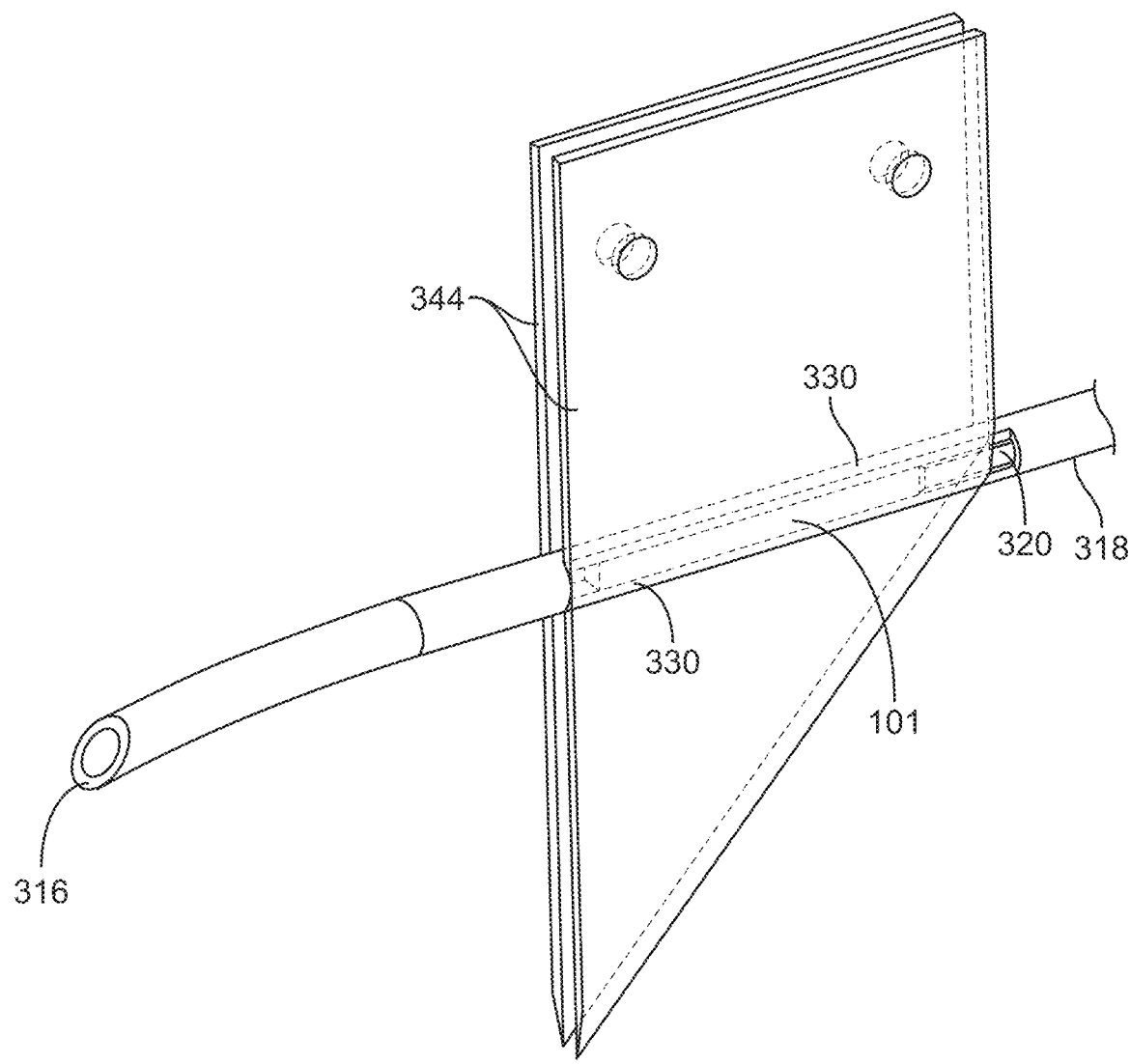
FIG. 11C is a side view of the blades relative to the delivery device shaft and cut stent.
Figure 11D:
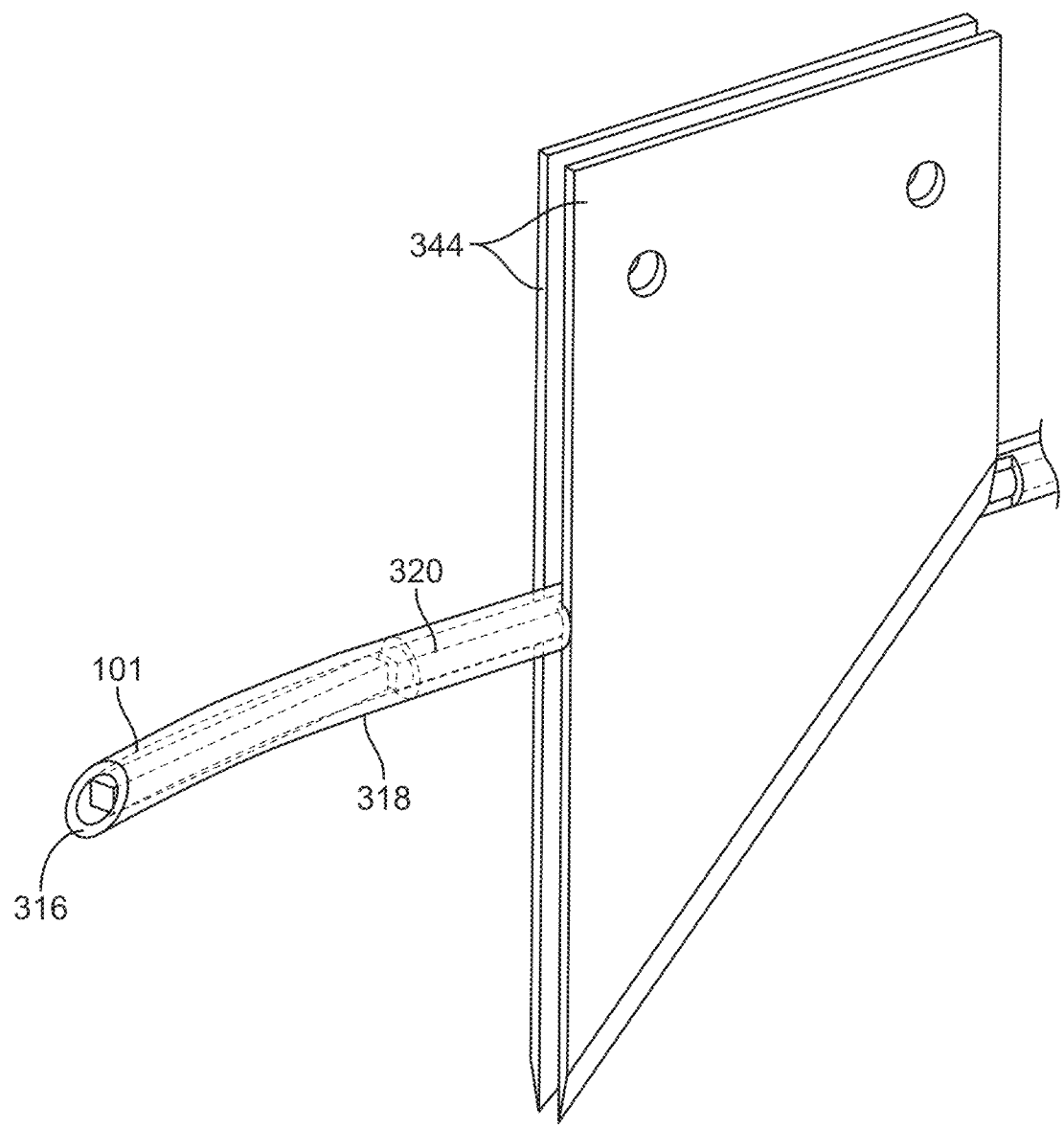
FIG. 11D shows a side view of the cut stent primed within the lumen of the delivery device shaft.
Figure 11E:
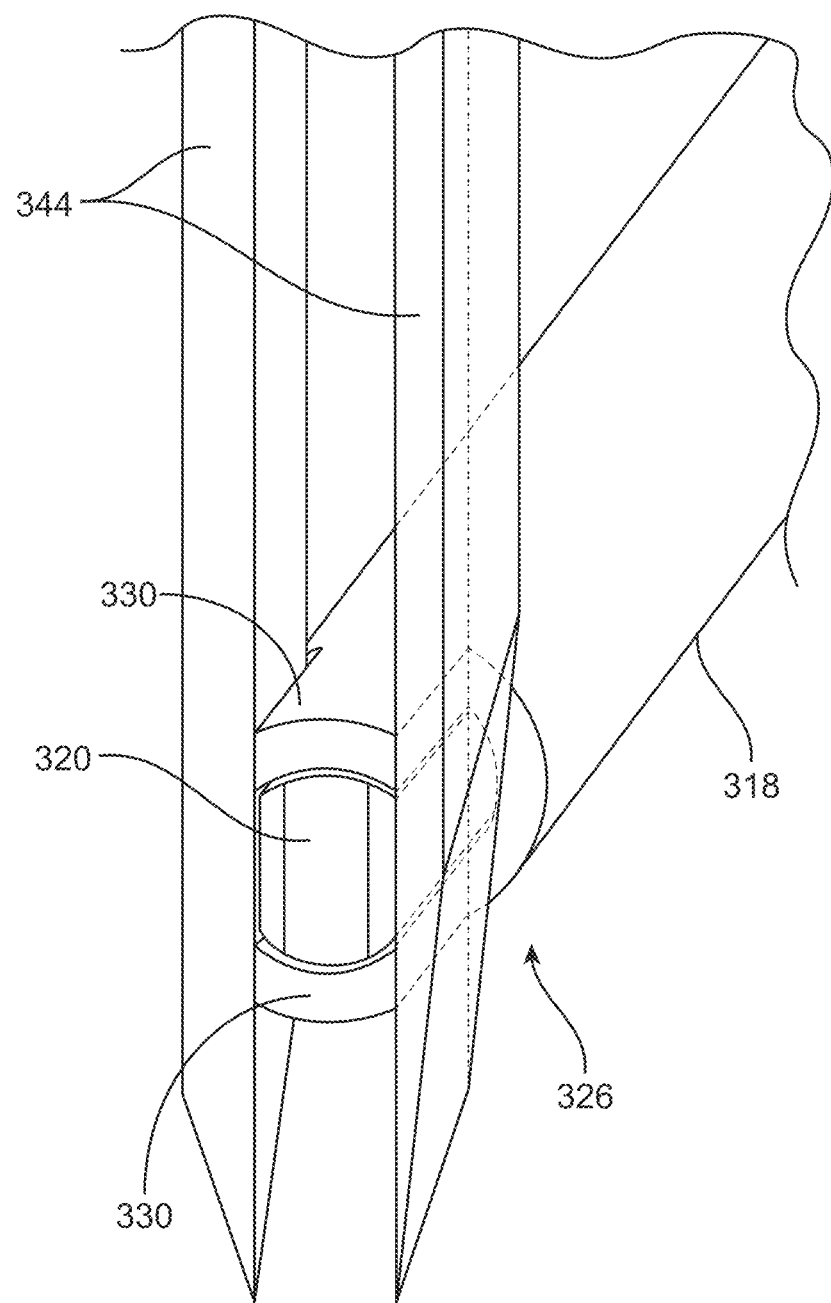
FIG. 11E is a distal end view of the delivery device shaft having a tubular outer sheath and an inner elongate member or pusher.

FIG. 11E shows a cross-sectional view of the cut-out windows 326 of the outer tube 318 with the blades 344 positioned on either side of the upper and lower webs 330. As mentioned, the shaft 310 of the delivery device 110 can include a pusher 320 positioned within the lumen 328 of the outer tube 318. At least a portion of the pusher 320 can have a cross-sectional shape configured to slide past the blades 344 positioned within the cut-out windows 326 of the tube 318. The cross-sectional shape of at least a portion of the pusher 320 can incorporate flat sides configured to align with the cut-out windows 326 upon extension of the pusher 320 relative to the outer tube 318 during deployment of the stent 105 from the lumen 328. The flat sides of the pusher 320 (as opposed to convex sides) can define a width that is sized to slide between the two blades 344 positioned within the cut-out windows 326. Like the stent, at least a portion of the pusher 320 can be sized to completely fill at least a portion of the lumen 328 of the outer tube 318. The outer tube 318 can be a hypotube that is no greater than about 18 G (0.050" OD, 0.033" ID), 20 G (0.036" OD, 0.023" ID), 21 G (0.032" OD, 0.020" ID), 22 G (0.028" OD, 0.016" ID), 23 G (0.025" OD, 0.013" ID), 25 G (0.020" OD, 0.010" ID), 27 G (0.016" OD, 0.008" ID), 30 G (0.012" OD, 0.006" ID), or 32 G (0.009" OD, 0.004" ID). In some implementations, the outer tube 318 is a hypotube having an inner diameter that is less than about 0.036" down to about 0.009". The dimensions of the outer tube 318 can be selected based on the dimensions desired for the stent to be implanted as discussed in more detail above.

While the shaft 310 of the delivery device 110 is installed in the cartridge 205 and the blades 344 are still positioned in the cutting configuration, the pusher 320 can be pushed distally away from the handle 305 of the delivery device 110 to position the stent 105 cut from the patch of material 101 into a primed position within the lumen 328. In some implementations, the pusher 320 can be advanced distally relative to the handle 305, for example, using an actuator 315 on the handle 305. The presence of the blades 344 on either side of the cut-out windows 326 and the webs 330 on the upper and lower sides prevents the stent 105 from buckling within the lumen 328 during this priming step. The conduit within which the stent 105 is held is size-matched to the outer dimension of the stent being implanted thereby preventing buckling and wrinkling as the stent 105 is urged into the primed position.

Once the stent 105 is urged into the distal tip region of the outer tube 318, the blades 344 can be retracted from the base 324. In some implementations, the cutting member 312 can be removed from the cartridge 205 and the cover 314 opened relative to the base 324 so that the shaft 310 of the delivery device 110 can be removed from the cartridge 205. In other implementations, the cutting member 312 can be withdrawn from the base 324, but still engaged with the cartridge 205 for the shaft 310 of the delivery device 110 to be removed from the cartridge 205. The shaft 310 can be withdrawn from the cartridge 205 with or without the cover 314 being in an open configuration. Once the delivery device 110 and the cartridge 205 are disengaged with one another, the delivery device 110 is ready to be used to insert the stent 105 into the eye, which will be described in more detail below.

Figure 12A:
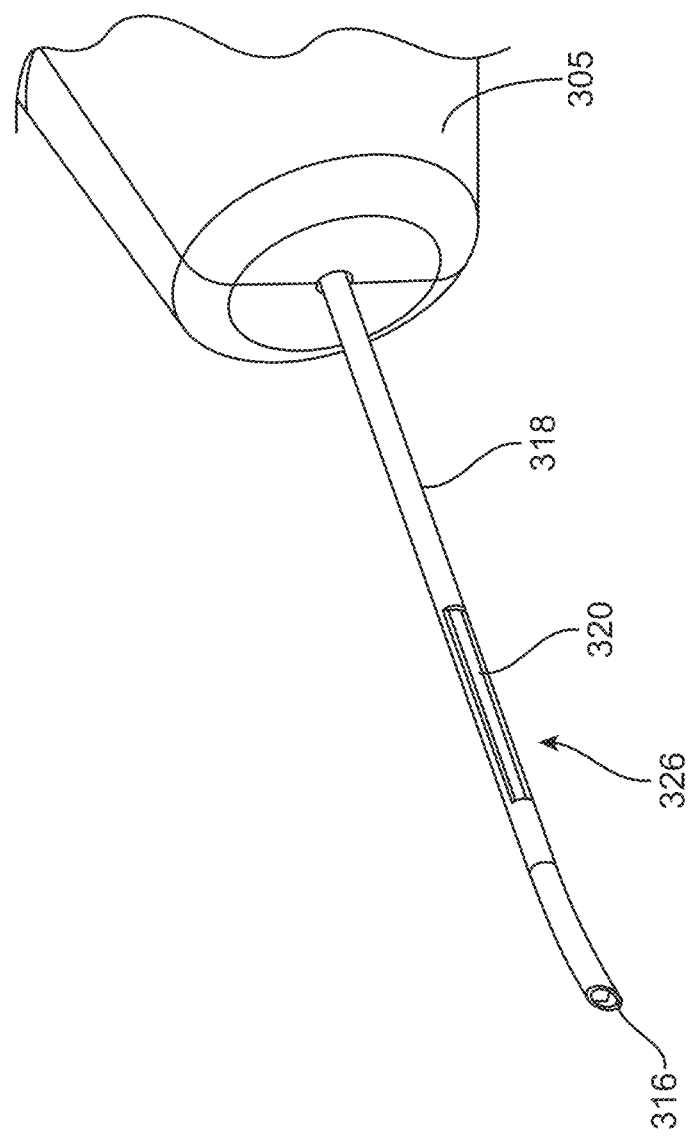
FIGS. 12A-12B illustrate a distal end region of the delivery device.
Figure 12B:
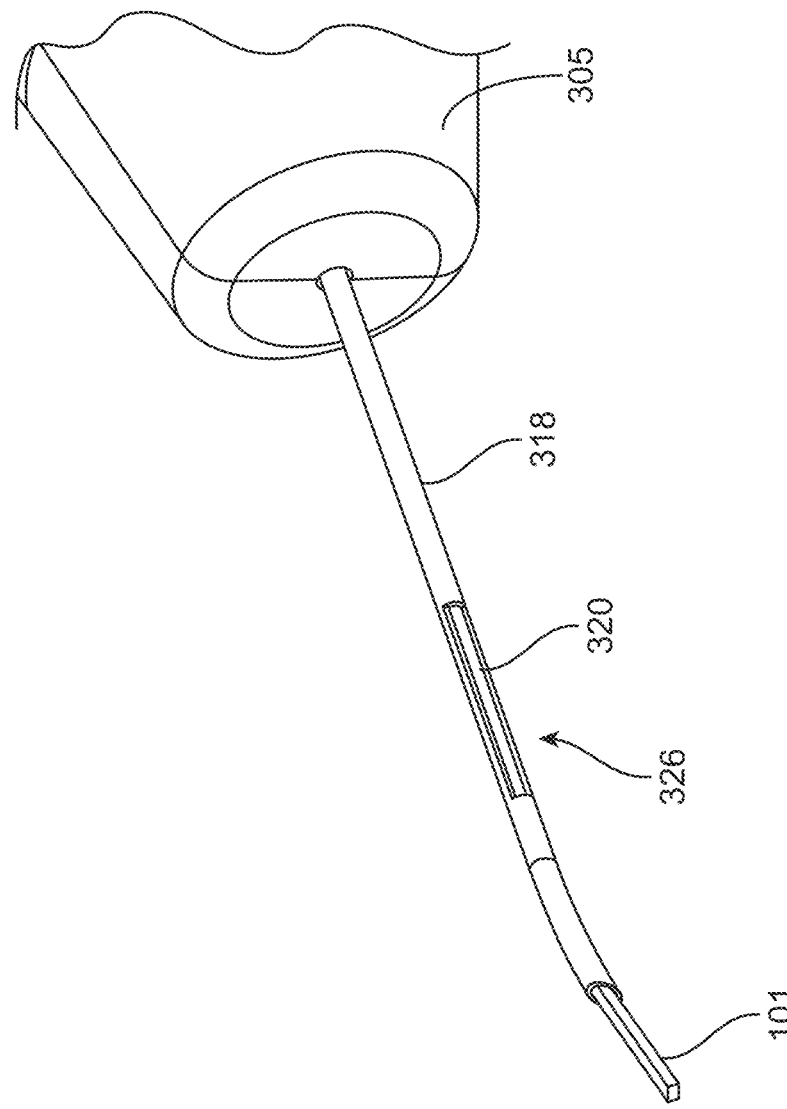

As mentioned above, movement of the components of the delivery device 110 can be achieved using one or more actuators 315 of the handle 305. FIG. 6B is a cross-sectional view of an implementation of the delivery device 110 having its distal shaft 310 engaged with a trephination cartridge 205. The shaft 310 can include a pusher 320 and an outer tube 318. The pusher 320 can be coupled to a first actuator 315 and the outer tube 318 can be coupled to a second actuator 315. Each of the first and second actuators 315 can be sliders configured to advance and retract their respective components. The first actuator 315 can be withdrawn proximally such that the pusher 320 is in its most proximal position relative to the outer tube 318 during cutting of the patch of material 101 compressed and/or tensioned within the cartridge 205. Once the patch of material 101 is cut, the user can advance the first actuator 315 to urge the pusher 320 distally to prime the stent 105 within the lumen 328 of the outer tube 318 towards the distal end of the shaft 310. After the cut stent 105 is primed into its distal position within the lumen 328, the cartridge 205 can be disengaged from the shaft 310. The outer tube 318 of the delivery device 110 can be used to dissect tissue of the eye until a target location is accessed. Once the delivery device is in position to deploy the stent 105 in the eye, the first actuator 315 coupled to the pusher 320 can be maintained in this distal position and the second actuator 315 withdrawn to retract the outer tube 318. This relative movement of the outer tube 318 to the pusher 320 deploys the stent 105 from the lumen 328 in the anatomy (as shown in FIG. 12B). It should be appreciated that additional distal movement of the pusher 320 can be used to aid in deployment of the stent 105 from the lumen 328. It should also be appreciated that pusher 320 advancement and outer tube 318 retraction can be controlled by dual actuators 315 as described above or by a single actuator 315 capable of both pusher and outer sheath movement depending on degree of actuation. Additionally, the shaft 310 of the delivery device 110 can be used to inject viscoelastic during the procedure using the pusher 320 as a plunger.

FIGS. 13A-13B and FIGS. 18A-18B show interrelated implementations of a delivery device 1110 having integrated trephination forming a system for preparing an implant and performing ab interno insertion of the implant into the eye. As described elsewhere herein, the delivery device 1110 can be inserted into the eye and used to implant the stent 105 in the implanted location via an ab interno delivery pathway. The delivery device 1110 can include a proximal portion such as a proximal handle 1305 that is sized and shaped to be grasped by the user and remains outside of a patient's eye. The delivery device 1110 can also include a distal portion. The distal portion can include an elongate delivery shaft 1310 extending distally from the proximal handle 1305. The elongate delivery shaft 1310 includes an outer tube 1318 having a lumen 1328 (see FIG. 14A). An axially movable cutter tube 1312 can be positioned within the handle 1305. A pusher 1320 is shown positioned within the lumen 1378 of the cutter tube 1312. The pusher 1320 is configured to be advanced distally through the lumen 1328 of the outer tube 1318. It should be appreciated that where the delivery devices are described herein as suitable for performing ab interno insertion of an implant that other approaches for implantation are considered as well. For example, the delivery devices may be used to perform a trans-scleral approach for delivery of the implant.

Figure 14B:
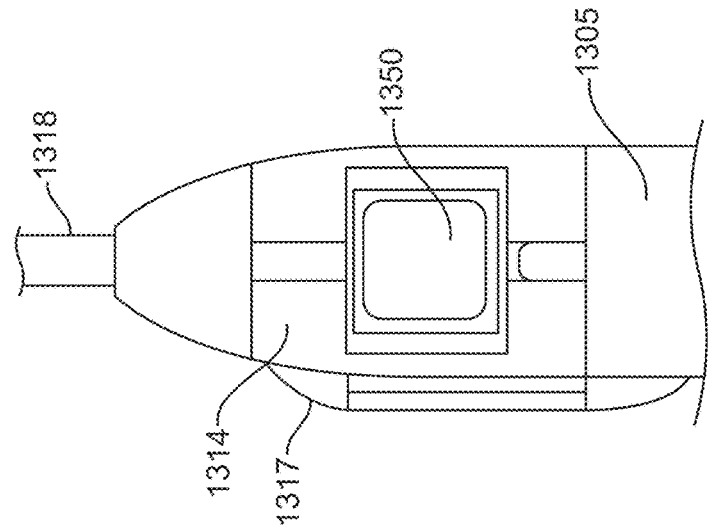
FIGS. 14A-14B are partial views of the delivery device of FIG. 13A.
Figure 14A:
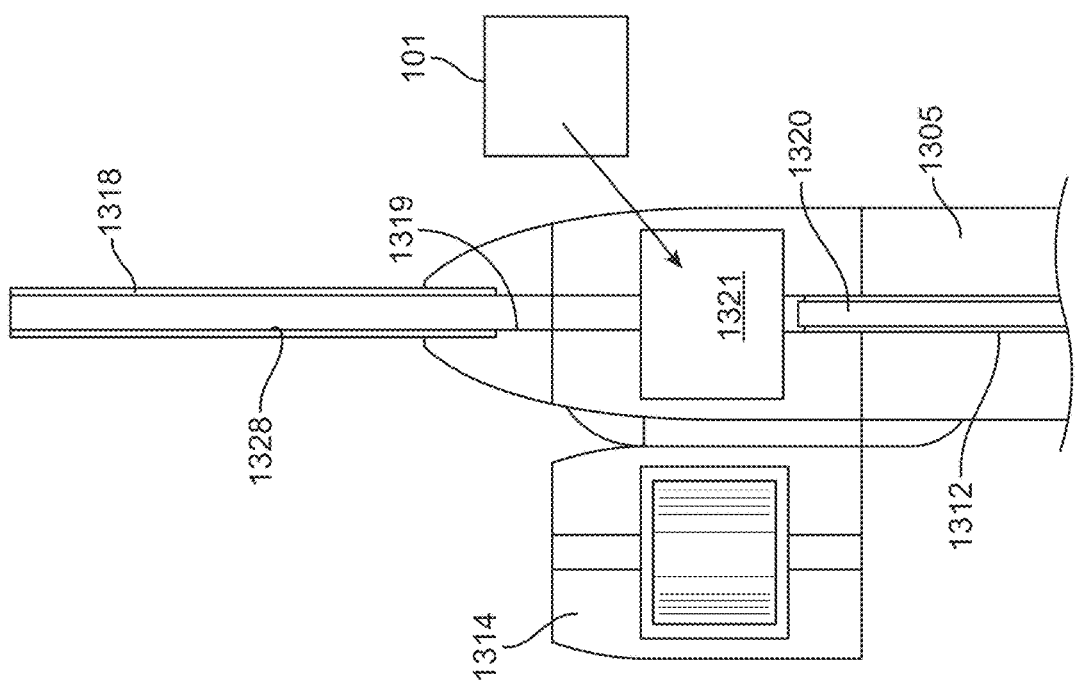

Still with respect to FIG. 14A, the delivery device 1110 can include an access door 1314 coupled to a region of the handle 1305, such as by a hinge 1317, so that the door 1314 can be rotated around the pivot axis of the hinge 1317 relative to the handle 1305. When the access door 1314 is in an open configuration, a recess 1321 is revealed. The patch of material 101 may be loaded within the recess 1321 for cutting into a stent 105 prior to delivery. The pusher 1320 positioned within the lumen 1378 of the cutter tube 1312 is retracted proximally relative to the recess 1321 such that the patch of material 101 may be positioned within the recess 1321. FIG. 14B shows the access door 1314 rotated to a closed configuration capturing the patch of material 101 within the recess 1321. In some implementations, the access door 1314 can be formed of a transparent or translucent material such that the patch of material 101 positioned within the recess 1321 may be visualized by a user following loading (see also FIG. 18A). The access door 1314 can also include one or more latches 1322 (see FIG. 19A) to ensure once the door 1314 is closed it remains closed until a user desires to open the door 1314 again. In some implementations, the latch of the access door 1314 can include interference fit features or magnets, or other element.

The recess can be within a portion of the instrument such as within the handle as described above. The recess may also be within a cartridge removably coupled to the instrument. The cartridge can be coupled to a distal portion of the instrument as shown herein and removed prior to deployment in the eye. The cartridge can also be coupled to a proximal portion of the instrument and may or may not be removed prior to deployment.

When the door 1314 is rotated around the pivot axis P from an open configuration into a closed configuration, the patch of material 101 positioned within the recess 1321 can be captured, compressed, and/or tensioned. The door 1314 can be adapted to engage at least some portion of the patch of material before the patch is cut. The door 1314 can prevent movement of the patch during the cutting with the cutter.

In some implementations, at least a portion of the recess 1321 can have a depth, for example, the portion aligned with a centerline of the implantation conduit, that is less than the thickness of the patch of material 101 held within the recess 1321. Upon closing the door 1314, the patch of material 101 is compressed slightly.

At least a portion of the patch of material 101 can be placed under tension prior to cutting. The cutting achieved by the cutter tube 1312 is improved when the patch of material 101 is placed under slight tension before cutting. The tensioning of the portion of the patch can include compressing a first portion and a second portion of the patch and tensioning a central portion of the patch, the central portion located between the first and second portions. The central portion of the patch becomes the implant upon cutting the patch with the cutter tube 1312.

Tensioning the portion of the patch can include activating an actuator to tension the portion of the patch. Activating the actuator can include rotate an actuator to tension the portion of the patch. For example, the cover can include an actuator and actuation of the actuator can tension at least a portion of the patch. However, tensioning need not be a separate actuation. As discussed elsewhere herein, closing the access door 1314 can provide both fixation and an amount of tension on the patch. FIGS. 15A-15C are cross-sectional schematic views of the handle 1305 showing the access door 1314 and the patch of material 101 positioned within the recess 1321. The door 1314 can include a feature configured to apply a small amount of tension or stretching force onto the patch of material 101 to improve cutting. The door 1314 can be coupled to a stretcher 1350 having a pair of flexible stretcher legs 1352. The stretcher legs 1352 extend into the recess 1312 until each of the feet 1354 at the end of the legs 1352 contact the patch of material 101 (see FIG. 15B). One foot 1354 can contact a first portion of the patch of material 101 on a first side of the center line and an opposite foot 1354 can contact a second portion of the patch of material 101 on a second, opposite side of the center line. The stretcher 1350 can be actuated from a first position in which the stretcher 1350 is elevated relative to the recess 1321. When the stretcher 1350 is urged downward, the stretcher legs flex and the feet 1354 are urged outward further away from the center line and away from one another (see arrows in FIG. 15C). The distance between the feet 1354 is sufficient to allow for the cutter tube to slide through the recess 1321 between the feet 1354 in an axial direction to cut the patch of material 101. The lower surface of the feet 1354 can have surface features 1355, for example ridges, bumps, or other texture that optimizes the interface between the feet 1354 and the patch of material 101. The surface features 1355 allow the feet 1354 to stretch the patch of material 101 outward as the feet 1355 are urged outward.

The stretcher 1350 can have any of a variety of configuration. The stretcher 1350 can be a button as shown in FIGS. 13A-13B and 15A-15C. The stretcher 1350 can be a dial as shown in FIGS. 18A-18B, FIGS. 19A-19B, FIGS. 20A-20C, FIG. 21, and FIG. 22. Any of a variety of other actuators are considered that are configured to impart tension on the patch 101. In implementations where the stretcher 1350 is a button the door 1314 can additionally incorporate a stretch release button 1357 (see FIG. 13A) to release the tension applied, if desired.

Figure 21:
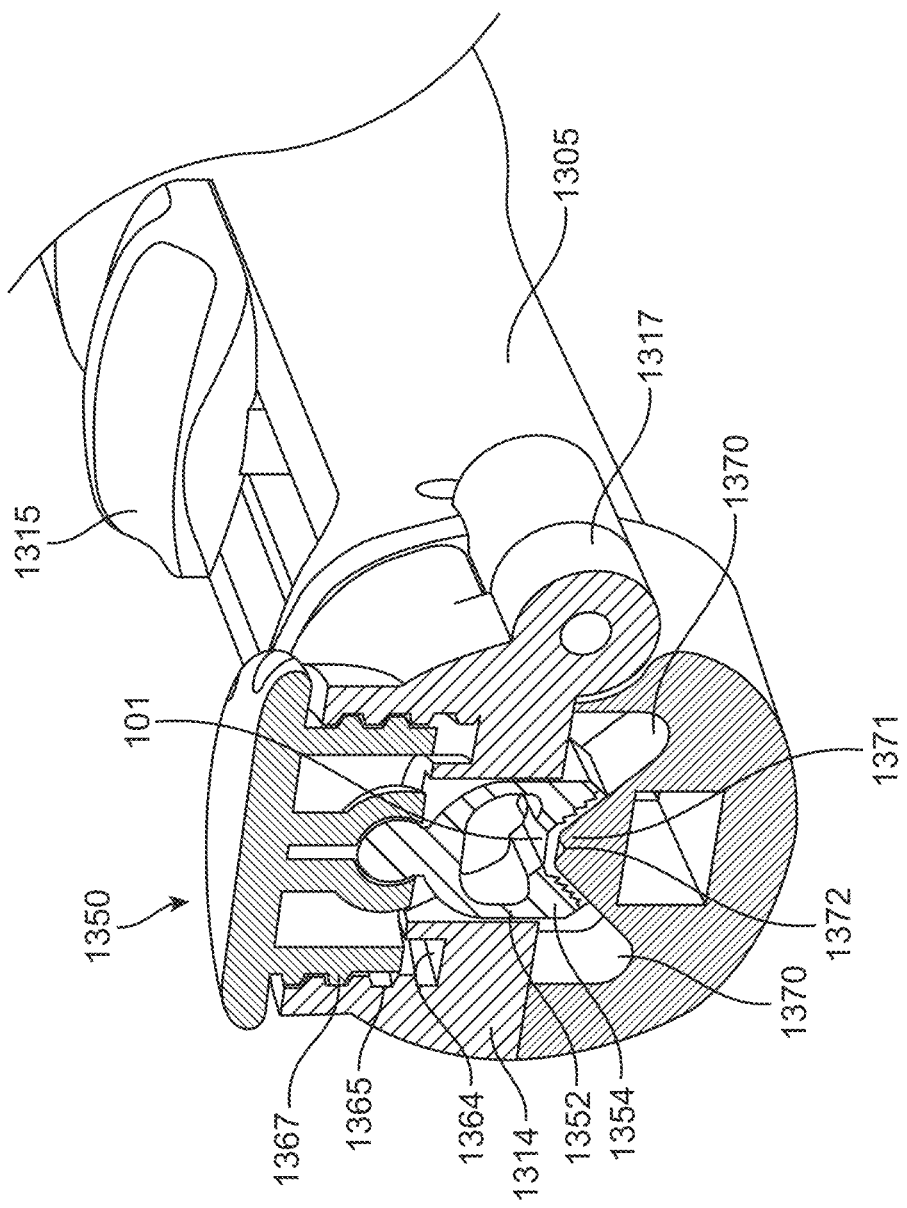
FIG. 21 is a cross-sectional view of the delivery device of FIG. 18A showing the stretcher.
Figure 22:
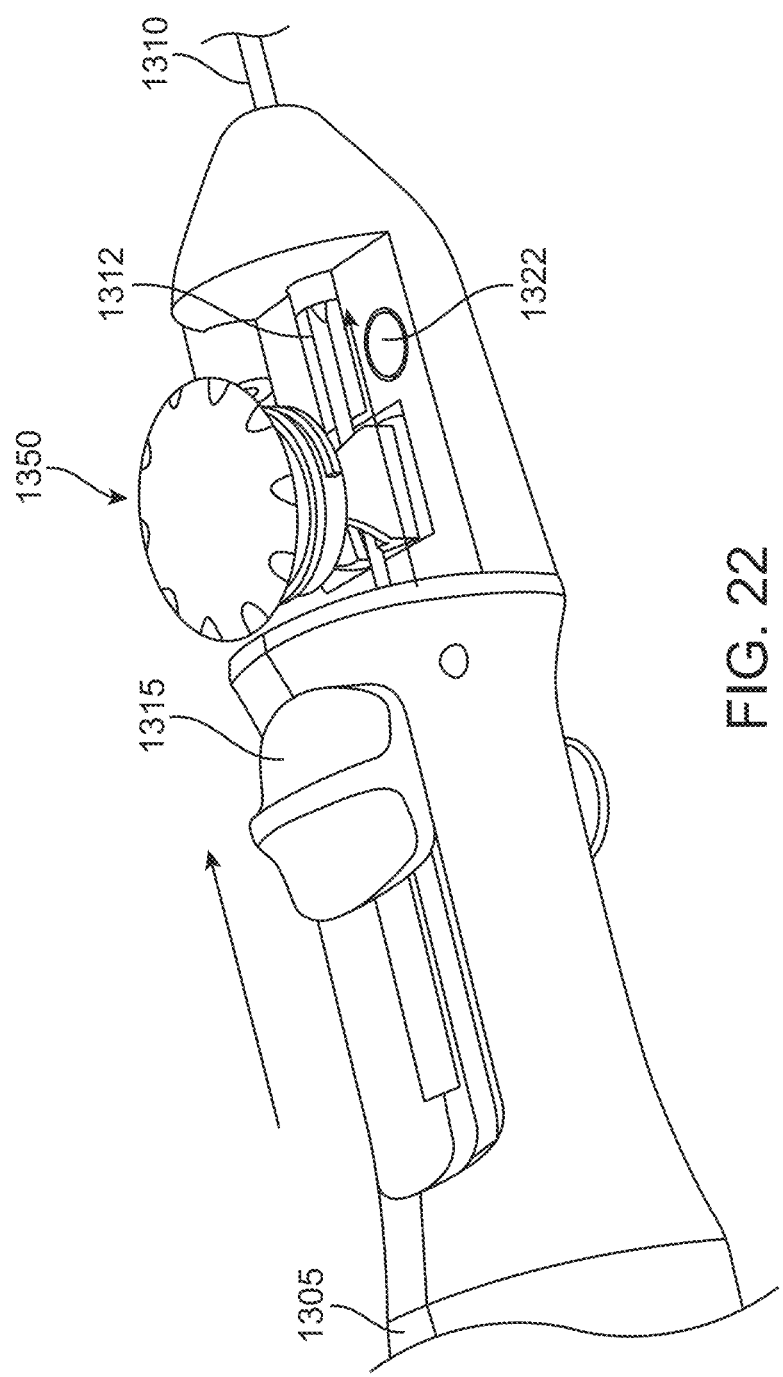
FIG. 22 is a partial view of a cutter tube advanced through the device of FIG. 18A.

Regardless the configuration, the stretcher 1350 can have an upper end region 1360 and a lower end region 1362 (see FIG. 20A) The upper end region 1360 is configured to be gripped and actuated (i.e. pushed or rotated). The lower end region 1362 of the stretcher 1350 can engage with the access door 1314. FIG. 21 shows an implementation of the stretcher 1350 that is a dial having threads 1367 on the lower end region 1362 of the stretcher 1350 that engage with corresponding threads 1365 of a bore 1364 in an upper surface of the door 1314. Rotation of the stretcher 1350 relative to the bore 1364 draws the stretcher 1350 further down into the bore 1364 and urges the feet 1354 further into the recess 1312.

As discussed elsewhere herein, tensioning the patch can include activating an actuator such as the dial to tension the patch. Tensioning can also be achieved without a separate actuation. For example, closing the door 1314 may achieve both fixation and tension of the patch of material without a separate actuator to provide the tension on the patch of material after compression. The door 1314, therefore, can achieve a prefixed tension on the patch of material upon closure without a separate activation of the stretcher 1350 up or down relative to the material.

The recess 1321 receives the patch of material 101. The recess 1321 can include a projection 1371 in the shape of an inverted V can project upward from a center line of the recess 1321 that urges the centerline of the patch of material 101 upward toward the door 1314 while allowing the sides of the patch of material 101 to hang downward into corresponding channels 1370 on either side of the centerline (see FIG. 19A and FIG. 21). Upon closing the door 1314, the stretcher legs 1352 extend into the recess 1312 until each of the feet 1354 of the stretcher legs 1352 contact the sides of the patch of material 101 hanging within the channels 1370 (see FIG. 21). One foot 1354 can contact a first portion of the patch of material 101 in a first channel 1370 adjacent the center line and an opposite foot 1354 can contact a second portion of the patch of material 101 in a second channel 1370 on the opposite side of the center line. When the stretcher 1350 is drawn further into the bore 1364, such as by turning the dial, the feet 1354 urge these portions deeper into their respective channels 1370 thereby compressing the centerline of the patch of material 101 against the inverted V 1371 of the recess 1321 (see FIG. 21). The distance between the feet 1354 is sufficient to allow the cutter tube 1312 to pass between them. The inverted V 1371 can include a shallow central channel 1372 sized and shaped to receive the lower wall geometry of the cutter tube 1312 as the cutter tube 1312 is advanced distally to cut the patch of material 101.

The cutting member can include a cutting member lumen, a distal opening, and a pair of opposed cutting edges. The cutting can include advancing the cutting member to cut a patch of material and capture the implant within the cutting member lumen. The pair of opposed cutting edges can cut the patch in two locations to separate the implant from a remainder of the patch of material. A distal portion of the cutting member can be beveled. The longitudinal axis of the implant can remain aligned with a longitudinal axis of the lumen of the cutting member as the cutting member finishes cutting the patch to form the implant.

The cutter tube 1312 can be a dual beveled hypotube forming two leading points 1372 (see FIGS. 23A-23D). The two leading points 1372 can be positioned above and below the patch of material 101, respectively, as the cutter tube 1312 is advanced into a cutting configuration and slices through the patch of material 101. The lower leading point 1372 can be received within the shallow central channel 1372 of the inverted V 1371 and the upper leading point 1372 glides over the patch of material 101. The leading points 1372 can be blunt or sharp. The cutting surfaces of the cutter tube 1312 include the inside edges 1374 of each bevel 1376. The inside edges 1374 are separated from one another by the lumen 1378 of the cutter tube 1312 so that the cutter tube 1312 slices the patch of material 101 in two locations. Thus, the inner diameter or distance between inside edges 1374 of the cutter tube 1312 determines the width of the stent 105 that is cut.

Figure 17B:
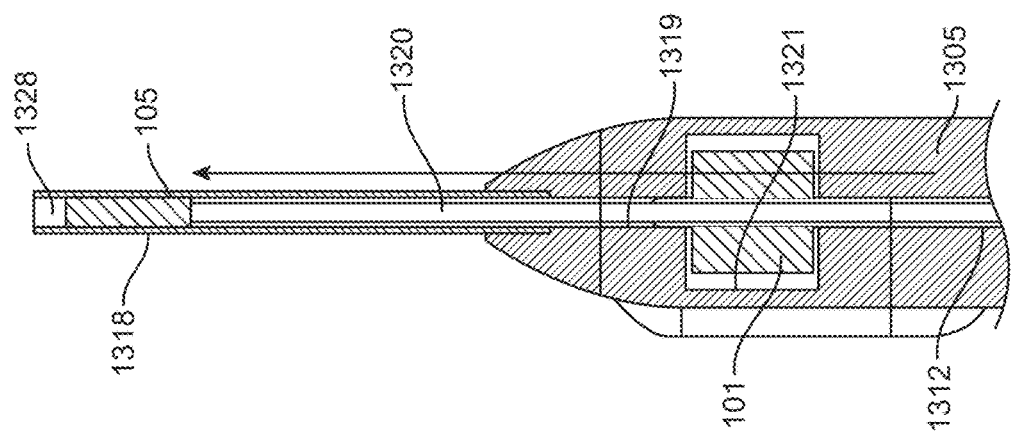
FIGS. 17A-17B are schematic view of a pusher priming a cut stent within the delivery shaft.
Figure 17A:
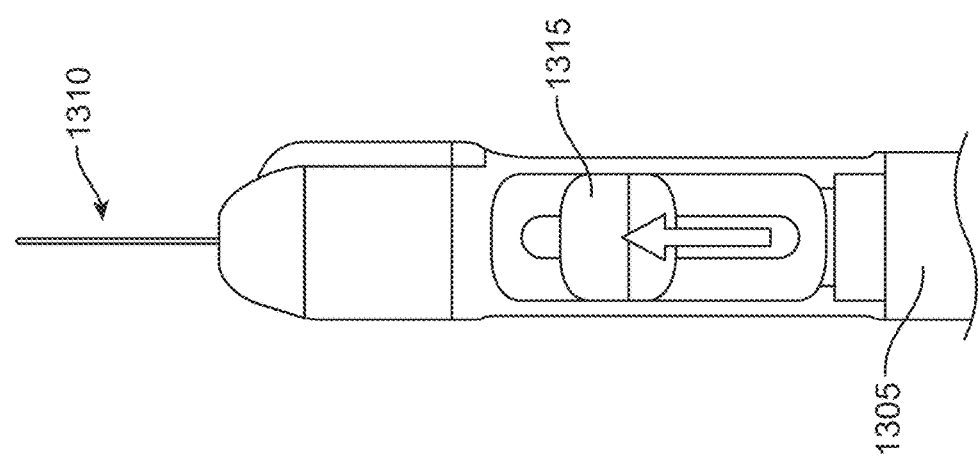

The stent 105, once cut, is contained within the lumen 1378 of the cutter tube 1312 creating an enclosure for the stent 105. The stent 105 can have a dimension that substantially fills the lumen 1378 of the cutter tube 1312. The axial motion of the cutter tube 1312 in a distal direction towards the cutting configuration positions the cutter tube 1312 so that its walls bridge the recess 1321 and forms part of the implantation conduit 1319. The lumen 1378 of the cutter tube 1312 can be coaxial (e.g., contiguous or non-contiguous) with the lumen of the elongate shaft 1310 through which the stent 105 will be delivered to the eye. For example, as shown in FIG. 17B, the cut stent 105 may be advanced out of the cutter tube 1312 along the implantation conduit 1319 towards the distal end of the delivery shaft 1310. Thus, the axial motion of the cutter tube 1312 along an axis of the implantation conduit 1319 simultaneously cuts the stent from the patch of material 101 and axially aligns the cut stent with or relative to the delivery shaft lumen such that the stent 105 may be deployed in the eye without any tissue transfer step.

The inner elongate member or pusher 1320 is movable relative to the delivery shaft lumen. The stent 105 can be pushed distally out from the cutter tube 1312 by the pusher 1320. As discussed above, the elongate shaft 1310 of the delivery device 1110 can include an outer tube 1318 and an inner pusher 1320 positioned within the lumen of the outer tube 1318. The pusher 1320 is sized and shaped to travel distally through the lumen 1378 of the cutter tube 1312 to urge the stent 105 towards the distal end of the outer tube 1318 (see FIG. 17B). In some implementations, the outer tube 1318 is fixed relative to the handle 1305 and the inner pusher 1320 is movable relative to the outer tube 1318 to deploy the stent 105 from the outer tube 1318. In other implementations, both the outer tube 1318 and the pusher 1320 are movable relative to the handle 1305 and to each other. The distal end of the pusher 1320 can be shaped to atraumatically urge the stent 105 in the distal direction.

Figure 18A:
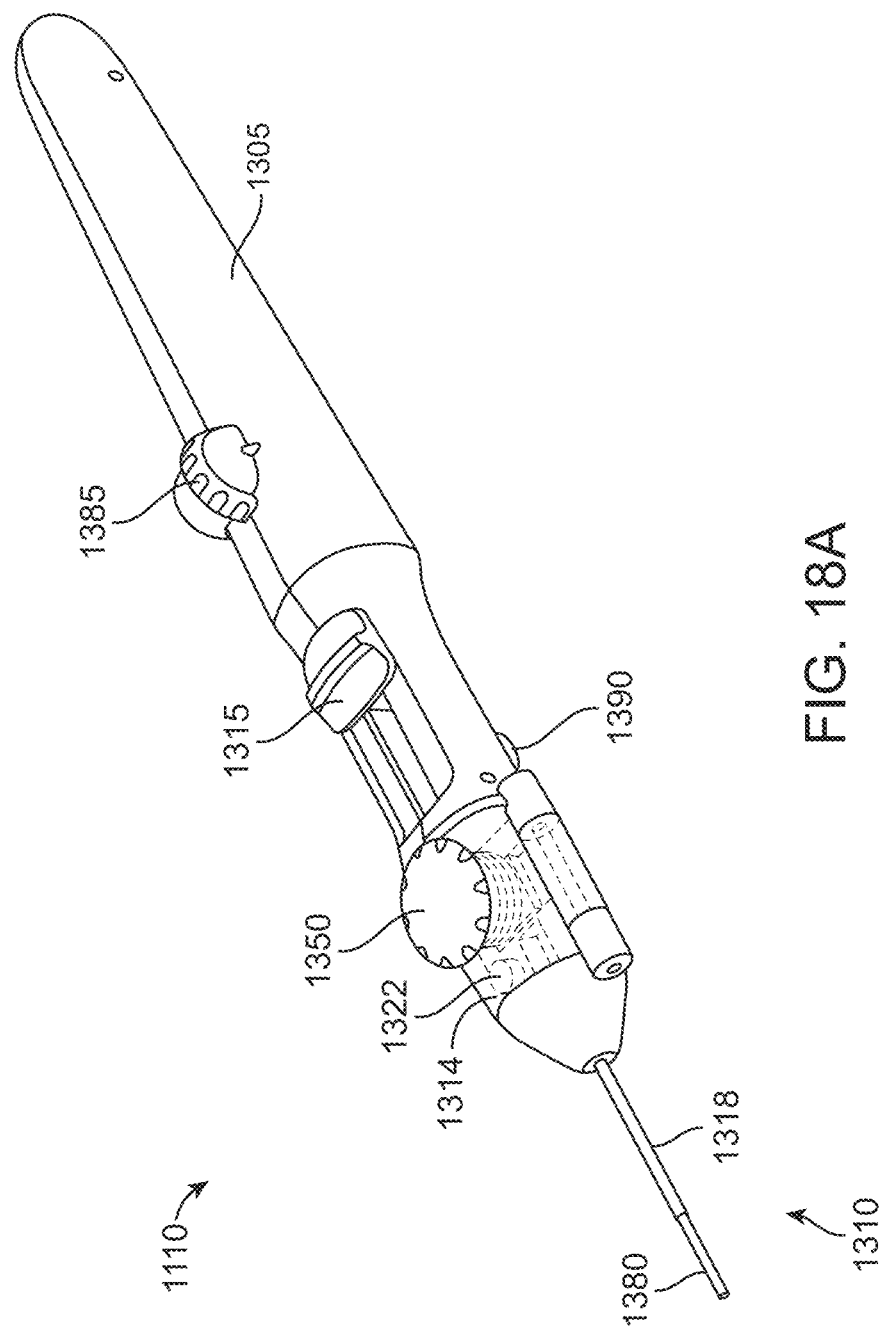
FIG. 18A is a top view of an implementation of a delivery device.
Figure 18B:
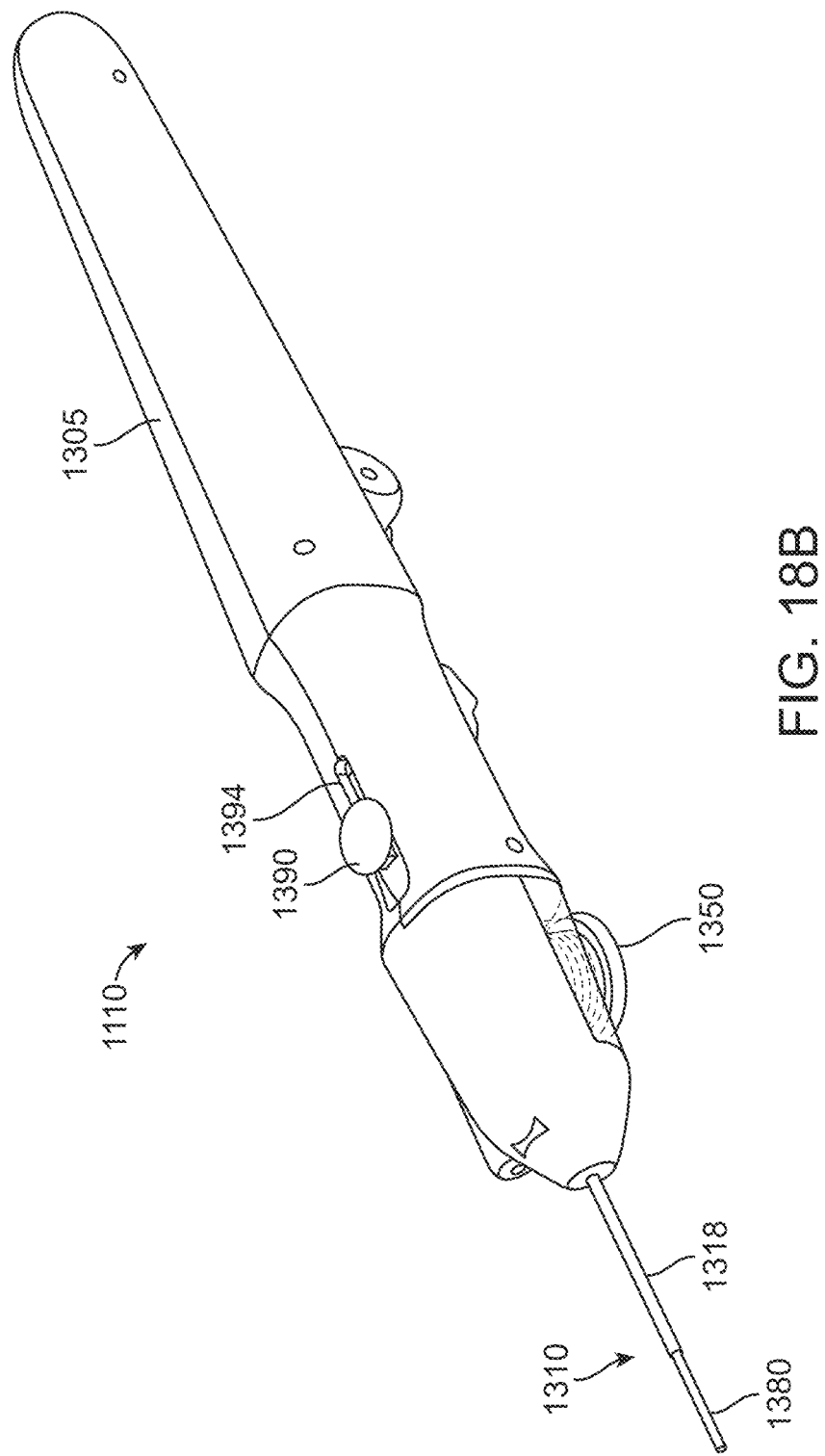
FIG. 18B is a bottom view of the delivery device of FIG. 18A.

In still further implementations, the elongate delivery shaft 1310 can include a fixed outer tube 1318 and an introducer tube 1380 positioned and movable through the lumen 1328 of the outer tube 1318 (see FIGS. 18A-18B). The pusher 1320, in turn, can be movable through the lumen 1382 of the introducer tube 1380. The distal end region of the elongate tubular member for delivering the implant into the eye can be angled, curved, and/or flexible. In some implementations, the introducer tube 1380 can have a curved shaped at its distal end region and/or the introducer tube 1380 can be flexible to conform to a curved shape. The curved shape of the distal end region of the introducer tube 1380 can conform to a shape of the desired implantation location, such as the curvature of the eye near the anterior angle. The outer tube 1318 can be a rigid tube and the introducer tube 1380 can be flexible. The pusher 1320 can be a shape-set Nitinol that is takes on the shape of the rigid outer tube 1318 when retracted proximally and allowed to relax back into its shape-set configuration (i.e. having a curve or bend away from the longitudinal axis of the outer tube 1318) when extended distally beyond the distal opening of the outer tube 1318. The introducer tube 1380 can be flexible enough to take on the shape of the pusher 1320 when the pusher 1320 extends beyond the outer tube 1318. Thus, the introducer tube 1380 can be more flexible than the pusher 1320 and the pusher 1320 can be more flexible than the outer tube 1318. In some implementations, the introducer tube 1380 can be formed of silicone, thermoplastic elastomer, polyethylene, polypropylene, or a combination thereof. The introducer tube 1380 can have a degree of stiffness, but not so stiff that it is incapable of being retracted over the pusher 1320 during deployment.

The introducer tube 1380 and pusher 1320 can work together to deploy the stent 105 in the eye after the stent 105 is cut by the cutter tube 1312. The pusher 1320 can urge the stent 105 out of the lumen 1378 of the cutter tube 1312 into the lumen 1382 of the introducer tube 1380. FIG. 24A shows the introducer tube 1380 extending through the lumen 1378 of the cutter tube 1312 and extending a distance past the distal end of the outer tube 1318. The stent 105 is positioned within the lumen 1382 of the introducer tube 1380 urged distally by the pusher 1320 also positioned within the lumen 1382 of the introducer tube 1380. The stent 105 is urged distally through the lumen 1382 by the pusher 1320 until the stent 105 is positioned within the distal end region of the introducer tube 1380 (FIG. 24B). At this stage of deployment, the pusher 1320 has advanced a distance beyond the distal end of the rigid outer tube 1318 such that the pusher 1320 can relax back into its curved or bent shape. The introducer tube 1380, which can be more flexible than the pusher 1320, takes on the shape of the pusher 1320. The cut stent 105 in this primed position near the distal end of the introducer tube 1380 is ready to be implanted in the eye. The introducer tube 1380 can be retracted while the pusher 1320 remains stationary to effectively push the stent 105 out from the lumen of the introducer tube 1380 (see FIG. 24C).

Advancing the implant from the proximal portion of the instrument can include pushing the implant out of the cutting member lumen and into the lumen of the elongate tubular member of the distal portion. The distal portion of the instrument can be positioned adjacent eye tissue to position the implant in the eye, for example, between the ciliary body and the sclera, while the implant remains at least partially inside the lumen of the distal portion of the instrument. The stent 105 can be deployed from the instrument upon retraction of the introducer tube 1380 from the implant while maintaining the implant's position relative to the adjacent eye tissue. The methods of implantation and delivery of the stent 105 are described in more detail below.

Motion of the cutting and deployment components (e.g., one or more of the cutter tube 1312, pusher 1320, introducer tube 1380, and outer tube 1318, if present) can be achieved by one or more actuators 1315 positioned on one or more regions of the handle 1305. In some implementations, the one or more actuators 1315 for a first function of the delivery device 1110 can be positioned on a first region of the handle 1305 and one or more actuators 1315 for a second function of the delivery device 1110 can be positioned on a second region of the handle 1305. A first plurality of actuators 1315 can be positioned on a first region the handle 1305 to prepare the patch of material 101 into a stent and a second plurality of actuators 1315 can be positioned on a second region of the handle 1305 to deploy the stent 105 cut from the patch 101. For example, the top region of the handle 1305 can include a first actuator(s) 1315 for capturing and/or stretching the patch of material 101, a second actuator(s) 1315 for moving the cutter tube 1312 to cut the patch of material 101, and a third actuator(s) 1315 for moving the pusher 1320 to position the cut stent 105 into a primed position for deployment from the device 1110. A bottom region of the handle 1305 can include a fourth actuator(s) 1315 for deploying the stent 105 in the eye.

FIG. 13A shows a top view of an implementation of a delivery device 1110 and FIG. 13B shows a bottom view of the device 1110. The top region of the handle 1305 can include a first actuator 1315 that is the stretcher 1350 for capturing and stretching the patch of material 101 within the recess and another actuator 1315 that is the slider for moving the cutter tube 1312. The bottom region of the handle 1305 can include an actuator 1315 that is the slider for moving the pusher 1320 to push the stent 105 from the outer tube 1318.

FIG. 18A shows a top view of an implementation of the delivery device 1110 and FIG. 18B shows a bottom view of the device 1110. The top region of the handle 1305 can include a first actuator 1315 that is the stretcher 1350 for capturing and stretching the patch of material 101 within the recess, a second actuator 1315 that is the slider for moving the cutter tube 1312, and a third actuator 1315 that is a wheel for incrementally advancing the pusher 1320. The bottom region of the handle 1305 can include a fourth actuator 1315 that is a spring retraction button for retracting the introducer tube 1380 to release the stent 105 from the shaft 1310.

The configuration of the actuators 1315 can vary. For example, the actuators 1315 can include any of a variety of sliders, dials, buttons, knobs, or other type of actuator.

Figure 25:
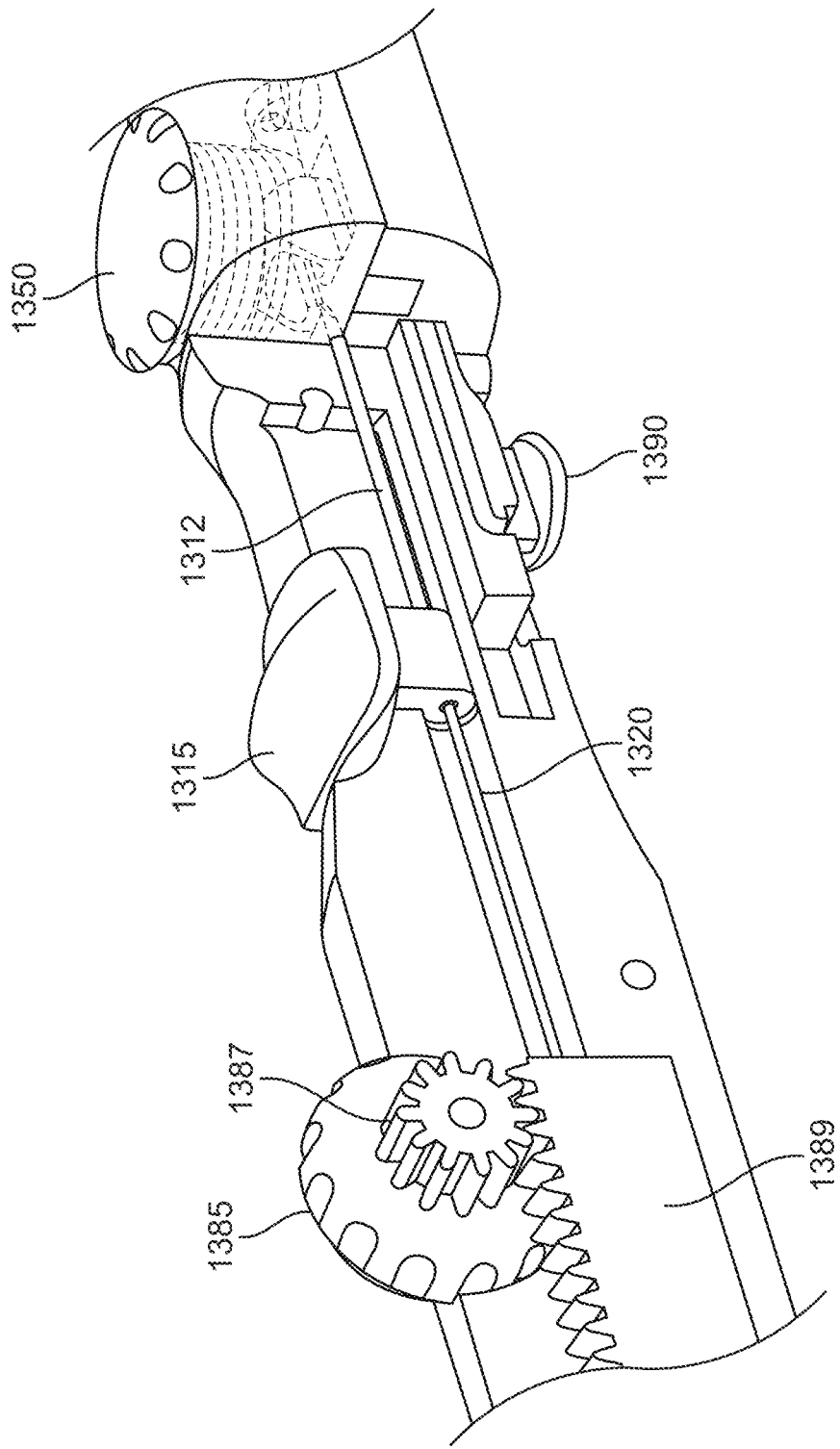
FIG. 25 is a partial, cross-sectional view showing advancement mechanisms for various axially movable components of the device of FIG. 18A.

In an implementation, the one or more actuators 1315 configured to axially move the one or more components of the device can include a scroll wheel 1385 (see FIG. 25). The scroll wheel 1385 may be connected to a pinion gear 1387 that engages with a corresponding rack gear 1389. Rotation of the pinion gear 1387 may cause the rack gear 1389 to move axially and advance or retract any of the axially movable components, such as the pusher 1320 or the cutter tube 1312. FIG. 25 shows the rack gear 1389 attached to the pusher 1320. The scroll wheel 1385 can provide more an incremental, precise motion of the component. A scroll wheel advancement mechanism is described in U.S. Pat. No. 10,154,924, and is incorporated herein by reference.

Figure 26:
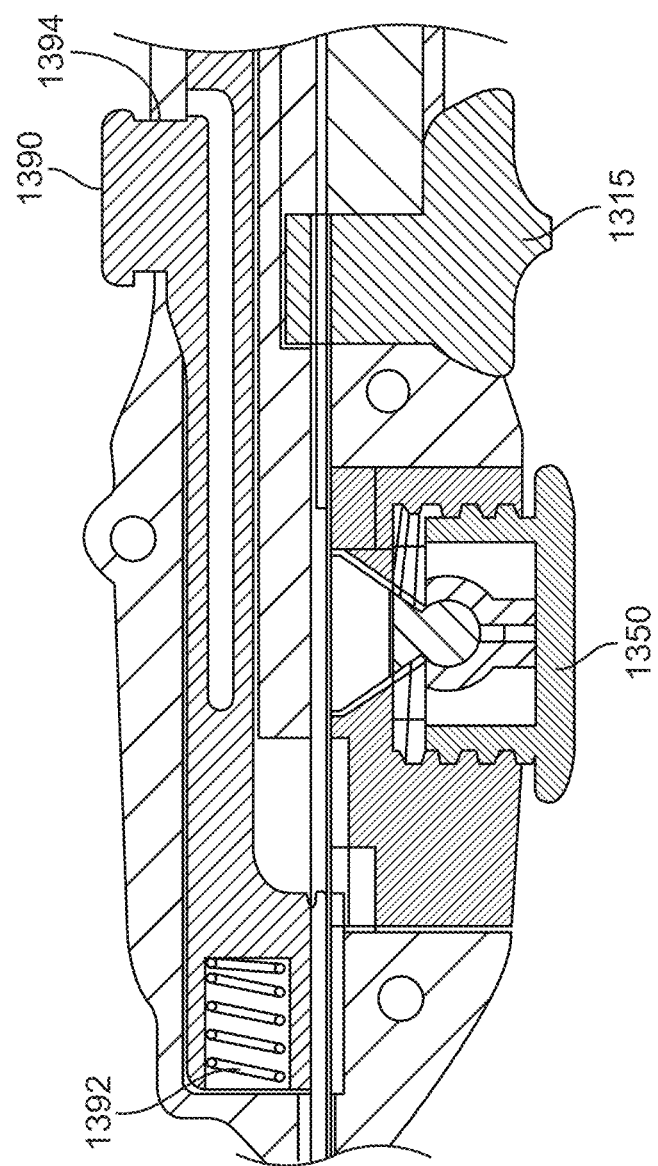
FIG. 26 is a partial, cross-sectional view of a retraction mechanism for the introducer tube of the device of FIG. 18A.

In another implementation, the one or more actuators 1315 configured to axially move the one or more components of the device can include a spring-loaded push button 1390. The introducer tube 1380 can be urged in a distal direction in an extended state relative to the handle 1305, which compresses a front spring 1392 (see FIG. 26). The push button 1390 can be held by a latch 1394 in a forward locked position such that the spring 1392 remains compressed during advancement of the stent 105 into the target location in the eye. Upon applying a downward force on the push button 1390, the latch 1394 is released allowing the spring 1392 to push the introducer tube 1380 a distance proximally thereby retracting the introducer tube 1380. Retraction of the introducer tube 1380 relative to the pusher 1320 can act to release the implant 105 in the eye. A spring-loaded retraction mechanism is described in U.S. Pat. No. 9,241,832, and is incorporated herein by reference.

Activating a first actuator can tension at least a portion of the patch before cutting, activating a second actuator can advance the cutting member to cut the patch after tensioning, activating a third actuator can advance the implant into a deployment position, and activating a fourth actuator can deploy the implant from the instrument. Each of the actuators can be operatively coupled to the instrument. It should also be appreciated that one or more steps in the cutting and/or deployment of the implant from the instrument can be combined. For example, a first actuator can fix, compress, and tension the portion of the patch before cutting, a second actuator can advance the cutting member and advance the cut implant into a deployment position, before a third actuator deploys the implant from the instrument in the eye. Advancing the implant from the proximal portion of the instrument can include pushing the implant out of the cutting member lumen and into the lumen of the elongate tubular member of the distal portion.

Advancement of the cutter tube 1312 can cut the stent 105 out from the patch of material resulting in the stent 105 being positioned within the lumen of the cutter tube 1312. The inner diameter of the cutter tube 1312 can be substantially the same as the inner diameter of the outer introducer tube 1380. The pusher 1320 can be urged distally through the lumen of the cutter tube 1312 urging the cut stent 105 within the lumen into the lumen of the introducer tube 1380. However, because the cutter tube 1312 and the introducer tube 1380 can be substantially the same in their inner dimensions, the cutter tube 1312 can be urged backwards by the introducer tube 1380 as the introducer tube 1380 is urged proximally by the spring. The stent 105 can be substantially contained within the implantation conduit and advanced line-to-line within the instrument as it is urged distally. Once the stent 105 is cut from the patch of material, the pathway of implantation for the stent 105 can include the lumen of the cutter tube 1312, the lumen of the introducer tube 1380 and any other conduit therebetween so that the stent throughout its transport within the implantation conduit avoids having to transfer between "gaps" or "edges" in the implantation conduit. The implantation conduit provides a smooth path for deployment of the stent 105 through the instrument.

Trephination of tissue and loading of tissue using a delivery device may be performed simultaneously or sequentially. In a preferred implementation, the cutting and injecting are integrated. This allows for tissue cutting/trephining to be performed in/along the path of implantation. The dimensions of the tissue strip are such that manipulating it can be difficult. Thus, by integrating the cutting and implantation, no additional manipulations are necessary. The tissue can be cut and loaded into a tissue delivery pathway without removing or manipulating the tissue outside of the cutting device prior to transfer into an intra-ocular applier. The same device can be used to trephine tissue forming the stent and then inject/implant the stent into the eye enabling a seamless and atraumatic loading of the fine, micro-sized biostent tissue without transit manipulation.

The tissue can be, for example, corneal, scleral or other cartilaginous tissue. A section of tissue is cut using the delivery device and/or cutting device. The tissue is loaded into a tissue delivery pathway that at least partially include the eye without removing the tissue completely from the cutting device prior to transfer into an intra-ocular delivery device. In a situation where a single integrated trephination/injector device is used, that device is used for both trephination of tissue as well as injection and implantation of the tissue into the eye.

In another implementation, there is performed simultaneous or sequential trephination of tissue and insertion of tissue into the eye. A section of tissue is cut and loaded into a tissue delivery pathway. This is performed using a single device that is configured to trephine tissue and configured to load the trephined tissue into an intra-ocular delivery applier for application of the tissue to the eye.

The applier device can also be used as a delivery device and loading platform device or conduit. In such an implantation, the device is configured to contain or otherwise house the tissue prior to implantation. The device permits longitudinal or other directional movement of the tissue for implantation into the eye. The device can be configured for simultaneous or sequential trephination and application loading of the tissue such that, upon completion of a trephination step, the trephined or cut tissue is loaded within a delivery conduit of the applier device. The trephination device can be coupled to the intraocular delivery device by a coupling or other attachment mechanism, which facilitate tissue transfer into the delivery device.

The stent can be harvested by the trephination device from the patient at the time of surgery. The stent can also be formed from a patch of material obtained from a donor or other tissue-engineering source. The patch of material may be pre-cut into a stent shape and pre-loaded within a region of the delivery device. The patch of material may be cut at the time of implantation using a trephination device.

In an implementation, a patch of material 101 may be manually loaded through the cut-out windows 326 of the outer tube 318 with the pusher 320 in the lumen 328 of the outer tube 318 fully retracted in the proximal position. Once the patch of material 101 is loaded within the delivery device 110, the shaft 310 and the patch of material 101 may be loaded within a trephination cartridge 205. The cover 314 of the trephination cartridge 205 can be removed from the base 324 revealing the recess 321 of the base 324. The shaft 310 of the delivery device 110 is positioned within the slots 332, 334 such that the patch of material 101 is positioned within the recess 321 therebetween.

The cover 314 of the trephination cartridge 205 is replaced onto the base 324 compressing and/or tensioning the patch of material 101 within the trephination cartridge 205 in the closed configuration. The cutting member 312 can be inserted through the bore 338 of the cover 314 urging the blades 344 through the cover 314 towards the patch of material 101. The cutting member 312 can be seated within the trephination cartridge 205 such that the blades 344 of the cutting member 312 fully slice through the patch of material 101. With the blades 344 still in the full cut position relative to the trephination cartridge 205, the pusher 320 is urged distally to prime the shaft 310 and place the now cut stent 105 within the lumen of the outer tube 318 towards the opening from the lumen 328 near the distal-most end of the tube 318. The delivery device 110 is now ready to be used in a patient.

In an implementation, a patch of material 101 may be loaded within the recess 1321 of a delivery device 1110. The access door 1314 may be opened and the patch of material 101 placed in the recess 1321. The door 1314 may be closed thereby capturing and at least partially compressing the patch of material 101 within the recess 1321. The stretcher 1350 may be actuated to impart a tension on the patch of material 101 prior to cutting with the cutter tube 1312. The cutter tube 1312 can be actuated to slide distally thereby cutting the patch of material 101 into a stent 105. The pusher 1320 can then be urged distally to prime the shaft 1310 by positioning the cut stent 105 within a distal end region of the lumen 1382 of the introducer tube 1380. The pusher 1320, once advanced distal to the rigid outer tube 1318, can relax into a curved shape thereby urging the introducer tube 1380 to also take on this curved shape. The delivery device 110 is now ready to be used in a patient. The introducer tube 1380 may be flexible and/or have a curved shaped at its distal end region, as discussed above, configured to conform to a shape of the desired implantation location, such as the curvature of the eye near the anterior angle.

In general, the stent 105 positioned within the shaft of the delivery device can be implanted through a clear corneal or scleral incision that is formed using the delivery device or a device separate from the delivery device. A viewing lens such as a gonioscopy lens can be positioned adjacent the cornea. The viewing lens enables viewing of internal regions of the eye, such as the scleral spur and scleral junction, from a location in front of the eye. The viewing lens may optionally include one or more guide channels sized to receive the shaft of the delivery device. An endoscope can also be used during delivery to aid in visualization. Ultrasonic guidance can be used as well using high-resolution bio-microscopy, OCT, and the like. Alternatively, a small endoscope can be inserted through another limbal incision in the eye to image the eye during implantation.

The distal tip of the shaft holding the stent 105 can penetrate through the cornea (or sclera) to access the anterior chamber. In this regard, the single incision can be made in the eye, such as within the limbus of the cornea. In an embodiment, the incision is very close to the limbus, such as either at the level of the limbus or within 2 mm of the limbus in the clear cornea. The shaft can be used to make the incision or a separate cutting device can be used. For example, a knife-tipped device or diamond knife can be used initially to enter the cornea. A second device with a spatula tip can then be advanced over the knife tip wherein the plane of the spatula is positioned to coincide with the dissection plane.

The corneal incision can have a size that is sufficient to permit passage of the shaft. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision.

After insertion through the incision, the shaft can be advanced into the anterior chamber along a pathway that enables the stent 105 to be delivered from the anterior chamber into the target location, such as the supraciliary or suprachoroidal space. With the shaft positioned for approach, the shaft can be advanced further into the eye such that the distal-most tip of the shaft penetrates the tissue at the angle of the eye, for example, the iris root or a region of the ciliary body or the iris root part of the ciliary body near its tissue border with the scleral spur.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. The shaft can travel along a pathway that is toward the angle of the eye and the scleral spur such that the shaft passes near the scleral spur on the way to the supraciliary space, but does not necessarily penetrate the scleral spur during delivery. Rather, the shaft can abut the scleral spur and move downward to dissect the tissue boundary between the sclera and the ciliary body, the dissection entry point starting just below the scleral spur near the iris root or the iris root portion of the ciliary body. In another embodiment, the delivery pathway of the implant intersects the scleral spur.

The shaft can approach the angle of the eye from the same side of the anterior chamber as the deployment location such that the shaft does not have to be advanced across the iris. Alternately, the shaft can approach the angle of the eye from across the anterior chamber AC such that the shaft is advanced across the iris and/or the anterior chamber toward the opposite angle of the eye. The shaft can approach the angle of the eye along a variety of pathways. The shaft does not necessarily cross over the eye and does not intersect the center axis of the eye. In other words, the corneal incision and the location where the stent 105 is implanted at the angle of the eye can be in the same quadrant when viewed looking toward the eye along the optical axis. Also, the pathway of the stent 105 from the corneal incision to the angle of the eye ought not to pass through the centerline of the eye to avoid interfering with the pupil.

The shaft can be continuously advanced into the eye, for example approximately 6 mm. The dissection plane of the shaft can follow the curve of the inner scleral wall such that the stent 105 mounted in the shaft, for example after penetrating the iris root or the iris root portion of the ciliary body CB, can bluntly dissect the boundary between tissue layers of the scleral spur and the ciliary body CB such that a distal region of the stent 105 extends through the supraciliary space and then, further on, is positioned between the tissue boundaries of the sclera and the choroid forming the suprachoroidal space.

Once properly positioned, the stent 105 can be released. In some implementations, the stent 105 can be released by withdrawing the outer tube 318 of the shaft 310 while the pusher 320 prevents the stent 105 from withdrawing with the outer tube 318. In other implementations, the stent 105 can be released by withdrawing the introducer tube 1380 while the pusher 1320 remains stationary, as described elsewhere herein.

Once implanted, the stent 105 forms a fluid communication pathway between the anterior chamber and the target pathway (e.g., supraciliary space or suprachoroidal space). As mentioned, the stent 105 is not limited to being implanted into the suprachoroidal or supraciliary space. The stent 105 can be implanted in other locations that provide fluid communication between the anterior chamber and locations in the eye, such as Schlemm's canal or a subconjunctival location of the eye. In another implementation, the stent 105 is implanted to form a fluid communication pathway between the anterior chamber and the Schlemm's canal and/or communication pathway between the anterior chamber and a subconjunctival location of the eye. It should be appreciated the device described herein can also be used to deliver a stent trans-sclerally as well from an ab interno approach.

As mentioned above, the material used to form the stent can be impregnated with one or more therapeutic agents for additional treatment of an eye disease process.

A wide variety of systemic and ocular conditions such as inflammation, infection, cancerous growth, may be prevented or treated using the stents described herein. More specifically, ocular conditions such as glaucoma, proliferative vitreoretinopathy, diabetic retinopathy, uveitis, keratitis, cytomegalovirus retinitis, cystoid macular edema, herpes simplex viral and adenoviral infections can be treated or prevented.

The following classes of drugs could be delivered using the devices of the present invention: antiproliferatives, antifibrotics, anesthetics, analgesics, cell transport/mobility impending agents such as colchicine, vincristine, cytochalasin B and related compounds; antiglaucoma drugs including beta-blockers such as timolol, betaxolol, atenolol, and prostaglandin analogues such as bimatoprost, travoprost, latanoprost etc; carbonic anhydrase inhibitors such as acetazolamide, methazolamide, dichlorphenamide, diamox; and neuroprotectants such as nimodipine and related compounds. Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericine B, ketoconazole, and related compounds; anti-viral agents such as trifluorothymidine, acyclovir, ganciclovir, DDI, AZT, foscarnet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Non-steroidal anti-inflammatories (NSAIDs) may also be delivered, such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (CELEBREX® from Pharmacia Corp., Peapack, N.J.; COX-1 inhibitors), including a prodrug Nepafenac®; immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Anticlotting agents such as heparin, antifibrinogen, fibrinolysin, anti clotting activase, etc., can also be delivered.

Antidiabetic agents that may be delivered using the present devices include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levami sole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, nucleic acids, saccharides, lipids, glycolipids, glycoproteins, and other macromolecules can be delivered using the present devices. Examples include: endocrine hormones such as pituitary, insulin, insulin-related growth factor, thyroid, growth hormones; heat shock proteins; immunological response modifiers such as muramyl dipeptide, cyclosporins, interferons (including α, β, and γ interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anit VEGF, Interfurons), among others and anticlotting agents including anticlotting activase. Further examples of macromolecules that can be delivered include monoclonal antibodies, brain nerve growth factor (BNGF), celiary nerve growth factor (CNGF), vascular endothelial growth factor (VEGF), and monoclonal antibodies directed against such growth factors. Additional examples of immunomodulators include tumor necrosis factor inhibitors such as thalidomide.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. The reference point used herein may be the operator such that the terms "proximal" and "distal" are in reference to an operator using the device. A region of the device that is closer to an operator may be described herein as "proximal" and a region of the device that is further away from an operator may be described herein as "distal". Similarly, the terms "proximal" and "distal" may also be used herein to refer to anatomical locations of a patient from the perspective of an operator or from the perspective of an entry point or along a path of insertion from the entry point of the system. As such, a location that is proximal may mean a location in the patient that is closer to an entry point of the device along a path of insertion towards a target and a location that is distal may mean a location in a patient that is further away from an entry point of the device along a path of insertion towards the target location. However, such terms are provided to establish relative frames of reference, and are not intended to limit the use or orientation of the devices to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

The systems disclosed herein may be packaged together in a single package. The finished package would be sterilized using sterilization methods such as Ethylene oxide or radiation and labeled and boxed. Instructions for use may also be provided in-box or through an internet link printed on the label.

The invention claimed is:

1. A system for preparing an implant for implantation into, and of inserting the implant into an eye of a patient, the system comprising:
   a cartridge configured to contain a patch of a material;
   at least one cutting member configured to cut the patch to form an implant from the patch, the implant located within a portion of the cartridge; and
   a handpiece forming a delivery instrument upon coupling the cartridge to the handpiece, the delivery instrument comprising a distal portion sized and shaped for insertion into an anterior chamber of the eye, wherein the distal portion comprises a lumen within an elongate tubular member,
   wherein a dimension of the implant substantially fills an internal dimension of the lumen of the elongate tubular member of the distal portion of the delivery instrument.

2. The system of claim 1, wherein the portion of the cartridge comprises a recess sized to receive the patch.

3. The system of claim 1, wherein the cartridge prevents movement of the patch during cutting of the patch with the at least one cutting member.

4. The system of claim 3, further comprising an element configured to apply tension to at least a portion of the patch prior to cutting the patch with the at least one cutting member.

5. The system of claim 1, wherein the material comprises biologically-derived material suitable for implantation into the eye.

6. The system of claim 5, wherein the biologically-derived material comprises tissue harvested from a donor or from the patient, allograft material, or xenograft material.

7. The system of claim 1, wherein the material comprises an engineered or 3D-printed material suitable for implantation into the eye.

8. The system of claim 1, wherein the implant comprises one or more therapeutic agents.

9. The system of claim 1, wherein the at least one cutting member comprises at least one pair of opposed cutting edges.

10. The system of claim 1, wherein the implant comprises a longitudinal axis and wherein the longitudinal axis of the implant is aligned with a longitudinal axis of the lumen of the elongate tubular member after completion of the cutting to form the implant.

11. The system of claim 1, wherein a distal end region of the elongate tubular member is at least one of angled or curved or flexible.

12. The system of claim 1, wherein the lumen comprises a circular cross-section.

13. The system of claim 1, further comprising an actuator on the handpiece, the actuator configured to retract the elongate tubular member from the implant while maintaining the implant position relative to adjacent eye tissue.

14. The system of claim 13, further comprising an internal elongate member configured to contact a proximal end of the implant while the elongate tubular member is retracted by the actuator.

15. The system of claim 13, wherein the actuator comprises at least one of a wheel, slide or button.

16. The system of claim 13, wherein the biologically-derived material comprises tissue harvested from a donor or from the patient, allograft material, or xenograft material.

17. The system of claim 1, wherein a distal-most tip of the elongate tubular member is blunt to allow for dissecting eye tissue without cutting the eye tissue.

18. The system of claim 1, wherein the elongate tubular member comprises one or more windows that communicate with the lumen.

19. The system of claim 18, wherein each of the one or more windows has a depth that is at least as deep as a thickness of the implant.

20. The system of claim 1, wherein the lumen of the elongate tubular member comprises a length, and wherein the lumen comprises one or more openings at one or more locations along the length.

21. A system for preparing an implant for implantation into, and of inserting the implant into an eye of a patient, the system comprising:
    a cartridge configured to contain a patch of a material;
    at least one cutting member configured to cut the patch to form an implant from the patch, the implant located within a portion of the cartridge; and
    a handpiece forming a delivery instrument upon coupling the cartridge to the handpiece, the delivery instrument comprising a distal portion sized and shaped for insertion into an anterior chamber of the eye, wherein the distal portion comprises a lumen within an elongate tubular member comprising a circular cross-section.

22. The system of claim 21, wherein the portion of the cartridge comprises a recess sized to receive the patch.

23. The system of claim 21, wherein the cartridge prevents movement of the patch during cutting of the patch with the at least one cutting member.

24. The system of claim 23, further comprising an element configured to apply tension to at least a portion of the patch prior to cutting the patch with the at least one cutting member.

25. The system of claim 21, wherein the material comprises biologically-derived material suitable for implantation into the eye.

26. The system of claim 21, wherein the material comprises an engineered or 3D-printed material suitable for implantation into the eye.

27. The system of claim 21, wherein the implant comprises one or more therapeutic agents.

28. The system of claim 21, wherein the at least one cutting member comprises at least one pair of opposed cutting edges.

29. The system of claim 21, wherein a dimension of the implant substantially fills an internal dimension of the lumen of the elongate tubular member of the distal portion of the delivery instrument.

30. The system of claim 21, wherein the implant comprises a longitudinal axis and wherein the longitudinal axis of the implant is aligned with a longitudinal axis of the lumen of the elongate tubular member after completion of the cutting to form the implant.

31. The system of claim 21, wherein a distal end region of the elongate tubular member is at least one of angled or curved or flexible.

32. The system of claim 21, further comprising an actuator on the handpiece, the actuator configured to retract the elongate tubular member from the implant while maintaining the implant position relative to adjacent eye tissue.

33. The system of claim 32, further comprising an internal elongate member configured to contact a proximal end of the implant while the elongate tubular member is retracted by the actuator.

34. The system of claim 32, wherein the actuator comprises at least one of a wheel, slide or button.

35. The system of claim 21, wherein a distal-most tip of the elongate tubular member is blunt to allow for dissecting eye tissue without cutting the eye tissue.

36. The system of claim 21, wherein the elongate tubular member comprises one or more windows that communicate with the lumen.

37. The system of claim 36, wherein each of the one or more windows has a depth that is at least as deep as a thickness of the implant.

38. The system of claim 21, wherein the lumen of the elongate tubular member comprises a length, and wherein the lumen comprises one or more openings at one or more locations along the length.

39. A system for preparing an implant for implantation into, and of inserting the implant into an eye of a patient, the system comprising:
    a cartridge configured to contain a patch of a material;
    at least one cutting member configured to cut the patch to form an implant from the patch, the implant located within a portion of the cartridge;
    a handpiece forming a delivery instrument upon coupling the cartridge to the handpiece, the delivery instrument comprising a distal portion sized and shaped for insertion into an anterior chamber of the eye, wherein the distal portion comprises a lumen within an elongate tubular member;
    an actuator on the handpiece, the actuator comprising at least one of a wheel, slide, or button that is configured to retract the elongate tubular member from the implant while maintaining the implant position relative to adjacent eye tissue.

40. The system of claim 39, wherein the portion of the cartridge comprises a recess sized to receive the patch.

41. The system of claim 39, wherein the cartridge prevents movement of the patch during cutting of the patch with the at least one cutting member.

42. The system of claim 41, further comprising an element configured to apply tension to at least a portion of the patch prior to cutting the patch with the at least one cutting member.

43. The system of claim 39, wherein the material comprises biologically-derived material suitable for implantation into the eye.

44. The system of claim 43, wherein the biologically-derived material comprises tissue harvested from a donor or from the patient, allograft material, or xenograft material.

45. The system of claim 39, wherein the material comprises an engineered or 3D-printed material suitable for implantation into the eye.

46. The system of claim 39, wherein the implant comprises one or more therapeutic agents.

47. The system of claim 39, wherein the at least one cutting member comprises at least one pair of opposed cutting edges.

48. The system of claim 39, wherein a dimension of the implant substantially fills an internal dimension of the lumen of the elongate tubular member of the distal portion of the delivery instrument.

49. The system of claim 39, wherein the implant comprises a longitudinal axis and wherein the longitudinal axis of the implant is aligned with a longitudinal axis of the lumen of the elongate tubular member after completion of the cutting to form the implant.

50. The system of claim 39, wherein a distal end region of the elongate tubular member is at least one of angled or curved or flexible.

51. The system of claim 39, wherein the lumen comprises a circular cross-section.

52. The system of claim 39, further comprising an internal elongate member configured to contact a proximal end of the implant while the elongate tubular member is retracted by the actuator.

53. The system of claim 39, wherein a distal-most tip of the elongate tubular member is blunt to allow for dissecting eye tissue without cutting the eye tissue.

54. The system of claim 39, wherein the elongate tubular member comprises one or more windows that communicate with the lumen.

55. The system of claim 54, wherein each of the one or more windows has a depth that is at least as deep as a thickness of the implant.

56. The system of claim 39, wherein the lumen of the elongate tubular member comprises a length, and wherein the lumen comprises one or more openings at one or more locations along the length.

57. A system for preparing an implant for implantation into, and of inserting the implant into an eye of a patient, the system comprising:
a cartridge configured to contain a patch of a material;
at least one cutting member configured to cut the patch to form an implant from the patch, the implant located within a portion of the cartridge; and
a handpiece forming a delivery instrument upon coupling the cartridge to the handpiece, the delivery instrument comprising a distal portion sized and shaped for insertion into an anterior chamber of the eye, wherein the distal portion comprises a lumen within an elongate tubular member, wherein a distal-most tip of the elongate tubular member is blunt to allow for dissecting eye tissue without cutting the eye tissue.

58. The system of claim 57, wherein the portion of the cartridge comprises a recess sized to receive the patch.

59. The system of claim 57, wherein the cartridge prevents movement of the patch during cutting of the patch with the at least one cutting member.

60. The system of claim 59, further comprising an element configured to apply tension to at least a portion of the patch prior to cutting the patch with the at least one cutting member.

61. The system of claim 57, wherein the material comprises biologically-derived material suitable for implantation into the eye.

62. The system of claim 61, wherein the biologically-derived material comprises tissue harvested from a donor or from the patient, allograft material, or xenograft material.

63. The system of claim 57, wherein the material comprises an engineered or 3D-printed material suitable for implantation into the eye.

64. The system of claim 57, wherein the implant comprises one or more therapeutic agents.

65. The system of claim 57, wherein the at least one cutting member comprises at least one pair of opposed cutting edges.

66. The system of claim 57, wherein a dimension of the implant substantially fills an internal dimension of the lumen of the elongate tubular member of the distal portion of the delivery instrument.

67. The system of claim 57, wherein the implant comprises a longitudinal axis and wherein the longitudinal axis of the implant is aligned with a longitudinal axis of the lumen of the elongate tubular member after completion of the cutting to form the implant.

68. The system of claim 57, wherein a distal end region of the elongate tubular member is at least one of angled or curved or flexible.

69. The system of claim 57, wherein the lumen comprises a circular cross-section.

70. The system of claim 57, further comprising an actuator on the handpiece, the actuator configured to retract the elongate tubular member from the implant while maintaining the implant position relative to adjacent eye tissue.

71. The system of claim 70, further comprising an internal elongate member configured to contact a proximal end of the implant while the elongate tubular member is retracted by the actuator.

72. The system of claim 70, wherein the actuator comprises at least one of a wheel, slide or button.

73. The system of claim 57, wherein the elongate tubular member comprises one or more windows that communicate with the lumen.

74. The system of claim 73, wherein each of the one or more windows has a depth that is at least as deep as a thickness of the implant.

75. The system of claim 57, wherein the lumen of the elongate tubular member comprises a length, and wherein the lumen comprises one or more openings at one or more locations along the length.

76. A system for preparing an implant for implantation into, and of inserting the implant into an eye of a patient, the system comprising:
a cartridge configured to contain a patch of a material;
at least one cutting member configured to cut the patch to form an implant from the patch, the implant located within a portion of the cartridge; and
a handpiece forming a delivery instrument upon coupling the cartridge to the handpiece, the delivery instrument comprising a distal portion sized and shaped for insertion into an anterior chamber of the eye, wherein the distal portion comprises a lumen within an elongate tubular member, wherein the elongate tubular member comprises one or more windows that communicate with the lumen.

77. The system of claim 76, wherein the portion of the cartridge comprises a recess sized to receive the patch.

78. The system of claim 76, wherein the cartridge prevents movement of the patch during cutting of the patch with the at least one cutting member.

79. The system of claim 78, further comprising an element configured to apply tension to at least a portion of the patch prior to cutting the patch with the at least one cutting member.

80. The system of claim 76, wherein the material comprises biologically-derived material suitable for implantation into the eye.

81. The system of claim 80, wherein the biologically-derived material comprises tissue harvested from a donor or from the patient, allograft material, or xenograft material.

82. The system of claim 76, wherein the material comprises an engineered or 3D-printed material suitable for implantation into the eye.

83. The system of claim 76, wherein the implant comprises one or more therapeutic agents.

84. The system of claim 76, wherein the at least one cutting member comprises at least one pair of opposed cutting edges.

85. The system of claim 76, wherein a dimension of the implant substantially fills an internal dimension of the lumen of the elongate tubular member of the distal portion of the delivery instrument.

86. The system of claim 76, wherein the implant comprises a longitudinal axis and wherein the longitudinal axis of the implant is aligned with a longitudinal axis of the lumen of the elongate tubular member after completion of the cutting to form the implant.

87. The system of claim 76, wherein a distal end region of the elongate tubular member is at least one of angled or curved or flexible.

88. The system of claim 76, wherein the lumen comprises a circular cross-section.

89. The system of claim 76, further comprising an actuator on the handpiece, the actuator configured to retract the elongate tubular member from the implant while maintaining the implant position relative to adjacent eye tissue.

90. The system of claim 89, further comprising an internal elongate member configured to contact a proximal end of the implant while the elongate tubular member is retracted by the actuator.

91. The system of claim 89, wherein the actuator comprises at least one of a wheel, slide or button.

92. The system of claim 76, wherein a distal-most tip of the elongate tubular member is blunt to allow for dissecting eye tissue without cutting the eye tissue.

93. The system of claim 76, wherein each of the one or more windows has a depth that is at least as deep as a thickness of the implant.

\* \* \* \* \*